(12) United States Patent
Sonoda et al.

(10) Patent No.: US 8,083,715 B2
(45) Date of Patent: Dec. 27, 2011

(54) PUNCTURE DEVICE

(75) Inventors: Yutaro Sonoda, Ashigarakami-gun (JP); Tetsuro Kawanishi, Ashigarakami-gun (JP); Atsushi Matsumoto, Ashigarakami-gun (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 0 days.

(21) Appl. No.: 12/876,005

(22) Filed: Sep. 3, 2010

(65) Prior Publication Data
US 2010/0331875 A1    Dec. 30, 2010

Related U.S. Application Data

(62) Division of application No. 11/594,825, filed on Nov. 9, 2006.

(60) Provisional application No. 60/735,177, filed on Nov. 10, 2005.

(30) Foreign Application Priority Data

May 31, 2006    (JP) .................................. 2006-152318

(51) Int. Cl.
*A61M 5/00* (2006.01)
*A61M 5/32* (2006.01)
*A61B 17/34* (2006.01)

(52) U.S. Cl. ........ 604/115; 604/116; 604/117; 604/180; 606/185

(58) Field of Classification Search .................. 604/115, 604/227, 117, 116, 180, 181, 174; 606/181, 606/185
See application file for complete search history.

(56) References Cited

U.S. PATENT DOCUMENTS

| 4,403,987 | A  | * | 9/1983  | Gottinger ..................... 604/115 |
| 5,390,671 | A  |   | 2/1995  | Lord et al. |
| 5,437,640 | A  |   | 8/1995  | Schwab |
| 5,605,152 | A  |   | 2/1997  | Slate et al. |
| 6,162,195 | A  |   | 12/2000 | Igo et al. |
| 6,413,245 | B1 |   | 7/2002  | Yaacobi et al. |
| 6,494,865 | B1 |   | 12/2002 | Alchas |
| 6,592,552 | B1 |   | 7/2003  | Schmidt |
| 6,994,691 | B2 |   | 2/2006  | Ejlersen |
| 2003/0171716 | A1 | | 9/2003  | Ejlersen |
| 2005/0256499 | A1 | | 11/2005 | Pettis et al. |
| 2007/0005017 | A1 | | 1/2007  | Alchas et al. |
| 2007/0156096 | A1 | | 7/2007  | Sonoda et al. |
| 2007/0167970 | A1 | | 7/2007  | Sonoda et al. |

FOREIGN PATENT DOCUMENTS

| JP | 57-139358 A | 8/1982 |
| JP | 07-275227 A | 10/1995 |
| JP | 8-107890 A | 4/1996 |
| JP | 2001-137343 A | 5/2001 |

(Continued)

*Primary Examiner* — Jackie Ho
*Assistant Examiner* — Bradley Thomas, Jr.
(74) *Attorney, Agent, or Firm* — Buchanan Ingersoll & Rooney PC

(57) ABSTRACT

The present invention provides a puncture device and an administration device in which a puncture needle can be stuck certainly to a predetermined region of a skin. The puncture device and the administration device of the present invention are provided with a puncture needle moving means for retaining aforesaid puncture needle to be movable and a skin deforming means for deforming the skin, wherein it is constituted such that the puncture needle is moved by aforesaid puncture needle moving means and punctures the skin deformed by aforesaid skin deforming means.

6 Claims, 28 Drawing Sheets

FOREIGN PATENT DOCUMENTS

| | | |
|---|---|---|
| JP | 2001-516625 A | 10/2001 |
| JP | 2003-511204 A | 3/2003 |
| JP | 2005-087519 A | 4/2005 |
| JP | 2005-518253 A | 6/2005 |

* cited by examiner

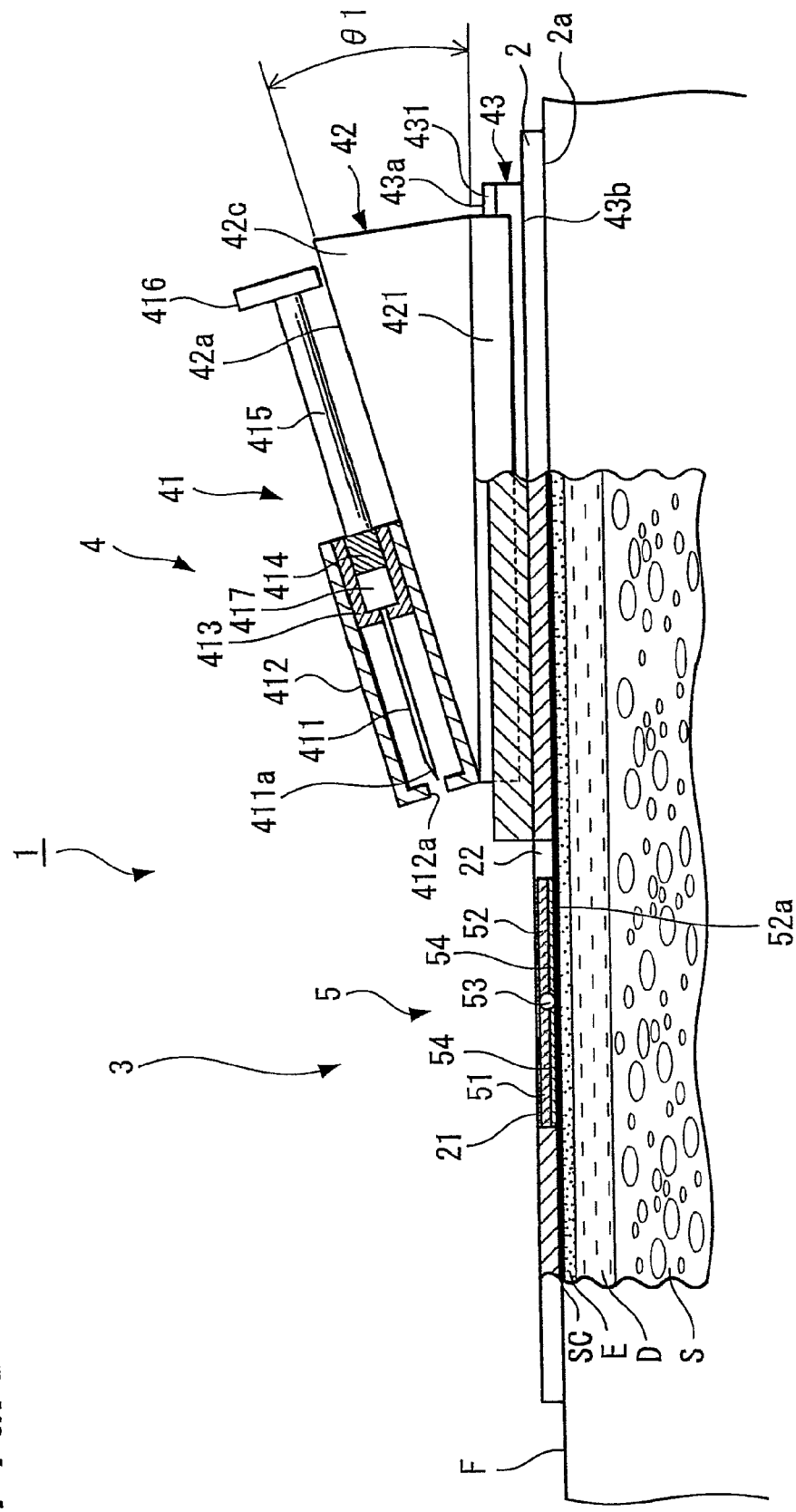

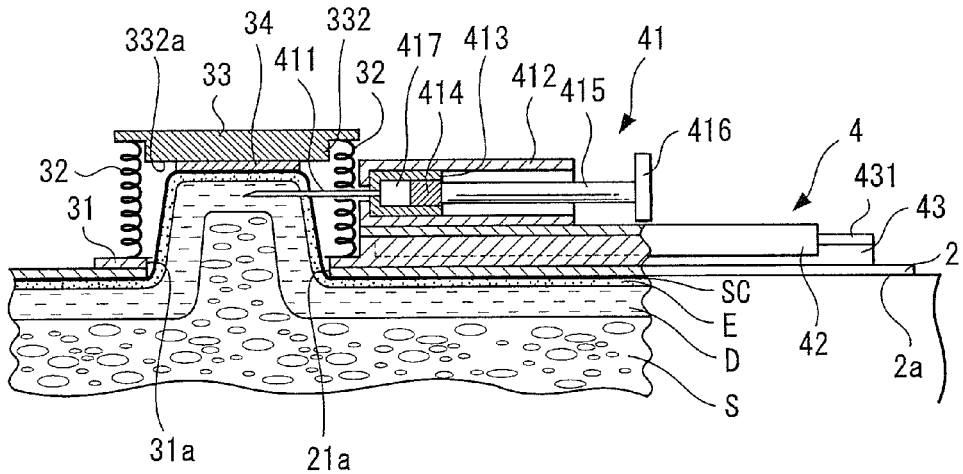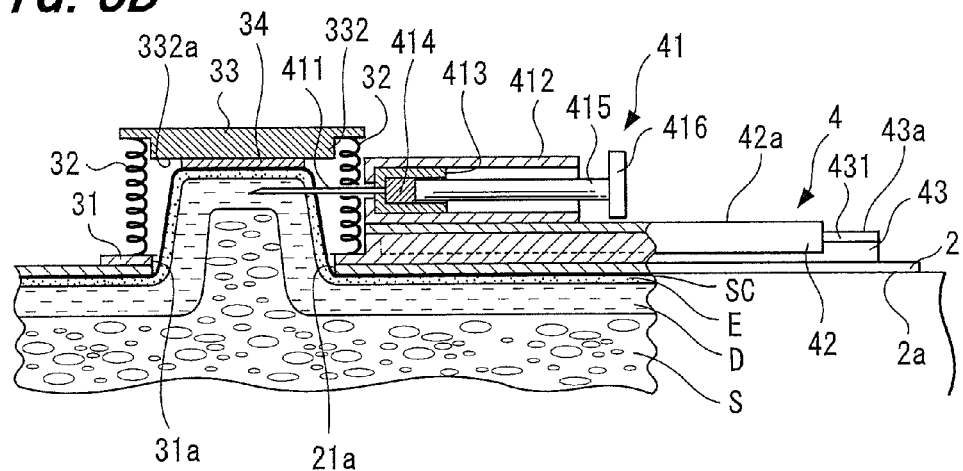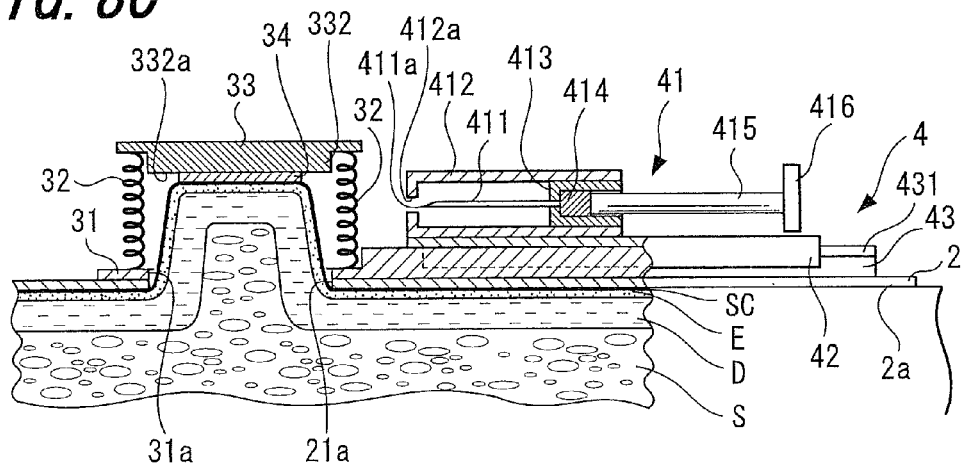

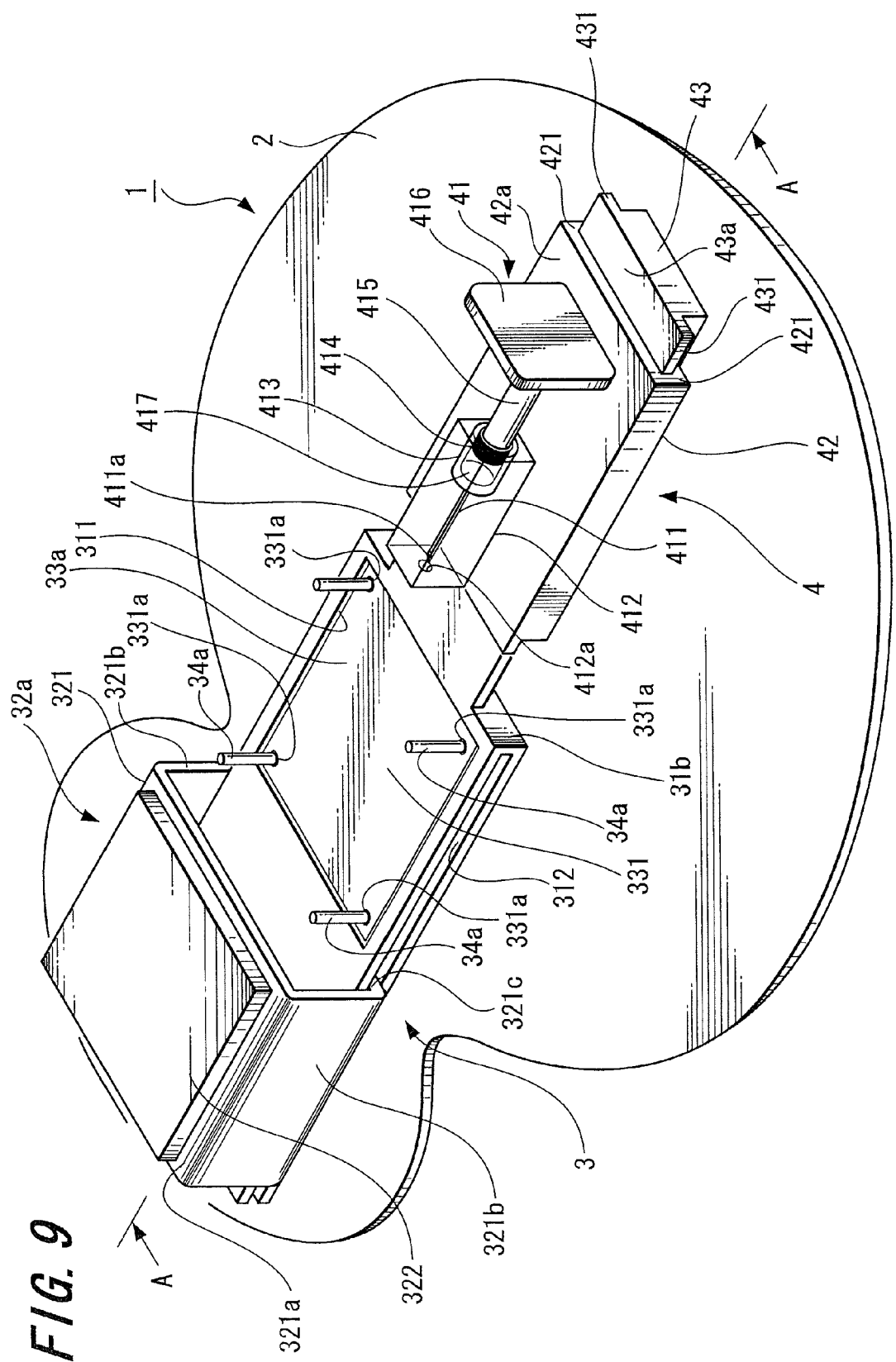

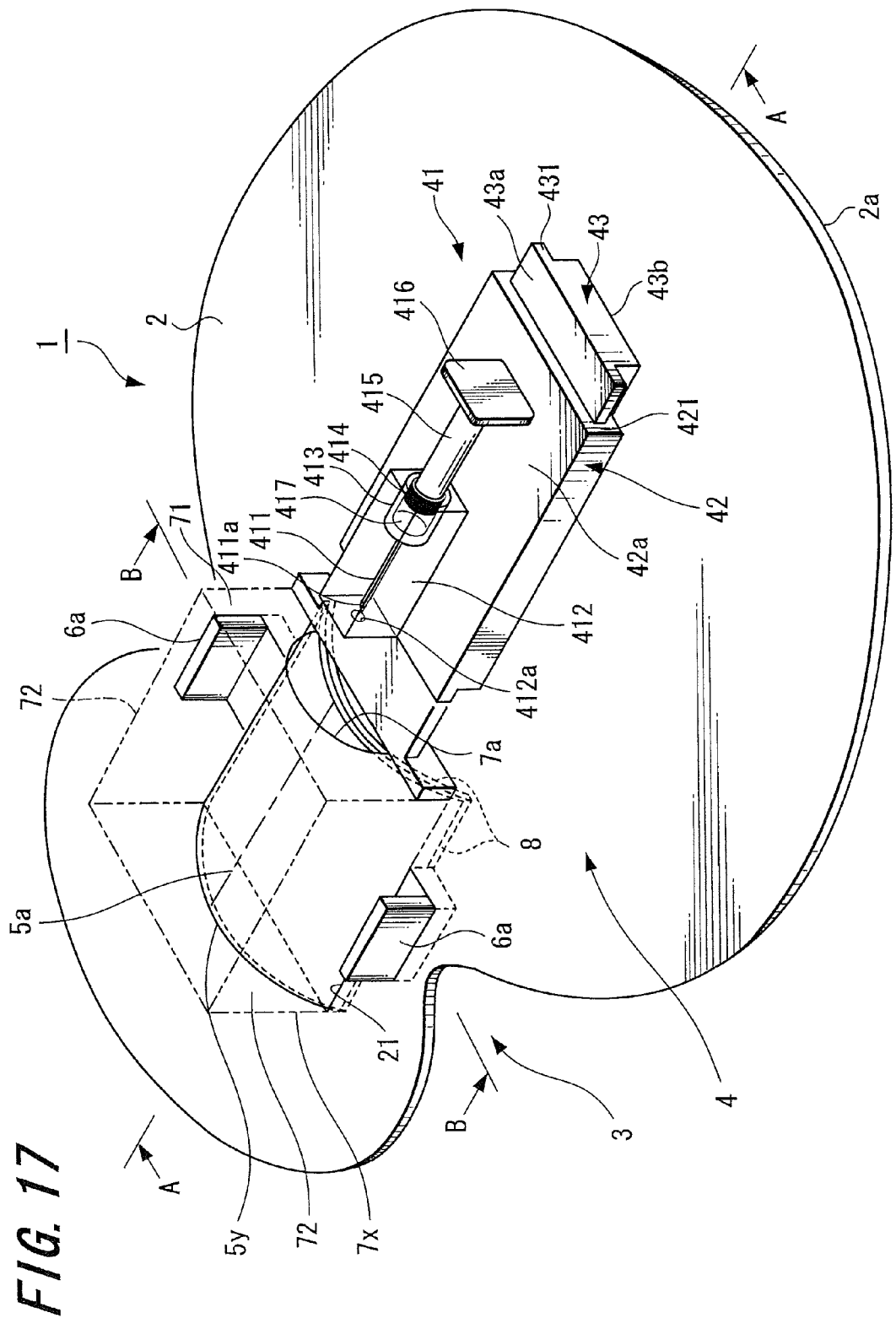

PUNCTURE DEVICE

This application is a divisional of U.S. application Ser. No. 11/594,825 filed Nov. 9, 2006, which claims the benefit of priority under 35 U.S.C. §119 (e) of U.S. Application No. 60/735,177 filed Nov. 10, 2005, the entire content of both of which is incorporated herein by reference.

TECHNICAL FIELD

The present invention relates to a puncture device and relates to a puncture device which punctures from the surface of skin and is used with respect to a predetermined region (for example, dermis).

Also, the present invention relates to an administration device and relates to an administration device which punctures from the surface of skin and administers a substance with respect to a predetermined region (for example, dermis).

Also, the present invention relates to a puncturing method puncturing from the surface of skin to a predetermined region (for example, dermis) by using a puncture device or the like.

BACKGROUND ART

It is known that the dermis has a high density of capillary blood vessel when compared with an epidermis or a subcutis and also a lymph vessel end exists therein, so that in particular, a medical agent injected thereto directly is shifted to a blood vessel or a lymph vessel and an absorption speed thereof being absorbed in the body fluid is speedy. In particular, it is possible in the dermis to make a medical agent using a macromolecular substance such as hormone, antibody drug, cytokine and the like to be absorbed into the blood efficiently. Also, it is known that the dermis is a place of efficient immunity and it is possible to make a saving of applied dose of vaccine or to strengthen sensitization of a weak vaccine, so that it is possible to make a saving of immune cells to be administered or to strengthen the effect thereof.

Also, it is known for adult human beings that the dermis exists approximately in a certain amount of depth from the body surface (surface of stratum corneum). In other words, this fact means in case of injecting a medical agent into the dermis that it is possible to use a puncture needle having the same length (depth) with respect to these human beings.

Generally, the width of the dermis is around 1 mm to 4 mm (average value is 1 mm to 2 mm) if the vertical direction with respect to the body surface is made to be a reference and also, as shown in FIG. 29, the dermis exists in the skin so as to be sandwiched between an epidermis E which includes a stratum corneum and has width of around 0.06 mm to 0.1 mm and a subcutis S.

Accordingly, it is difficult to insert an tip portion of the puncture device, for example, a needlepoint of the puncture needle accurately to the dermis which exists between the epidermis and the subcutis, and if the needlepoint is inserted erroneously to the subcutis or the like, there occurs a problem such that a medical agent cannot be absorbed efficiently.

In recent years, for example, it is attempted that the macromolecular medicine mentioned above is administered continually or by one-shot into the dermis as a target, and in such a case, in particular, the above-mentioned problem becomes conspicuous.

Here, a hypodermic injection device is known in which the length of the puncture needle to be inserted into the body is defined in order to inject a medical agent to the dermis in the body (Patent Document 1). In addition, a medicinal solution injection device is also known in which the depth (insertion depth) of the puncture needle to be inserted into the skin is defined to be a predetermined length in order to inject a medical agent into a specific layer which exists in the skin and the puncture needle is inserted into the skin from the vertical direction with respect to the body surface (Patent Document 2). Also, a medicinal solution injection device is known in which a medical agent or the like is injectable with a predetermined pressure (Patent Document 3).

[Patent Document 1] Japanese Patent Laid-open No. 2001-137343

[Patent Document 2] Japanese Patent Laid-open No. 2005-87519

[Patent Document 3] US Patent Publication No. 2005/256499

DISCLOSURE OF THE INVENTION

However, there is employed in these devices a constitution in which the puncture needle is inserted into the skin from the vertical direction with respect to the body surface. In this case, if it is attempted to puncture with the puncture needle, the whole skin is sunk in elastically so as not to be punctured and also, even if it is punctured, it sometimes happens that the needlepoint cannot reach the dermis.

Also, when the puncture needle is inserted perpendicularly with respect to the dermis, the depth (insertion depth) of the puncture needle in the dermis becomes short and, for example, in such a case where some kind of shock or the like is added from the outside, there occurs a problem in which the puncture needle during injecting a medical agent drops out from the dermis.

Further, in case of using these devices, the distance from an insertion aperture of the puncture needle which is formed on the surface of the dermis (boundary portion of epidermis and dermis) to a medical agent releasing aperture which exists at the tip of the puncture needle becomes short in the dermis. For that reason, there is a fear that the medical agent injected to the dermis from the medical agent releasing aperture is to leaks from the insertion aperture to the outside of the dermis (epidermis). Then, the medicinal solution becomes effective when a decided amount of the solution is administered, so that a problem is to occur that expected effect cannot be achieved if the amount of the leakage to the outside of the body is large.

Also, generally, it is recommended to inject the medicinal solution relatively at low flow velocity in order not to make the medicinal solution leak from the skin. However, in a tissue having a high density such as the dermis, there is a fear that the medicinal solution may leak by not enduring the administration pressure thereof even if injecting the medicinal solution relatively at low flow velocity, so that it is necessary to inject the medicinal solution further at lower flow velocity. Consequently, there was a problem that the injection time of the medicinal solution extends over a long time in order to inject the medicinal solution into the tissue having a high density such as the dermis without leakage.

In consideration of the above-mentioned problems, an object of the present invention lies in providing a puncture device which can stick a puncture needle certainly to a predetermined region of a skin.

Also, in consideration of the above-mentioned problems, an object of the present invention lies in providing an administration device which can administer a predetermined amount of substance to a predetermined layer of a skin, for example, to the dermis continuously without leakage or can administer it thereto certainly and relatively in a short time.

A puncture device relating to the present invention is a device which punctures a skin by a puncture needle in which there is provided with a puncture needle moving means for retaining aforesaid puncture needle to be movable and a skin deforming means for deforming a skin, characterized by being constituted such that the puncture needle is moved by aforesaid puncture needle moving means and the skin deformed by aforesaid skin deforming means is to be punctured.

According to the puncture device relating to the present invention, it is possible to reach a predetermined region certainly by sticking a puncture needle to the skin. Also, it is possible to inject a medical agent certainly into a predetermined region.

Also, an administration device relating to the present invention is provided with a puncture device that has one puncture needle puncturing a skin and makes aforesaid puncture needle to go into in parallel with respect to a predetermined layer of aforesaid skin; and an injection device which is in communication with aforesaid puncture needle and at the same time injects a substance to a predetermined layer of aforesaid skin through aforesaid puncture needle, characterized in that aforesaid substance is administered to a dermis within aforesaid skin layers in a range of 0.1 psi to 500 psi with respect to pressure.

According to the administration device relating to the present invention, it is possible to administer a predetermined amount of substance with respect to the skin without leakage.

BRIEF DESCRIPTION OF DRAWINGS

[FIG. 2] A cross-section view by A-A line in FIG. 1;

[FIG. 8] Second diagrams (cross-section views) for explaining usage of the puncture device shown in FIG. 5;

[FIG. 9] A perspective view showing a third exemplified embodiment of a puncture device of the present invention;

[FIG. 17] A perspective view showing a fifth exemplified embodiment of a puncture device of the present invention;

BEST MODE FOR CARRYING OUT THE INVENTION

Figure 1:
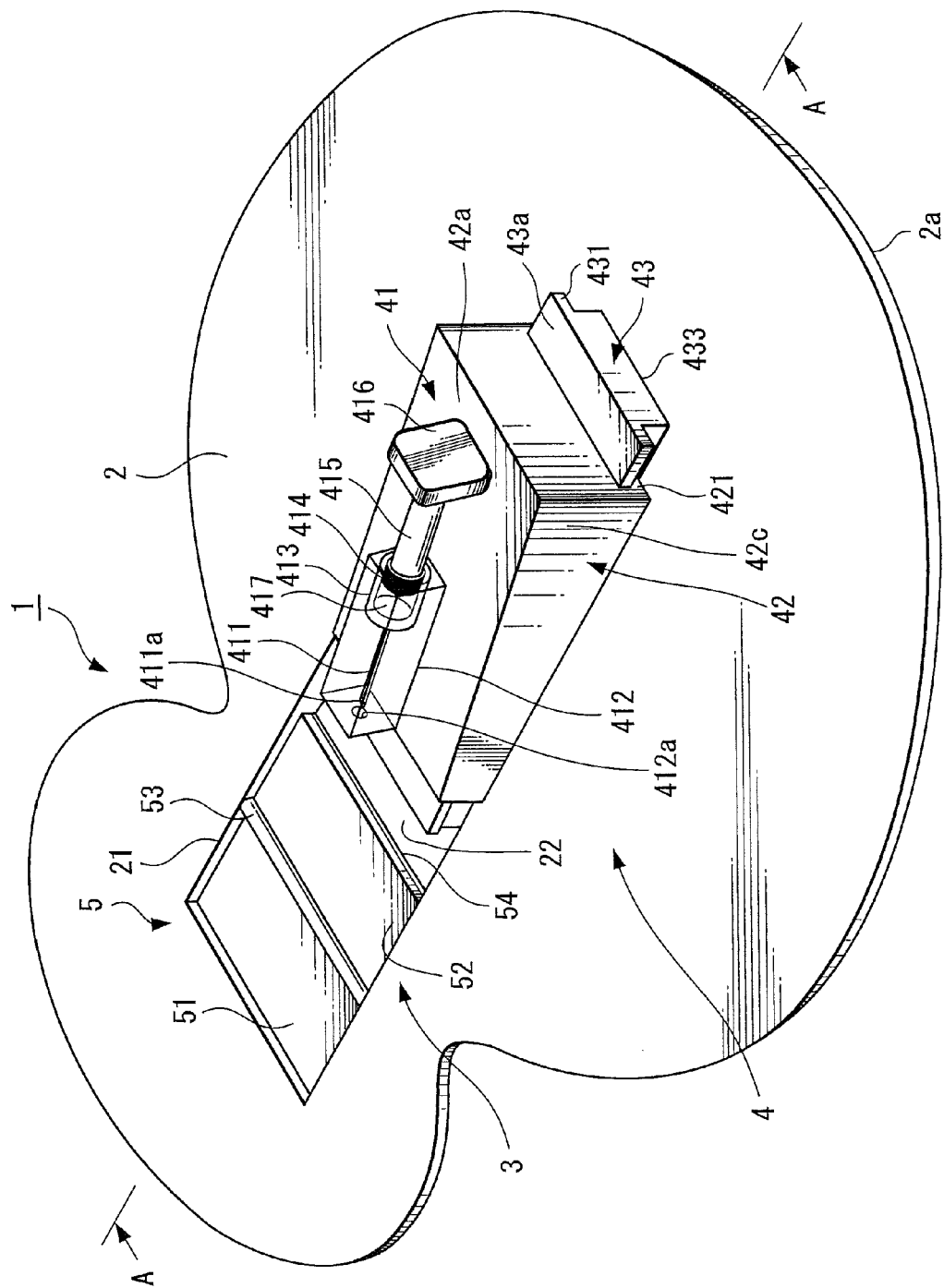
[FIG. 1] A perspective view showing a first exemplified embodiment of a puncture device of the present invention.

A puncture device relating to an exemplified embodiment of the present invention is a puncture device puncturing a skin by a puncture needle and is provided with a puncture needle moving means for retaining aforesaid puncture needle to be movable and a skin deforming means for deforming the skin, wherein it is constituted such that the puncture needle is moved by aforesaid puncture needle moving means and punctures the skin deformed by aforesaid skin deforming means. By employing this constitution, it is possible to stick the puncture needle to the skin so as to be reached to a predetermined region certainly.

The above-described puncture device relating to an exemplified embodiment of the present invention includes a fixing portion having a plane to be fixed on the skin and a skin fixing plane equipped in aforesaid skin deforming means, wherein it is constituted such that aforesaid skin deforming means deforms the skin so as to form a step portion between aforesaid skin fixing plane and the plane of aforesaid fixing portion.

It is constituted such that aforesaid puncture needle moving means of the puncture device relating to an exemplified embodiment of the present invention moves aforesaid puncture needle approximately in parallel with respect to aforesaid skin fixing plane and aforesaid step portion is to be punctured.

It is constituted such that aforesaid puncture needle moving means of a puncture device relating to an exemplified embodiment of the present invention moves aforesaid puncture needle approximately in parallel with respect to the plane of aforesaid fixing portion and aforesaid step portion is to be punctured.

An administration device relating to an exemplified embodiment of the present invention is provided with a puncture device that has one puncture needle puncturing a skin and makes aforesaid puncture needle to go into in parallel with respect to a predetermined layer of aforesaid skin; and an injection device which is in communication with aforesaid puncture needle and at the same time injects a substance to a predetermined layer of aforesaid skin through aforesaid puncture needle, wherein it is constituted such that aforesaid substance is administered to a dermis within aforesaid skin layers in a range of 0.1 psi to 500 psi with respect to pressure. By employing this constitution, it is possible to administer a predetermined amount of substance with respect to the skin without leakage.

The above-described administration device relating to an exemplified embodiment of the present invention is made to have a constitution in which aforesaid substance is administered by a predetermined time when the aforesaid substance is administered by an administration flow velocity of 100 µl/minute.

An administration device relating to an exemplified embodiment of the present invention is made to have a constitution in which aforesaid substance is administered by administration flow velocity 1000 to 2000 µl/minute when the pressure is in a range of 90 psi to 500 psi.

The above-described administration device relating to an exemplified embodiment of the present invention is made to have a constitution in which the administration time is 130 seconds or less when aforesaid substance is administered with administration flow velocity by 1000 µl/minute.

The above-described administration device relating to an exemplified embodiment of the present invention is made to have a constitution in which the administration time is 90 seconds or less when aforesaid substance is administered with administration flow velocity by 2000 µl/minute.

The above-described administration device relating to an exemplified embodiment of the present invention is made to have a constitution in which the maximum pressure of aforesaid substance is 200 psi to 500 psi when the administration flow velocity is made to be 1000 µl to 2000 µl/minute.

The above-described administration device relating to an exemplified embodiment of the present invention is made to have a constitution in which aforesaid substance is administered for a predetermined time in a state in which the maximum pressure of aforesaid substance is 460 psi.

The above-described administration device relating to an exemplified embodiment of the present invention is made to have a constitution in which aforesaid predetermined time is 90 seconds or less.

The above-described administration device relating to an exemplified embodiment of the present invention is made to have a constitution in which a puncture device comprises a puncture needle moving means for retaining aforesaid puncture needle to be movable and a skin deforming means for deforming aforesaid skin, aforesaid puncture needle is moved by aforesaid puncture needle moving means, and aforesaid skin deformed by aforesaid skin deforming means is to be punctured.

The above-described administration device relating to an exemplified embodiment of the present invention is made to have a constitution in which with respect to the puncture device, aforesaid puncture needle is made to go into the skin at least by 0.5 mm.

An administration device relating to another exemplified embodiment of the present invention is made to have a constitution in which there is provided with a puncture device that has one puncture needle puncturing a skin and makes said puncture needle to go into the skin at least by 0.5 mm; and an injection device which is made to be in communication with said puncture needle and at the same time injects a substance to a predetermined layer of said skin through said puncture needle, wherein the maximum pressure of the substance is 200 psi to 500 psi when the administration flow velocity is made to be 1000 µl to 2000 µl/minute. By employing this constitution, it is possible to administer a predetermined amount of substance with respect to the skin without leakage.

A puncturing method relating to an exemplified embodiment of the present invention is a method in which in order to stick the puncture needle to a predetermined region of the skin certainly, there are used a puncture needle moving means for retaining aforesaid puncture needle to be movable; and a skin deforming means for deforming aforesaid skin, wherein the puncture needle is moved by aforesaid puncture needle moving means so as to puncture the skin deformed by aforesaid skin deforming means. According to this method, it is possible to stick the puncture needle to the skin so as to be reached to a predetermined region certainly.

The aforesaid puncturing method relating to an exemplified embodiment of the present invention is a method in which the skin is deformed by aforesaid skin deforming means such that a step portion is to be formed between a skin fixing plane and a plane of a fixing portion provided in aforesaid puncture device.

The aforesaid puncturing method relating to an exemplified embodiment of the present invention is a method in which aforesaid puncture needle is moved by aforesaid puncture needle moving means approximately in parallel with aforesaid skin fixing plane so as to puncture aforesaid step portion.

The aforesaid puncturing method relating to an exemplified embodiment of the present invention is a method in which aforesaid puncture needle is moved by aforesaid puncture needle moving means approximately in parallel with the plane of aforesaid fixing portion so as to puncture aforesaid step portion.

Hereinafter, it will be explained with respect to embodiments for practicing the puncture device of the present invention with reference to the drawings, wherein it should be noted that the present invention is not limited by the following embodiments.

First Exemplified Embodiment

First, it will be explained with respect to a first exemplified embodiment of a puncture device of the present invention.

FIG. 1 is a perspective view showing a first exemplified embodiment of a puncture device of the present invention. FIG. 2 is a diagram showing a cross-section view by A-A line in FIG. 1. Also, FIG. 3 and FIG. 4 are diagrams (cross-section views) for explaining usage of the puncture device shown in FIG. 1. It should be noted that it will be explained hereinafter on an assumption that the right side in FIG. 2 to FIG. 4 is made to be "rear end" and the left side thereof is made to be "tip".

A puncture device 1 shown in FIG. 1 is provided with an adhesive pad 2 which is a fixing portion, a skin deforming means 3 for deforming and uplifting a skin and a puncture needle moving means 4 for retaining a puncture needle 411 to be movable.

The adhesive pad 2 is almost rounded and is formed so as to have a shape in which facing concave portions are formed at portions of the circumference thereof, so-called, a wing-like shape.

It should be noted that the wing-like shape of the adhesive pad 2 is formed such that the area of the side on which the puncture needle moving means 4 is mounted becomes larger than the area of the side on which the skin deforming means 3 is provided. In this manner, by making the area of the adhesive pad 2 on the side on which the puncture needle moving means 4 is mounted to be larger, it is possible to increase stability with respect to a body surface F and to carry out the movement of the puncture needle 411 by means of the puncture needle moving means 4 in a stable state.

The adhesive pad 2 is formed with a hinge opening 21 for mounting a hinge 5 which is the skin deforming means 3 on the body surface F. Also, the adhesive pad 2 is formed with a puncture needle opening 22 which is positioned adjacently with the hinge opening 21 so as to be along the moving direction of the puncture needle 411.

The puncture needle opening 22 is formed so as to be opened from a base end portion of a turning piece 52 of the hinge 5 to be described hereinafter until a tip portion of a support member 43. Also, the width of the puncture needle opening 22 is formed so as to be approximately identical with the width of the turning piece 52. In this manner, a gap is formed between the base end side of the turning piece 52 and the tip portion of the support member 43, so that it becomes easy to uplift the skin by means of the turning piece 52. Also, it becomes easy owing to the gap to grasp the edge portion of the turning piece 52, so that it is possible to turn the turning piece 52 easily.

As shown in FIG. 2, there is formed on the body surface F side of the adhesive pad 2 with a plane 2a for fixing the adhesive pad 2 on the body surface F (skin) by being appressed thereto. This plane 2a is provided with an adhesion means and for the adhesion means, it is allowed to apply an adhesive agent on the plane 2a in the form of laminae or it is also allowed to attempt gluing an adhesive film constituted by a two-sided tape thereon.

The plane 2a of the adhesive pad 2 is fixed on the body surface F by the adhesive agent. It should be noted that there are arranged, on the lower side of the body surface F, a stratum corneum SC, an epidermis E including the stratum corneum SC, a dermis D and a subcutis S in the form of laminae.

Then, as being described hereinafter, the puncture needle 411 is moved to the tip direction along the plane 2a of the adhesive pad 2 by the puncture needle moving means 4 and the skin uplifted by the skin deforming means 3 is to be punctured.

The adhesive pad 2 is constituted, for example, by soft polymer such as flexible polyurethane or the like.

The skin deforming means 3 is constituted by a tabular hinge 5 composed of a fixed piece 51 and a turning piece 52 which are a pair of fixed pieces, and a turning axis 53 interlinking the fixed piece 51 and the turning piece 52 which is provided between the fixed piece 51 and the turning piece 52. Also, the turning piece 52 is supported by the turning axis 53 so as to turn in the vertical direction with respect to the moving direction of the puncture needle 411.

Also, there is formed on the body surface F side of the turning piece 52 with a skin fixing plane 52a for fixing the skin.

The hinge 5 is mounted on the body surface F through the hinge opening 21 formed on the adhesive pad 2. Also, there is provided on the body surface F side of the fixed piece 51 and turning piece 52 with an adhesive film 54 as the bonding means and as shown in FIG. 2, the hinge 5 is fixed on the body surface F by this adhesive film 54. For the bonding means, for example, an adhesive film of a two-sided tape or the like is used.

The hinge 5 is constituted by a metal material, but it is not necessary to be limited by a metal material in particular if only it has stiffness of a high degree such that the height of the skin to be uplifted can be defined accurately. In this manner, by constituting the hinge 5 with a material having higher hardness than that of the material of the adhesive pad 2, it is possible to lift up the skin certainly in the vertical direction with respect to the body surface F.

In addition, it is also allowed for the hinge 5 to have such a constitution in which the area of the fixed piece 51 becomes larger than the area of the turning piece 52. By constituting in this manner, it is possible to uplift the skin by the turning piece 52 while the fixed piece 51 is fixed on the body surface F certainly and the stable state is maintained.

The puncture needle moving means 4 is constituted by an injector 41 having the puncture needle 411, amounting member 42 for mounting and fixing the injector 41 and a support member 43 for supporting the mounting member 42 to be movable.

Also, the support member 43 of the puncture needle moving means 4 is constituted integrally with the fixed piece 51 of the hinge 5 by a frame material (not shown).

The injector 41 is provided with the puncture needle 411, a fixed outer cylinder 412, an internal outer cylinder 413 slidable in the fixed outer cylinder 412, a gasket 414 slidable in the internal outer cylinder 413 and a plunger 415 which moving-operates the gasket 414.

The fixed outer cylinder 412 has a cylindrical shape with bottom and is mounted and fixed on the mounting member 42 by means of adhesive agent or the like. Also, there is formed in the vicinity of the central portion of the bottom portion of the fixed outer cylinder 412 with a puncture needle opening 412a for carrying out insertion of the puncture needle 411.

The internal outer cylinder 413 has a cylindrical shape with bottom. Also, the puncture needle 411 is firmly fixed by adhesion in the vicinity of the central portion of the bottom portion.

The needlepoint 411a of the puncture needle 411 is provided so as not to project from the puncture needle opening 412a which is provided at the fixed outer cylinder 412. More specifically, the puncture needle 411 is located with respect to the fixed outer cylinder 412 such that the needlepoint 411a thereof is to be positioned on the inner side as compared with the bottom face of the fixed outer cylinder 412 at which the puncture needle opening 412a is provided and also in the vicinity of the puncture needle opening 412a.

By constituting in this manner, it is possible to protect the needlepoint 411a of the puncture needle 411. Also, it is possible to reduce awful feeling of a user, because the needlepoint 411a becomes hard to be seen.

The outer diameter of the puncture needle 411 is a little bit different depending on the use application or the like of the puncture device 1, but it is preferable to be around 0.05 mm to 2.0 mm and in particular, it is preferable to be around 0.1 mm to 1.0 mm.

For the constituent material of the puncture needle 411, there can be cited, for example, a metal material such as stainless steel, aluminum or aluminum alloy, titanium or titanium alloy or the like. Also, the puncture member 411 is manufactured, for example, by plastic working.

It is possible for the internal outer cylinder 413 to slide in the fixed outer cylinder 412 in a longitudinal direction of the internal outer cylinder 413 by means of the operation of the plunger 415 and when the internal outer cylinder 413 slides, the puncture needle 411 firmly fixed to the internal outer cylinder 413 is taken in and out with respect to the fixed outer cylinder 412 through the puncture needle opening 412a.

For the constituent material of the fixed outer cylinder 412 and the internal outer cylinder 413, there can be cited various kinds of resins such, for example, as polyvinylchloride, polyethylene, polypropylene and the like. It should be noted that the constituent material of the fixed outer cylinder 412 and the internal outer cylinder 413 is desirable to be substantially transparent in order to ensure visibility of the inside.

There is housed, in the internal outer cylinder 413, the gasket 414 constituted by an elastic material.

For the constituent material of the gasket 414, although it is not limited in particular, there can be cited, for example, various kinds of rubber materials such as natural rubber and silicone rubber, various kinds of thermoplastic elastomers of polyurethane series, styrene series and the like or elastic materials of mixtures thereof and the like.

In the space surrounded by the gasket 414 and internal outer cylinder 413, a liquid room 417 is formed and in this liquid room 417, liquid is contained liquid-tightly beforehand.

There can be cited for the liquid, for example, remedy for injection or medicinal solution using a macromolecular substance such as hormone, antibody drug, cytokine, vaccine or the like.

There is interlinked to the gasket 414 the plunger 415 which moving-operate the gasket 414 in the internal outer cylinder 413 in a longitudinal direction.

A plate-like flange 416 is formed integrally at the rear end of the plunger 415. The plunger 415 is operated by depressing this flange 416 with a finger or the like.

The mounting member 42 is constituted so as to include an upper surface portion 42a for mounting the injector 41. At the lower portion in a longitudinal direction of the mounting member, there is formed, by being projected toward the adhesive pad 2, a U-shaped engagement portion 421 to be movable and for being engaged with the support member 43.

On the mounting member 42, there is provided with an inclined portion 42c in a state in which the upper surface portion 42a has a predetermined angle θ1 with respect to the moving direction of the puncture needle 411. Also, the angle of gradient θ1 of this inclined portion is set so as to be identical with the turning angle θ2 of the turning piece 52 of the hinge 5 shown in FIG. 3B.

The support member 43 is constituted by a rectangular plate-like body having an upper surface portion 43a which contacts slidably with a mounting member 42. At the edge portion in a longitudinal direction of the plate-like body, there is formed, by being projected to the horizontal direction with respect to the adhesive pad 2, an engagement convex portion 431 which has such a shape to coincide with the U-shaped engagement portion 421 which is formed on the mounting member 42.

On the plane on the opposite side of the upper surface portion 43a of the support member 43, there is formed a lower surface portion 43b for being fixed with the adhesive pad 2 adhesively. As shown in FIG. 2, the lower surface portion 43b is fixed on the adhesive pad 2 by adhesive agent or the like.

There can be cited for the constituent material of the mounting member 42 and the support member 43 various kinds of resins such as polyethylene, polypropylene or the like and the mounting member 42 and the support member 43 are manufactured by a forming process in pouring these resins into a die which has a predetermined shape or the like.

It should be noted as the puncture needle moving means 4 that it is allowed to employ such a constitution wherein an injector having a constitution in which a puncture needle and a syringe are formed as one body configuration is fixed and retained on the mounting member 42. In this case, the length of the puncture needle 411 is adjusted such that the needle-point 411a of the puncture needle 411 can puncture the skin uplifted by the skin deforming means 3 when the mounting member 42 is moved so as to most approach to the skin deforming means 3.

Next, it will be explained by using FIG. 3 and FIG. 4 with respect to usage (operation) of the puncture device 1 of this exemplified embodiment.

First, the adhesive pad 2 is mounted on a predetermined position of the body surface F.

At that time, the plane 2a of the adhesive pad 2 is bonded and fixed on the body surface F by means of an adhesive film provided on the body surface F side of the adhesive pad 2.

At the same time, also the hinge 5 which is located so as to mesh with the hinge opening 21 formed on the adhesive pad 2 is mounted on the body surface F. At that time, the hinge 5 is bonded and fixed on the body surface F by means of the adhesive film 54 provided on the body surface F side of the fixed piece 51 and turning piece 52 of the hinge 5.

Figure 3A:
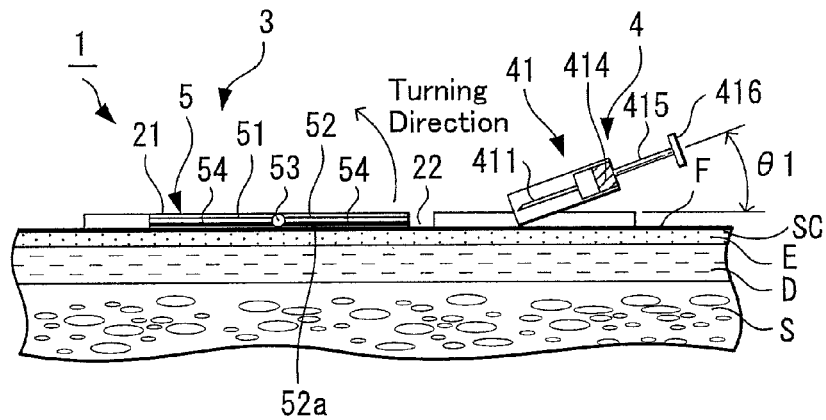
[FIG. 3] Diagrams (cross-section views) for explaining usage of the puncture device shown in FIG. 1.

Next, by grasping the turning piece 52 of the hinge 5, the turning piece 52 is turned to the direction of the arrow shown in FIG. 3A centering around the turning axis 53.

When the turning piece 52 is turned upward, the skin bonded to the adhesive film 54 which is provided on the body surface F side of the turning piece 52 is pulled out upward with respect to the body surface F together with the turning of the turning piece 52. More specifically, the epidermis E including the stratum corneum SC, the dermis D and the subcutis S are pulled out upward respectively and the skin is uplifted to the vertical direction with respect to the body surface F. In this case, the dermis D pulled out by the turning piece 52 is uplifted in a state parallel with the turned turning piece 52.

Also, the turning axis 53 of the hinge 5 is arranged so as to be in the vertical direction with respect to the moving direction of the puncture needle 411, so that the skin is uplifted in a state in which the region (puncture region P) of the skin to be punctured is to be faced to the needlepoint 411a of the puncture needle 411.

More specifically, depending on a fact that the skin is deformed and uplifted, the position of the plane 2a of the adhesive pad 2 which is the fixing portion and the position of the skin fixing plane 52a of the turning piece 52 become different in the height direction, a step portion is formed there-between and a puncture region P is formed on the step portion thereof. Here, the step means difference of the height which occurs between the plane 2a and the skin fixing plane 52a.

Figure 3B:
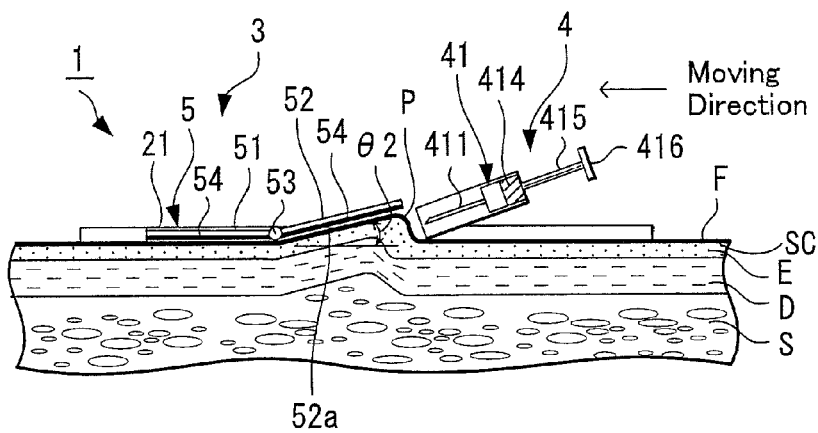

The turning of the turning piece 52 stops when it reaches a turning angle θ2 which was set beforehand. The turning angle θ2 of the turning axis 53 is set to be an angle, as shown in FIG. 3B, in which at least the dermis D is to be projected upward beyond the body surface F.

Next, the mounting member 42 on which the injector 41 is fixedly retained is slid to the tip direction. More specifically, the bottom face of the fixed outer cylinder 412 and the puncture region P are made to be adjacent and the needlepoint 411a of the puncture needle 411 is made to approach to the puncture region P.

Figure 3C:
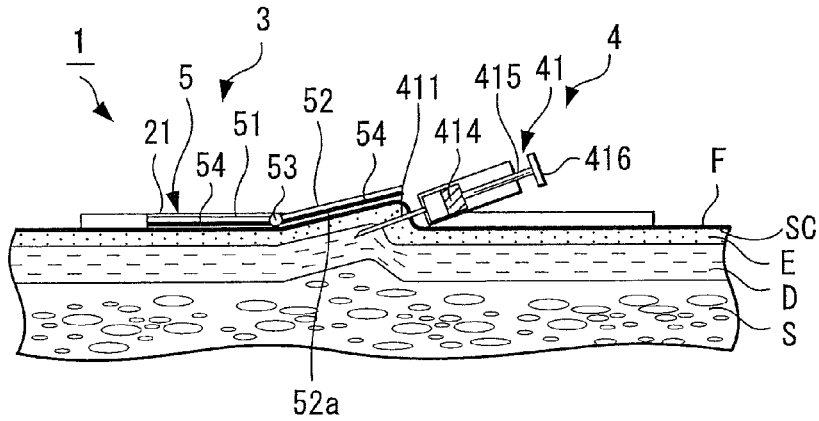

Next, the plunger 415 is operated by depressing the flange 416 with a finger or the like and the internal outer cylinder 413 is moved to the tip direction while it is slided together with the fixed outer cylinder 412. Thereby, the puncture needle 411 firmly fixed to the internal outer cylinder 413 is inserted into the puncture region P from the puncture needle opening 412a and as shown in FIG. 3C, the needlepoint 411a of the puncture needle 411 is punctured into the dermis D by bypassing the epidermis E including the stratum corneum SC.

In this exemplified embodiment, the upper surface portion 42a of the mounting member 42 on which the injector 41 is fixedly retained is provided with the angle of gradient θ1 which becomes identical with the turning angle θ2 of the turning piece 52 of the hinge 5, so that the needlepoint 411a of the puncture needle 411 is stuck into the step portion (puncture region P) in a state parallel with the skin fixing plane 52a of the turning piece 52. More specifically, it is possible to insert the puncture needle 411 into the dermis D so as to become parallel with the dermis D which was uplifted in parallel with the turning piece 52.

At that time, the puncture needle 411 is stuck by a distance of 0.3 mm to 30.0 mm and preferably of 3.0 mm to 8.0 mm with respect to the skin and it is possible to be inserted by a distance of 2.0 mm to 8.0 mm with respect to the dermis D.

Figure 4A:
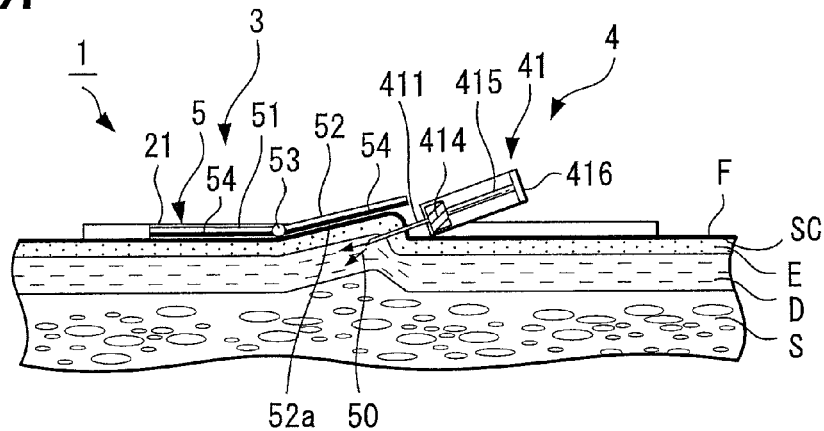
[FIG. 4] Diagrams (cross-section views) for explaining usage of the puncture device shown in FIG. 1.

The plunger 415 is operated by further depressing the flange 416 with a finger or the like from that state and the gasket 414 is moved to the tip direction while sliding it together with the internal outer cylinder 413. Thereby, as shown in FIG. 4A, a medical agent 50 contained in the liquid room 417 is injected from the needlepoint 411a of the puncture needle 411 to the dermis D.

After the medical agent is injected into the dermis D, the plunger 415 is operated by pulling the flange 416 with a finger or the like, the gasket 414 is moved to the rear end direction and the puncture needle 411 is pulled out from the puncture region P.

Figure 4B:
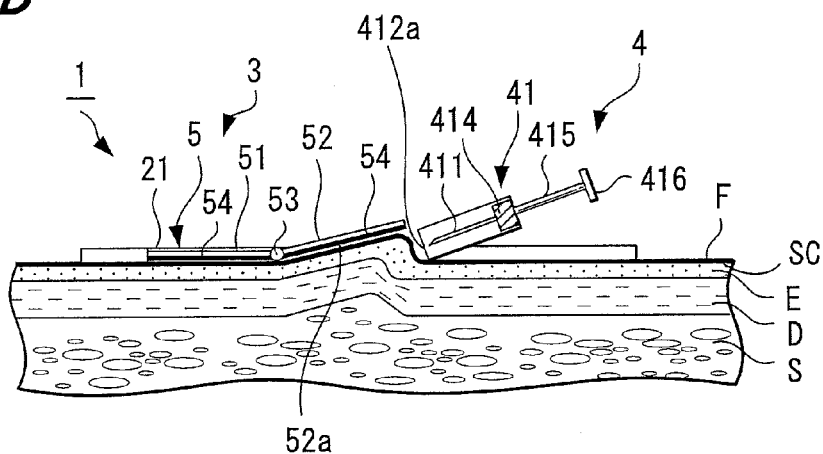

Further, the plunger 415 is moved to the rear end direction and as shown in FIG. 4B, the puncture needle 411 is housed in the fixed outer cylinder 412 from the puncture needle opening 421a.

Figure 4C:
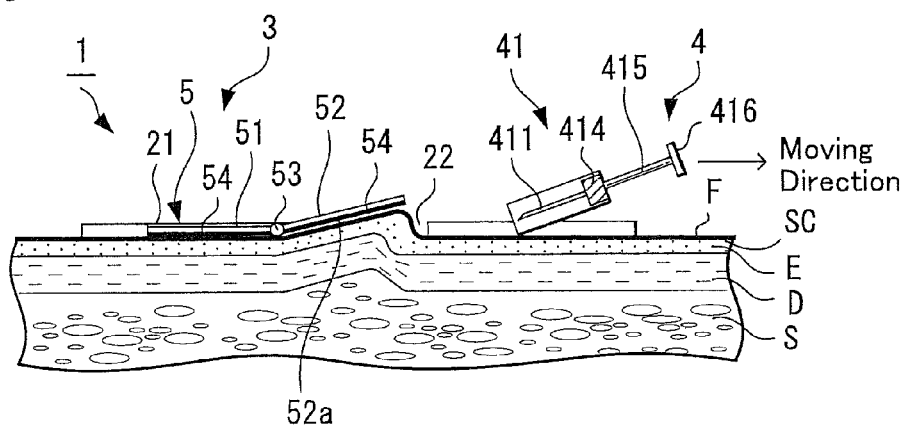

Next, in this state, the mounting member 42 on which the injector 41 is fixedly retained is slided to the rear end direction so as to obtain a state of FIG. 4C, and finally, the adhesion of the adhesive pad 2 and the hinge 5 with respect to the body surface F is released and the puncture device 1 is exfoliated from the body surface F.

In this manner, according to the puncture device 1 of this exemplified embodiment, the puncture operation is carried out in a state in which the skin is uplifted by the hinge 5, so that it is possible to stick the puncture needle 411 certainly into the skin (dermis D) and it is possible to inject the medicinal solution certainly into the dermis D of the skin.

Also, the puncture needle 411 is stuck so as to become approximately a parallel state with respect to the turning piece 52, so that the insertion depth of the puncture needle 411 in the inside of the dermis D becomes long and even in a case in which an impact or the like is added from the outside, the puncture needle 411 during injecting the medical agent can be prevented from dropping out from the dermis D.

Also, the distance from the insertion aperture of the puncture needle 411, which is formed at a boundary portion between the epidermis E and the dermis D to the medical agent releasing aperture which exists at the needlepoint 411a becomes long, so that the medical agent once injected into the dermis D from the medical agent releasing aperture can be prevented from leaking from the insertion aperture to the epidermis E by being flown back [backward].

In addition, it is also possible for the puncture device of this exemplified embodiment to be used in a field of implanting a catheter other than an object in which, as being described above, a medical agent is injected by one-shot. In this case, the catheter is retained with the puncture needle and by leaving the catheter in the skin and taking out only the puncture needle, the catheter is implanted inside the skin. In this manner, by implanting a hollow catheter which has an opening at the implanted portion, it is possible to carry out continuous administration of a medical agent or sampling of the body fluid component. In addition, by implanting a catheter which has a sensor in the implanted portion, it is also possible to carry out measurement of the body component.

In addition, this exemplified embodiment was explained by using exemplified examples in which the puncture needle is always stuck to the dermis D, but it is possible to use the puncture device of the present invention also in case of sticking to an intracutaneous area, a subcutis or further a muscle other than the dermis.

It should be noted that the puncture device of this exemplified embodiment is not limited by the above-mentioned each exemplified embodiment and besides that, it goes without saying that various modifications or changes can be employed for the materials, the constitutions or the like in the region without departing from the configuration of the present invention.

Second Exemplified Embodiment

Next, it will be explained with respect to a second exemplified embodiment of a puncture device of the present invention.

Figure 5:
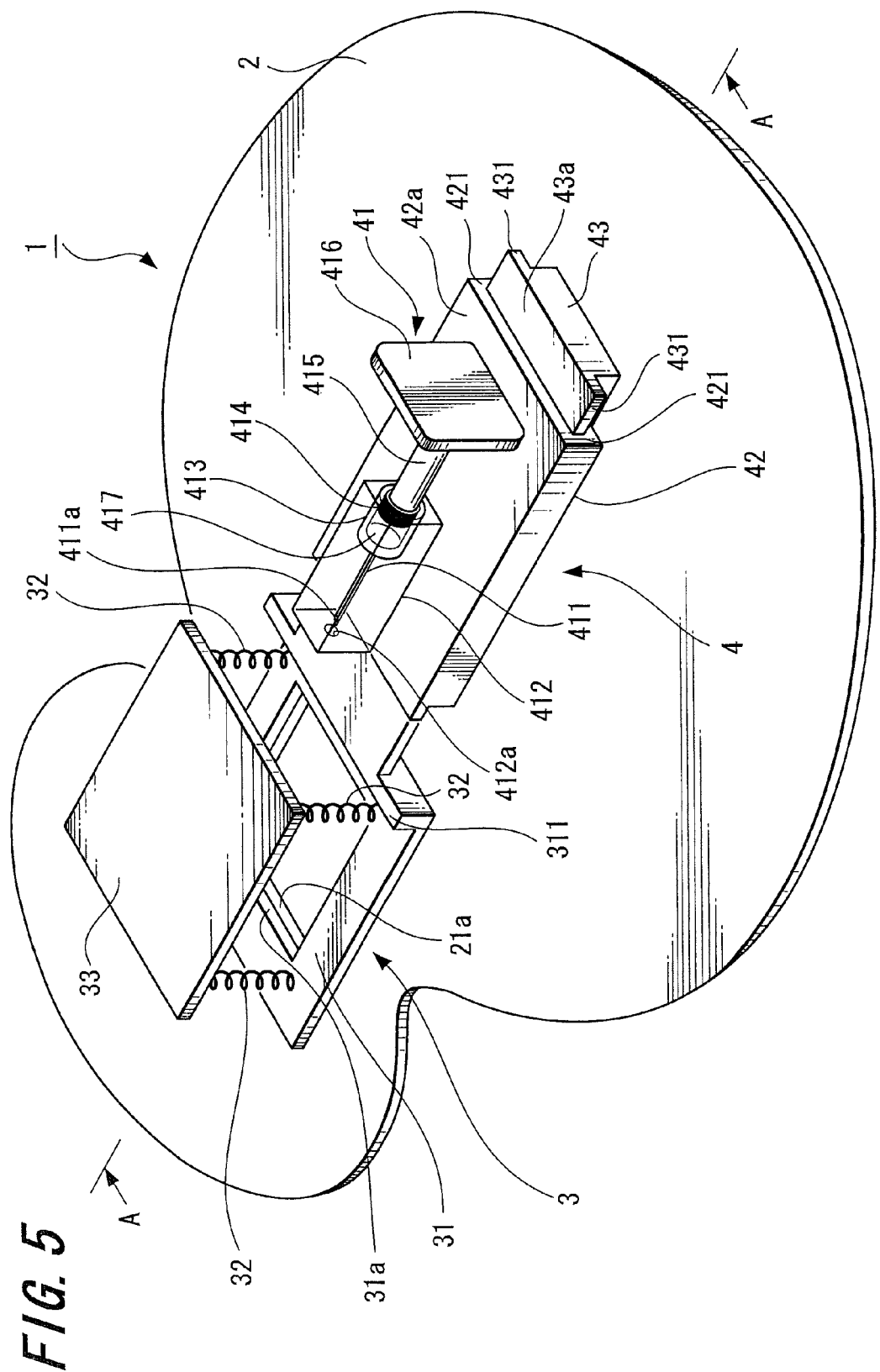
[FIG. 5] A perspective view showing a second exemplified embodiment of a puncture device of the present invention.
Figure 6:
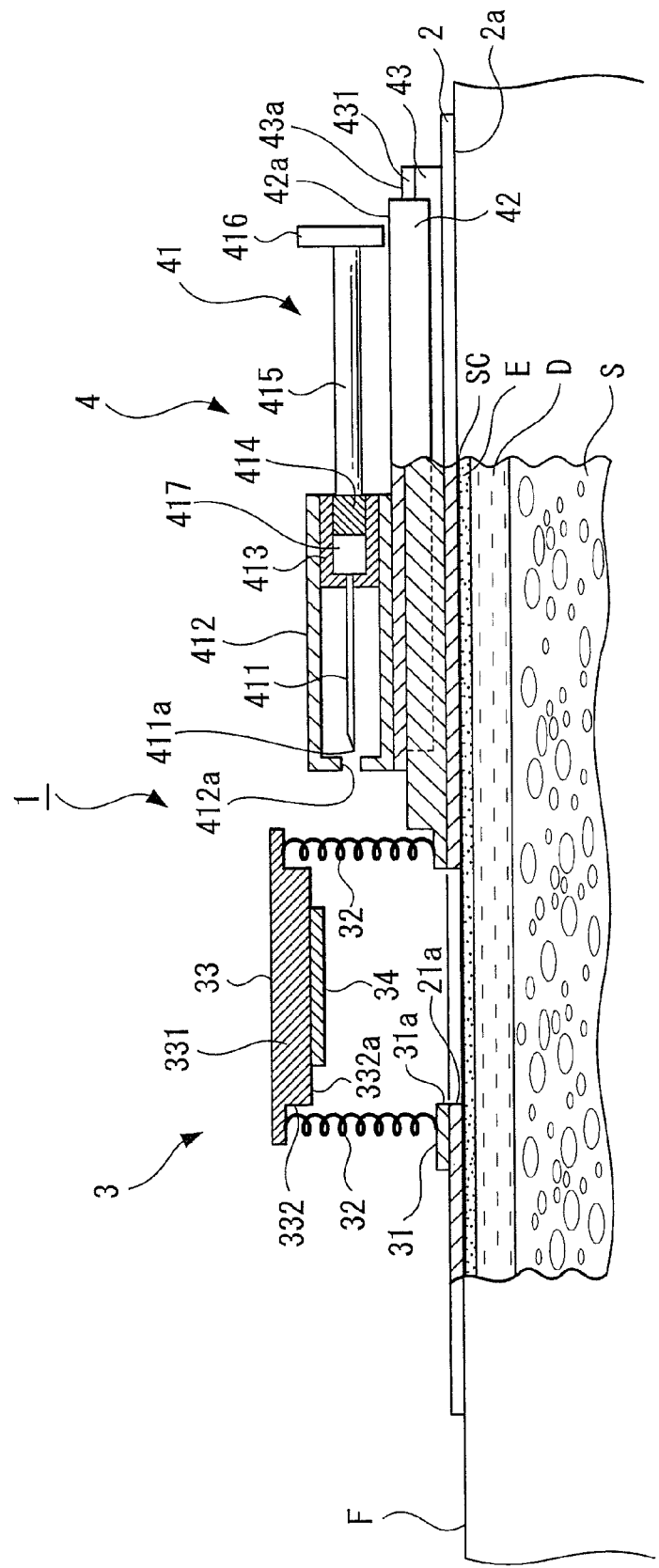
[FIG. 6] A cross-section view by A-A line in FIG. 5.

FIG. 5 is a perspective view showing a second exemplified embodiment of a puncture device of the present invention. FIG. 6 is a cross-section view by A-A line in FIG. 5. Also, FIG. 7A to 7C and FIG. 8A to 8C are diagrams (cross-section views) for explaining usage of the puncture device shown in FIG. 5. It should be noted hereinafter that it will be explained by assuming the right side of FIG. 6 to FIG. 8 to be "rear end" and the left side thereof to be "tip".

As shown in FIG. 5 and FIG. 6, a puncture device 1 showing a second exemplified embodiment of the puncture device of the present invention is constituted by being provided with an adhesive pad 2 which is the fixing portion, a skin deforming means 3 for deforming and uplifting the skin, a puncture needle moving means 4 for retaining a puncture needle 411 to be movable and the like.

The adhesive pad 2 is made to be a plate body having such a shape in which two elliptical plate bodies of different sizes are formed continuously in the lateral direction and, so-called, a wing-like shape is formed.

On the upper surface of the adhesive pad 2, the skin deforming means 3 is arranged on the small ellipse side and the puncture needle moving means 4 is arranged on the large ellipse side thereof.

In this manner, by constituting the area of the side on which the puncture needle moving means 4 is arranged to be large, it is possible to increase stability with respect to the body surface F and to carry out the movement of the puncture needle 411 by means of the puncture needle moving means 4 in a stable state.

There is provided at a position corresponding to the skin deforming means 3 of the adhesive pad 2 with an opening window 21a for contacting a skin bonding member 33 to be described hereinafter of the skin deforming means 3 to the body surface F.

The lower surface of the adhesive pad 2 is made to be a plane 2a for fixing the adhesive pad 2 by being appressed to the body surface F. An adhesion means is provided on this plane 2a and as the adhesion means, it is allowed to apply an adhesive agent on the plane 2a in the form of laminae or it is also allowed to glue a adhesive film of a two-sided tape thereon. It should be noted that a bonding means is not provided on the plane 2a of a position which corresponds to downside of a support board 31. This is because it becomes easy for the skin to be uplifted.

As shown in FIG. 6, the plane 2a of the adhesive pad 2 is fixed on the body surface F by means of an adhesive agent. It should be noted that there are arranged, on the lower side of the body surface F, a stratum corneum SC, an epidermis E including the stratum corneum SC, a dermis D and a subcutis S in the form of laminae.

As the constituent material of such an adhesive pad 2, there can be cited, for example, a soft polymer of flexible polyurethane or the like.

The skin deforming means 3 is constituted by being provided with the support board 31 fixed on the upper surface of the adhesive pad 2, a skin bonding member 33 facing to the support board 31 and a plurality of coil springs 32 or the like which are intervened between the support board 31 and the skin bonding member 33 and are shown as one embodiment of a biasing member biasing the skin bonding member 33.

The support board 31 of the skin deforming means 3 forms approximately a quadrangular frame body and an opening portion 31a thereof is faced to the opening window 21a of the adhesive pad 2. On one side of the support board 31, there is provided on the upper surface thereof with a side surface piece 311 which projects upward and continuously. This side surface piece 311 is made to be continuous with a support member 43 to be described hereinafter of the puncture needle moving means 4.

The skin bonding member 33 is constituted by a main body plate 331 forming approximately a quadrangular plate body and an adhesion protrusion portion 332 which is inserted into the opening portion 31a of the support board 31 and the opening window 21a of the adhesive pad 2. The adhesion protrusion portion 322 of the skin bonding member 33 projects on the lower surface of the main body plate 331 continuously and approximately perpendicularly and has an adhesion surface 332a as a skin fixing plane which is a plane for being fixed on the body surface F.

The adhesion surface 332a of the adhesion protrusion portion 332 is provided with an adhesive film 34 showing one embodiment of the adhesion means and by means of this adhesive film 34, the adhesion surface 332a of the skin bonding member 33 is bonded on the body surface F. For the adhesion means, for example, an adhesive film of a two-sided tape or the like is used.

The plurality of coil springs 32 are provided by four pieces according to this exemplified embodiment (three pieces are shown in FIG. 5) and are arranged so as to connect four corners of the support board 31 and four corners of the skin bonding member 33 respectively. More specifically, the coil springs 32 are set to be all the same length, and one terminals thereof are fixed on the upper surface of the support board 31 and the other terminals thereof are fixed on the lower surface of the main body plate 331 of the skin bonding member 33, respectively. Thereby, it is constituted so as to obtain a state in which the four coil springs 32 support the skin bonding member 33 at upper portion of the support board 31.

Also, the coil springs 32 are made to be so-called compression coil springs which receive compressive loads in the direction of the center axis of the coil. For that reason, a state can be obtained in which owing to these of coil springs 32, the skin bonding member 33 is biased so as to be apart from the upper surface of the support board 31 approximately in the vertical direction.

In this exemplified embodiment, a constitution is employed in which the coil springs 32 are provided by four pieces, but the number of the coil springs 32 is not limited by four and it may be three or less and also, it may be five or more. Also, a constitution is employed in this exemplified embodiment in which compression coil springs are used for the biasing member, but it is not limited by this constitution with respect to the biasing member relating to the present invention and it is possible to apply, for example, a plate spring, an extension spring, a rubber-like elastic body or the like.

In order to apply the extension spring to the skin deforming means relating to the present invention, it is possible to cite, for example, a constitution in which a leg portion for arranging the support board 31 at the upper portion of the adhesive pad 2 is provided, the extension spring is fixed on the lower surface of the support board so as to be hung therefrom and at the same time the other terminal of the extension spring is supported by being fixed to the skin bonding member.

The puncture needle moving means 4 is constituted by an injector 41 mounted with a puncture needle 411, a mounting member 42 for mounting and fixing the injector 41, and a support member 43 for supporting the mounting member 42 to be movable.

The injector 41 is provided with the puncture needle 411, a fixed outer cylinder 412, an internal outer cylinder 413 slidable in the fixed outer cylinder 412, a gasket 414 slidable in the internal outer cylinder 413, and a plunger 415 moving-operating the gasket 414.

The fixed outer cylinder 412 has a cylindrical shape with bottom and is mounted and fixed on the mounting member 42 by means of adhesive agent or the like. Also, there is formed in the vicinity of the central portion of the bottom portion of the fixed outer cylinder 412 with a puncture needle opening 412a for carrying out insertion of the puncture needle 411.

The internal outer cylinder 413 has a cylindrical shape with bottom. Also, the puncture needle 411 is mounted in the vicinity of the central portion of bottom portion.

The needlepoint 411a of the puncture needle 411 is provided so as not to project from the puncture needle opening 412a provided a the fixed outer cylinder 412. More specifically, the puncture needle 411 is located with respect to the fixed outer cylinder 412 such that the needlepoint 411a thereof is positioned on the inner side as compared with the bottom face of the fixed outer cylinder 412 on which the puncture needle opening 412a is provided and also in the vicinity of the puncture needle opening 412a.

By constituting in this manner, the needlepoint 411a of the puncture needle 411 is protected. For that reason, it is possible to prevent a finger or the like from touching the needlepoint 411a of the puncture needle 411 or to prevent the puncture needle 411 from puncturing the finger or the like accidentally, and it is possible to maintain the puncture needle 4 in a clean state. Also, it never happens that the puncture needle 411 directly receives an impact from the outside and it is possible to prevent the puncture needle 411 from being deformed by the impact.

The outer diameter of the puncture needle 411 is a little bit different depending on the use application or the like of the puncture device 1, but it is preferable to select it as around 0.05 to 2 mm and in particular, preferable to select it as around 0.1 to 1.5 mm.

There can be cited, for the constituent material of the puncture needle 411, metal materials such as, for example, stainless steel, aluminum or aluminum alloy, titanium or titanium alloy and the like. Also, the puncture needle 411 is manufactured, for example, by plastic working.

It is possible for the internal outer cylinder 413 to slide in the fixed outer cylinder 412 in a longitudinal direction of the internal outer cylinder 413 by means of the operation of the plunger 415 and when the internal outer cylinder 413 slides, the puncture needle 411 firmly fixed to the internal outer cylinder 413 is taken in and out with respect to the fixed outer cylinder 412 through the puncture needle opening 412a.

For the constituent material of the fixed outer cylinder 412 and the internal outer cylinder 413, there can be cited various kinds of resins such, for example, as polyvinylchloride, polyethylene, polypropylene and the like. It should be noted that the constituent material of the fixed outer cylinder 412 and the internal outer cylinder 413 is desirable to be substantially transparent in order to ensure visibility of the inside.

There is housed, in the internal outer cylinder 413, the gasket 414 constituted by an elastic material.

For the constituent material of the gasket 414, although it is not limited in particular, there can be cited, for example, various kinds of rubber materials such as natural rubber and silicone rubber, various kinds of thermoplastic elastomers of polyurethane series, styrene series and the like or elastic materials of mixtures thereof and the like.

In the space surrounded by the gasket 414 and internal outer cylinder 413, a liquid room 417 is formed and in this liquid room 417, liquid is contained liquid-tightly beforehand.

There can be cited for the liquid, for example, remedy for injection or medicinal solution using a macromolecular substance such as hormone, antibody drug, cytokine, vaccine or the like.

There is interlinked to the gasket 414 the plunger 415 which moving-operate the gasket 414 in the internal outer cylinder 413 in a longitudinal direction.

A plate-like flange 416 is formed integrally at the rear end of the plunger 415. The plunger 415 is operated by depressing this flange 416 with a finger or the like.

The mounting member 42 is formed by a rectangular plate body and there are provided on both the side surfaces of the long side with engagement portions 421, 421. These engagement portions 421, 421 are slidably engaged with engagement convex portions 431, 431 to be described hereinafter of the support member 43. Then, a fixed outer cylinder 412 of the injector 41 is fixed to an upper surface portion 42a of the mounting member 42.

The support member 43 is formed by a rectangular plate body which is set to be thicker than the mounting member 42 and an edge portion on the tip side thereof is made to be continuous with the side surface piece 311 of the support board 31. Thereby, the skin deforming means and the puncture needle moving means 4 are constituted integrally. An firmly-fixing means of an adhesive agent or the like is mounted on a lower surface portion 43b of the support member 43 and as shown in FIG. 6, it is bonded and fixed on the upper surface of the adhesive pad 2.

There are provided on both the side surfaces of the long sides of the support member 43 with engagement convex portions 431, 431. Then, owing to a mechanism that the engagement portions 421, 421 of the mounting member 42 are engaged slidably with these engagement convex portions 431, 431, the mounting member 42 is supported by the support member 43 to be movable.

The upper surface portion 43a of the support member 43 is made to be parallel with respect to the plane of the adhesive pad 2 and the adhesion surface 332a of the skin bonding member 33. For that reason, the mounting member 42 moved along the upper surface portion 43a of the support member 43 is made to move in parallel with respect to the plane of the adhesive pad 2 and the adhesion surface 332a of the skin bonding member 33. Also, an axis center line of the puncture needle 411 mounted on the injector 41 is made to coincide with the moving direction of the mounting member 42.

It is possible for the constituent material of the mounting member 42 and the support member 43 of the puncture needle moving means 4, and of the support board 31 and the skin bonding member 33 of the skin deforming means 3 to cite, for example, various kinds of synthetic resins having appropriate strength such as acrylic resin, ABS resin and the like, but it is not limited by this material and it is also possible to use a metal such as aluminum alloy or the like.

It should be noted as the puncture needle moving means 4 that it is allowed to employ such a constitution wherein an injector having a constitution in which a puncture needle and a syringe are formed as one body configuration is fixed and retained on the mounting member 42. In this case, the length of the puncture needle 411 is adjusted such that the needle-point 411a of the puncture needle 411 can puncture the skin uplifted by the skin deforming means 3 when the mounting member 42 is moved so as to most approach to the skin deforming means 3.

Also, a constitution is employed in this exemplified embodiment in which the injector 41 is provided in the puncture needle moving means 4 and the puncture needle 411 is mounted on the injector thereof, but it is not limited by this constitution and it is allowed to employ, for example, a constitution in which a tube for communicating with the side opposite to the needlepoint 411a of the puncture needle 411 is provided and the other terminal of that tube is made to communicate with an infusion device such as a liquid transmission pump or the like.

Next, it will be explained with respect to the usage (operation) of the puncture device 1 of the second exemplified embodiment.

Figure 7A:
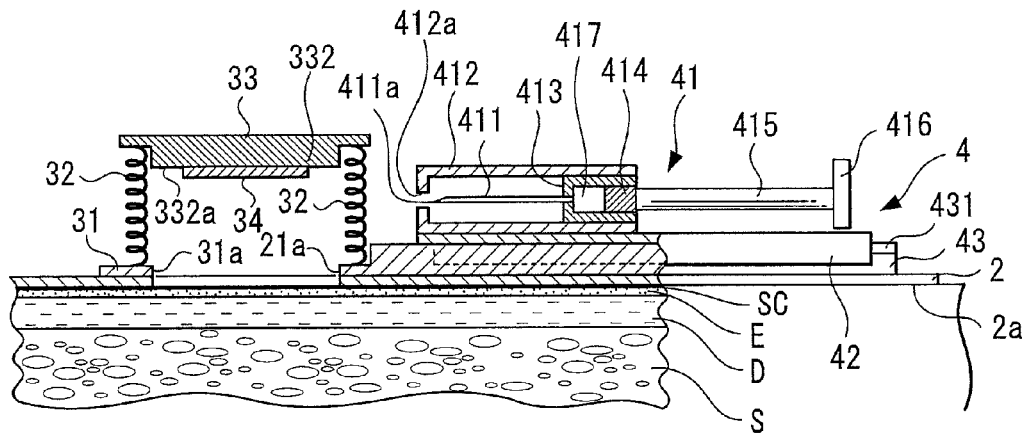
[FIG. 7] First diagrams (cross-section views) for explaining usage of the puncture device shown in FIG. 5.

First, as shown in FIG. 7A, the puncture device 1 is mounted on a predetermined position of the body surface F. At that time, the puncture device 1 is bonded and fixed on the body surface F by means of an adhesive film provided on the plane 2a which is the lower surface of the adhesive pad 2.

Figure 7B:
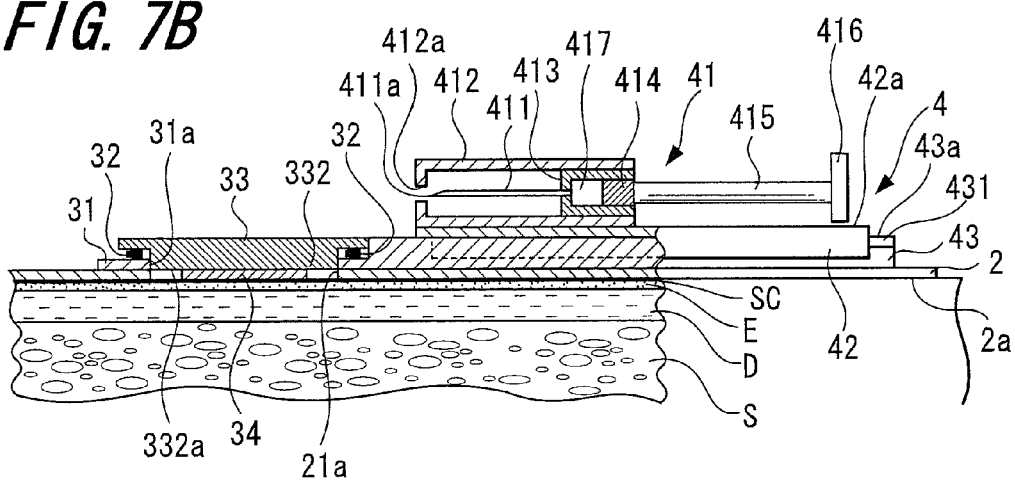

Next, as shown in FIG. 7B, the skin bonding member 33 is depressed downward by a finger so as to compress the four coil springs 32. Thereby, the adhesion protrusion portion 322 of the skin bonding member 33 is inserted into the opening portion 31a of the support board 31 and the opening window 21a of the adhesive pad 2, and the adhesion surface 322a of the adhesion protrusion portion 322 is bonded to the body surface F by the adhesive film 34. It should be noted that it is allowed for the puncture device of the present invention to employ a constitution in which the coil springs 32 are latched in a state of being compressed and the skin bonding member 33 is inserted into the opening window 21a beforehand. In this case, the skin bonding member 33 is bonded to the body surface concurrently when the puncture device 1 is bonded and fixed on a predetermined position of the body surface F.

Figure 7C:
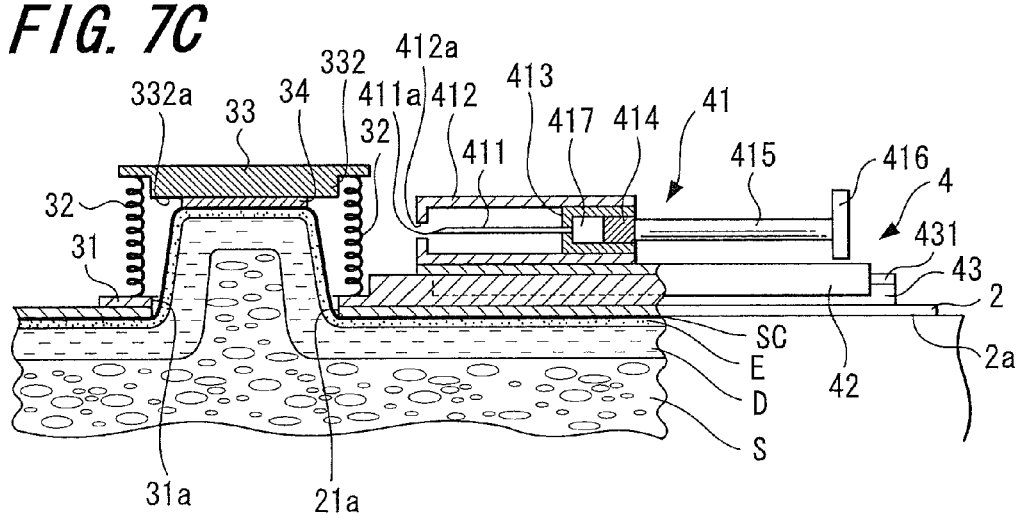

Next, as shown in FIG. 7C, the finger depressing the skin bonding member 33 is released. Thereby, the skin bonding member 33 is biased by the spring force of the four coil springs 32 and is moved upward.

Concurrently with this, the skin bonded to the adhesion surface 322a as the skin fixing plane of the skin bonding member 33 is pulled upward. More specifically, the epidermis E including the stratum corneum SC, the dermis D and the subcutis S are pulled upward respectively and the skin is uplifted to the vertical direction with respect to the body surface F. At that time, the dermis D of the uplifted skin or the like is made to be in a state approximately parallel with the adhesion surface 322a of the skin bonding member 33.

More specifically, depending on a fact that the skin is deformed and uplifted, the position of the plane 2a of the adhesive pad 2 which is the fixing portion and the position of the adhesion surface 322a as the skin fixing plane become different in the height direction, a step portion is formed there-between and the puncture needle 411 is stuck into the step portion thereof.

Further, the four coil springs 32 are set to be a predetermined length, so that it becomes a state in which the height of the dermis D of the skin pulled up by the skin bonding member 33 and the height by which the puncture needle 411 of the puncture needle moving means 4 is located will coincide with each other.

Next, the mounting member 42 on which the injector 41 is fixedly retained is slided to the tip direction. More specifically, the bottom face of the fixed outer cylinder 412 and the side surface of the uplifted skin are made to be adjacent and the needlepoint 411a of the puncture needle 411 is made to approach to the side surface of the uplifted skin.

Next, the plunger 415 is operated by depressing the flange 416 with a finger or the like and the internal outer cylinder 413 is moved to the tip direction while being slided in the fixed outer cylinder 412.
Thereby, the puncture needle 411 firmly fixed on the internal outer cylinder 413 is inserted into a puncture region (step portion) from the puncture needle opening 412a and as shown in FIG. 8A, the needlepoint 411a of the puncture needle 411 is stuck in parallel with respect to the dermis D by bypassing the epidermis E including the stratum corneum SC.

The plunger 415 is operated by further depressing the flange 416 with a finger or the like from that state and the gasket 414 is moved to the tip direction while sliding it in the internal outer cylinder 413. Thereby, as shown in FIG. 8B, the liquid contained in the liquid room 417 is injected from the needlepoint 411a of the puncture needle 411 to the dermis D.

After the liquid is injected into the dermis D and thereafter, the mounting member 42 is moved to the rear end direction and the puncture needle 411 is pulled out from the uplifted skin.

Further, the plunger 415 is moved to the rear end direction and the puncture needle 411 is housed in the fixed outer cylinder 412 through the puncture needle opening 412a.

Next, in this state, the mounting member 42 on which the injector 41 is fixedly retained is slided to the rear end direction so as to obtain a state of FIG. 8C, and finally, the adhesion of the adhesive pad 2 and the skin bonding member 33 with respect to the body surface F is released and the puncture device 1 is exfoliated from the body surface F.

Third Exemplified Embodiment

Next, it will be explained with respect to a third exemplified embodiment of a puncture device of the present invention.

Figure 10:
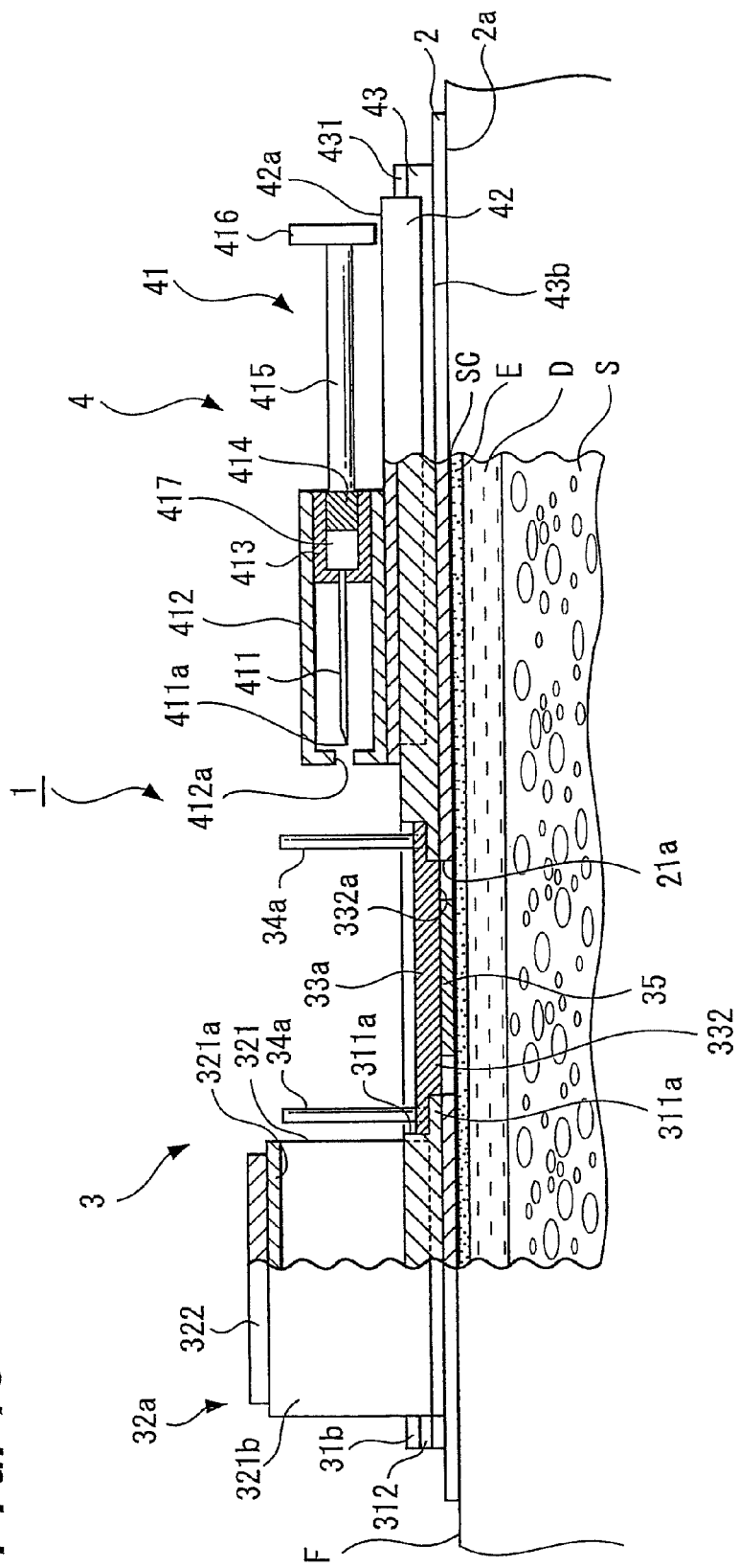
[FIG. 10] A cross-section view by A-A line in FIG. 9.

FIG. 9 is a perspective view showing a third exemplified embodiment of a puncture device of the present invention. FIG. 10 is a cross-section view by A-A line in FIG. 9. Also, FIGS. 11A, 11B and FIGS. 12A to 12C are diagrams (cross-section views) for explaining usage of the puncture device shown in FIG. 9. It should be noted hereinafter that it will be explained by assuming the right side of FIG. 10 to FIG. 12 to be "rear end" and the left side thereof to be "tip".

As shown in FIG. 9 and FIG. 10, a puncture device 1 showing a third exemplified embodiment of a puncture device of the present invention is constituted by being provided with an adhesive pad 2 which is a fixing portion, a skin deforming means 3 for deforming and uplifting the skin, a puncture needle moving means 4 for retaining a puncture needle 411 to be movable and the like.

The adhesive pad 2 is made to be a plate body having such a shape in which two elliptical plate bodies of different sizes are formed continuously in the lateral direction and, so-called, a wing-like shape is formed.

On the upper surface of the adhesive pad 2, the skin deforming means 3 is arranged on the small ellipse side and the puncture needle moving means 4 is arranged on the large ellipse side thereof. In this manner, by constituting the area of the side on which the puncture needle moving means 4 is arranged to be large, it is possible to increase stability with respect to the body surface F and to carry out the movement of the puncture needle 411 by means of the puncture needle moving means 4 in a stable state.

There is provided at a position corresponding to the skin deforming means 3 of the adhesive pad 2 with an opening window 21a for contacting a skin bonding member 33a to be described hereinafter of the skin deforming means 3 to the body surface F.

The lower surface of the adhesive pad 2 is made to be a plane 2a for fixing the adhesive pad 2 by being appressed to the body surface F. An adhesion, means is provided on this plane 2a and as the adhesion means, it is allowed to apply an adhesive agent on the plane 2a in the form of laminae or it is also allowed to glue a adhesive film of a two-sided tape thereon. It should be noted that a bonding means is not provided on the plane 2a of a position which corresponds to downside of a base member 31b. This is because it becomes easy for the skin to be uplifted.

As shown in FIG. 10, the plane 2a of the adhesive pad 2 is fixed on the body surface F by means of an adhesive agent. It should be noted that there are arranged, on the lower side of the body surface F, a stratum corneum SC, an epidermis E including the stratum corneum SC, a dermis D and a subcutis S in the form of laminae.

As the constituent material of such an adhesive pad 2, there can be cited, for example, a soft polymer of flexible polyurethane or the like.

The skin deforming means 3 is constituted by being provided with the base member 31b fixed on the upper surface of the adhesive pad 2, a magnet member 32a supported by this base member 31b to be movable, a skin bonding member 33a pulled by the magnetic force of the magnet member 32a so as to move and the like.

The base member 31b of the skin deforming means 3 is formed by approximately a rectangular plate body and one of the side surfaces of the short sides thereof is made to be continuous with a support member 43 to be described hereinafter of the puncture needle moving means 4. As shown in FIG. 10 and the like, there is provided on the side of the puncture needle moving means 4 of the base member 31b with a quadrangular through-hole 311 passing through the upper and lower surfaces thereof, and this through-hole 311 faces to the opening window 21a of the adhesive pad 2.

There is formed on the inner surface of the through-hole 311 with a step portion 311a which is continuous in the circumferential direction thereof. According to this step portion 311a, the through-hole 311 is set such that the opening portion of the lower surface side becomes smaller than the opening portion of the upper surface side.

Guide pins 34a showing one embodiment of a guide member for guiding the movement of the skin bonding member 33a are fixed at the four corners of the step portion 311a of the through-hole 311 respectively. The four guide pins 34a are extended approximately perpendicularly toward the upper portion respectively and by these guide pins 34a, the skin bonding member 33a is guided approximately in the perpendicular direction with respect to the base member 31b.

Also, as shown in FIG. 9 and the like, there are provided on both the side surfaces of the long side of the base member 31b with guide grooves 312, 312 (only one thereof is shown in FIG. 9). Slide rails 321c, 321c to be described hereinafter of the magnet member 32a are engaged with these guide grooves 312, 312 slidably, respectively.

The magnet member 32a is constituted by a moving table 321 supported by the base member 31b to be movable slidably and a magnet 322 mounted on this moving table 321.

The moving table 321 of the magnet member 32a is composed of a mounting plate 321a formed by approximately a quadrangular plate body, a pair of side surface plates 321b, 321b which are extended to the lower side continuously on the two facing sides of this mounting plate 321a respectively and the like.

There is mounted on the upper surface of the mounting plate 321a with the magnet 322 forming a flat plate body by means of firmly-fixing means of adhesive agent or the like. This magnet 322 is arranged such that pulling force is operated with respect to the skin bonding member 33a each other.

In this manner, in a state in which the skin bonding member 33a is pulled by means of the magnet 322 by mounting the magnet 322 on the upper surface of the mounting plate 321, it never happens that the skin bonding member 33a will be directly attached firmly to the magnet 322 thereof and it is possible to easily carry out changeover between a state in which the skin bonding member 33a is pulled and a state without being pulled. However, it is also possible for the puncture device 1 of the present invention to be made as a constitution in which the skin bonding member is pulled and directly attached firmly to the magnet.

There are provided at the lower end portion of the pair of side surface plates 321b, 321b with slide rails 321c, 321c (only one thereof is shown in FIG. 9) respectively. Then, by engaging these slide rails 321c, 321c slidably with the guide grooves 312, 312 of the base member 31b, the magnet member 32a having the moving table 321 is supported on the base member 31b to be movable slidably. More specifically, the magnet member moving means for moving the magnet member 32a is constituted by the slide rails 321c, 321c of the moving table 321 and the guide grooves 312, 312 of the base member 31b.

As shown in FIG. 9, FIG. 10 and the like, the skin bonding member 33a is constituted by the main body plate 331 forming approximately a quadrangular plate body and an adhesion protrusion portion 332 inserted into the through-hole 311 of the base member 31b and the opening window 21a of the adhesive pad 2. This skin bonding member 33a has around reasonable degree of strength for not being deformed elastically and also is formed by a magnetic material by which pulling force is operated with respect to the magnet 322 each other. It is possible for the constituent material of such a skin bonding member 33a to cite, for example, iron, nickel, cobalt or the like.

There are provided on the main body plate 331 of the skin bonding member 33a with guide openings 331a for making the respective guide pins 34a fixed on the base member 31b to pass there-through. Thereby, the skin bonding member 33a is guided in the direction to which the four guide pins 34a are extended, in other words, approximately in the perpendicular direction with respect to the plane of the base member 31b.

The adhesion protrusion portion 322 of the skin bonding member 33a projects on the lower surface of the main body plate 331 continuously and approximately perpendicularly and has an adhesion surface 332a as a skin fixing plane which is a plane for being fixed on the body surface F. The adhesion surface 332a of the adhesion protrusion portion 332 is attached with adhesive film 35 showing one embodiment of the adhesion means. Thereby, the adhesion surface 332a of the skin bonding member 33a is bonded on the body surface F. For the adhesion means, for example, an adhesive film of a two-sided tape or the like is used.

In this exemplified embodiment, the number of the guide pins 34a guiding the movement of the skin bonding member 33a is set to be four, but the number thereof is not limited by this and it is possible to set the number of the guide pins properly in consideration of the shape of the skin bonding member or the like in order to guide the movement of the skin bonding member thereof stably.

The puncture needle moving means 4 is constituted by an injector 41 mounted with a puncture needle 411, a mounting member 42 for mounting and fixing the injector 41, and a support member 43 for supporting the mounting member 42 to be movable.

The injector 41 is provided with the puncture needle 411, a fixed outer cylinder 412, an internal outer cylinder 413 slidable in the fixed outer cylinder 412, a gasket 414 slidable in the internal outer cylinder 413, and a plunger 415 moving-operating the gasket 414.

The fixed outer cylinder 412 has a cylindrical shape with bottom and is mounted and fixed on the mounting member 42 by means of adhesive agent or the like. Also, there is formed in the vicinity of the central portion of the bottom portion of the fixed outer cylinder 412 with a puncture needle opening 412a for carrying out insertion of the puncture needle 411.

The internal outer cylinder 413 has a cylindrical shape with bottom. Also, the puncture needle 411 is mounted in the vicinity of the central portion of the bottom portion.

The needlepoint 411a of the puncture needle 411 is provided so as not to project from the puncture needle opening 412a provided at the fixed outer cylinder 412. More specifically, the puncture needle 411 is located with respect to the fixed outer cylinder 412 such that the needlepoint 411a thereof is positioned in the inner side as compared with the bottom face of the fixed outer cylinder 412 on which the puncture needle opening 412a is provided and also in the vicinity of the puncture needle opening 412a.

By constituting in this manner, the needlepoint 411a of the puncture needle 411 is protected. For that reason, it is possible to prevent a finger or the like from touching the needlepoint 411a of the puncture needle 411 or to prevent the puncture needle 411 from puncturing the finger or the like accidentally, and it is possible to maintain the puncture needle 411 in a clean state. Also, it never happens that the puncture needle 411 directly receives an impact from the outside and it is possible to prevent the puncture needle 411 from being deformed by the impact.

The outer diameter of the puncture needle 411 is a little bit different depending on the use application or the like of the puncture device 1, but it is preferable to select it as around 0.05 to 2 mm and in particular, preferable to select it as around 0.1 to 1.5 mm.

There can be cited, for the constituent material of the puncture needle 411, metal materials such as, for example, stainless steel, aluminum or aluminum alloy, titanium or titanium alloy and the like. Also, the puncture needle 411 is manufactured, for example, by plastic working.

It is possible for the internal outer cylinder 413 to slide in the fixed outer cylinder 412 in a longitudinal direction of the internal outer cylinder 413 by means of the operation of the plunger 415 and when the internal outer cylinder 413 slides, the puncture needle 411 firmly fixed to the internal outer cylinder 413 is taken in and out with respect to the fixed outer cylinder 412 through the puncture needle opening 412a.

For the constituent material of the fixed outer cylinder 412 and the internal outer cylinder 413, there can be cited various kinds of resins such, for example, as polyvinylchloride, polyethylene, polypropylene and the like. It should be noted that the constituent material of the fixed outer cylinder 412 and the internal outer cylinder 413 is desirable to be substantially transparent in order to ensure visibility of the inside.

There is housed, in the internal outer cylinder 413, the gasket 414 constituted by an elastic material.

For the constituent material of the gasket 414, although it is not limited in particular, there can be cited, for example, various kinds of rubber materials such as natural rubber and silicone rubber, various kinds of thermoplastic elastomers of polyurethane series, styrene series and the like or elastic materials of mixtures thereof and the like.

In the space surrounded by the gasket 414 and internal outer cylinder 413, a liquid room 417 is formed and in this liquid room 417, liquid is contained liquid-tightly beforehand.

There can be cited for the liquid, for example, remedy for injection or medicinal solution using a macromolecular substance such as hormone, antibody drug, cytokine, vaccine or the like.

There is interlinked to the gasket 414 the plunger 415 which moving-operate the gasket 414 in the internal outer cylinder 413 in a longitudinal direction.

A plate-like flange 416 is formed integrally at the rear end of the plunger 415. The plunger 415 is operated by depressing this flange 416 with a finger or the like.

The mounting member 42 is formed by a rectangular plate body and there are provided on both the side surfaces of the long side with engagement portions 421, 421. These engagement portions 421, 421 are slidably engaged with engagement convex portions 431, 431 to be described hereinafter of the support member 43. Then, a fixed outer cylinder 412 of the injector 41 is fixed to an upper surface portion 42a of the mounting member 42.

The support member 43 is formed by a rectangular plate body which is set to be thicker than the mounting member 42 and an edge portion on the tip side thereof is made to be continuous with one side surface of the short sides of the base member 31b. Thereby, the skin deforming means and the puncture needle moving means 4 are constituted integrally. An firmly-fixing means of an adhesive agent or the like is mounted on a lower surface portion 43b of the support member 43 and as shown in FIG. 10, it is bonded and fixed on the upper surface of the adhesive pad 2.

There are provided on both the side surfaces of the long sides of the support member 43 with engagement convex portions 431, 431. Then, owing to a mechanism that the engagement portions 421, 421 of the mounting member 42 are engaged slidably with these engagement convex portions 431, 431, the mounting member 42 is supported by the support member 43 to be movable.

The upper surface portion 43a of the support member 43 is made to be parallel with respect to the plane of the adhesive pad 2 and the adhesion surface 332a of the skin bonding member 33a. For that reason, the mounting member 42 moved along the upper surface portion 43a of the support member 43 is made to move in parallel with respect to the plane of the adhesive pad 2 and the adhesion surface 332a of the skin bonding member 33a. Also, an axis center line of the puncture needle 411 mounted on the injector 41 is made to coincide with the moving direction of the mounting member 42.

It is possible for the constituent material of the mounting member 42 and the support member 43 of the puncture needle moving means 4, and of the base member 31b and the moving table 321 of the skin deforming means 3 to cite, for example, various kinds of synthetic resins having appropriate strength such as acrylic resin, ABS resin and the like, but it is not limited by this material and it is also possible to use a metal such as aluminum alloy or the like.

It should be noted as the puncture needle moving means 4 that it is allowed to employ such a constitution wherein an injector having a constitution in which a puncture needle and a syringe are formed as one body configuration is fixed and retained on the mounting member 42. In this case, the length of the puncture needle 411 is adjusted such that the needle-point 411a of the puncture needle 411 can puncture the skin uplifted by the skin deforming means 3 when the mounting member 42 is moved so as to most approach to the skin deforming means 3.

Also, a constitution is employed in this exemplified embodiment in which the injector 41 is provided in the puncture needle moving means 4 and the puncture needle 411 is mounted on the injector thereof, but it is not limited by this constitution and it is allowed to employ, for example, a constitution in which a tube for communicating with the side opposite to the needlepoint 411a of the puncture needle 411 is provided and the other terminal of that tube is made to communicate with an infusion device such as a liquid transmission pump or the like.

Next, it will be explained with respect to the usage (operation) of the puncture device 1 of the third exemplified embodiment.

Figure 11A:
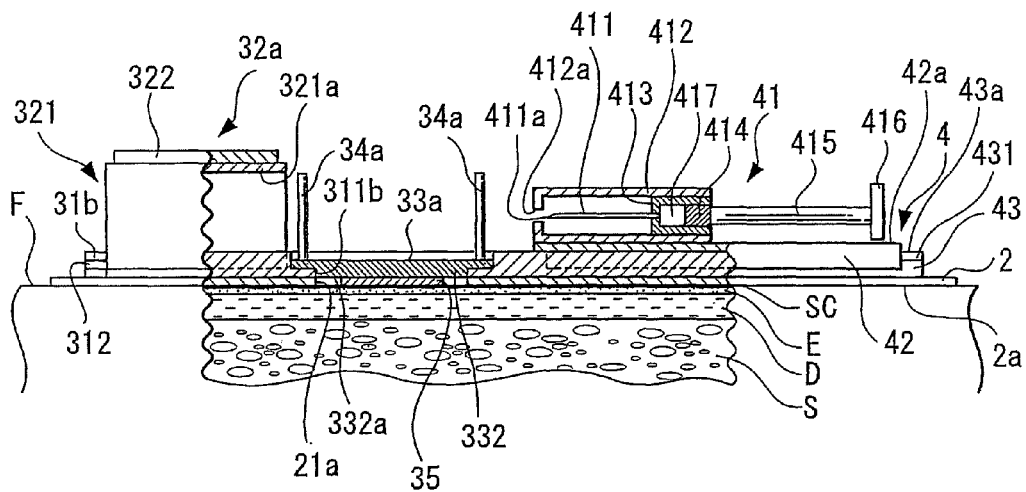
[FIG. 11] First diagrams (cross-section views) for explaining usage of the puncture device shown in FIG. 9.

First, as shown in FIG. 11A, the puncture device 1 in which the magnet member 32a is arranged on the tip side of the base member 31b beforehand is mounted on a predetermined position of the body surface F. At that time, the puncture device 1 is bonded and fixed on the body surface F by means of an adhesive film provided on the plane 2a which is the lower surface of the adhesive pad 2.

Next, the skin bonding member 33a is depressed downward and the adhesion surface 322a of the skin bonding member 33a is bonded to the body surface F by means of the adhesive film 35.

Figure 11B:
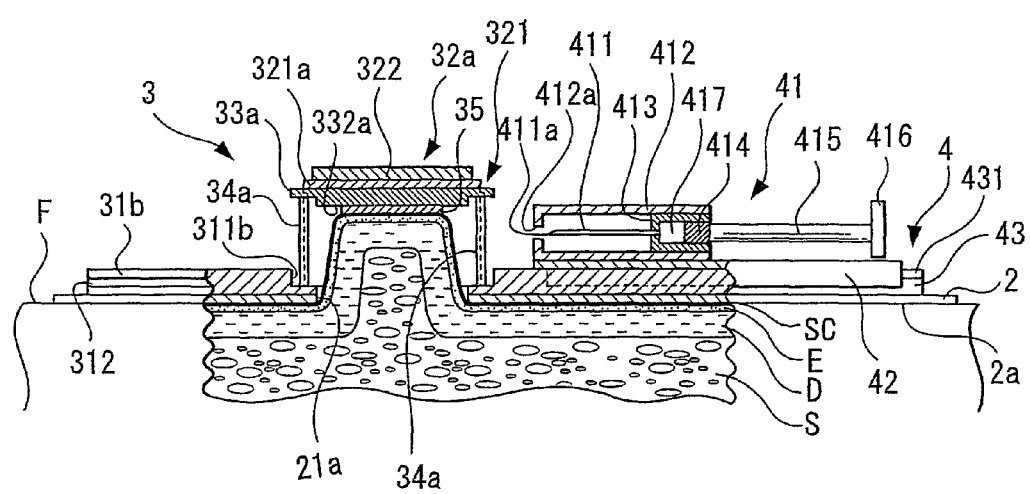

Subsequently, as shown in FIG. 11B, the magnet member 32a of the skin deforming means 3 is moved slidably and the magnet 322 of the magnet member 32a is made to face to the skin bonding member 33a. Thereby, the skin bonding member 33a is pulled by the magnet 322, guided by the four pins 34a and moved upward. Then, it is retained in a state of being contacted to the mounting plate 321a of the moving table 321.

Concurrently with this, the skin bonded to the adhesion surface 332a of the skin bonding member 33a is pulled upward. More specifically, the epidermis E including the stratum corneum SC, the dermis D and the subcutis S are pulled upward respectively and the skin is uplifted to the vertical direction with respect to the body surface F. At that time, the dermis D of the uplifted skin or the like is made to be in a state approximately parallel with the adhesion surface 322a of the skin bonding member 33a.

More specifically, depending on a fact that the skin is deformed and uplifted, the position of the plane 2a of the adhesive pad 2, which is the fixing portion and the position of the adhesion surface 322a as the skin fixing plane become different in the height direction, a step portion is formed there-between and the puncture needle 411 is stuck into the step portion thereof.

Further, the height from the body surface F to the mounting plate 321a of the moving table 321 is set to be a predetermined height, so that it becomes a state in which the height of the dermis D of the skin pulled up by the skin bonding member 33 and the height by which the puncture needle 411 of the puncture needle moving means 4 is located will coincide with each other.

Next, the mounting member 42 on which the injector 41 is fixedly retained is slid to the tip direction. More specifically, the bottom face of the fixed outer cylinder 412 and the side surface of the uplifted skin are made to be adjacent and the needlepoint 411a of the puncture needle 411 is made to approach to the side surface of the uplifted skin.

Figure 12A:
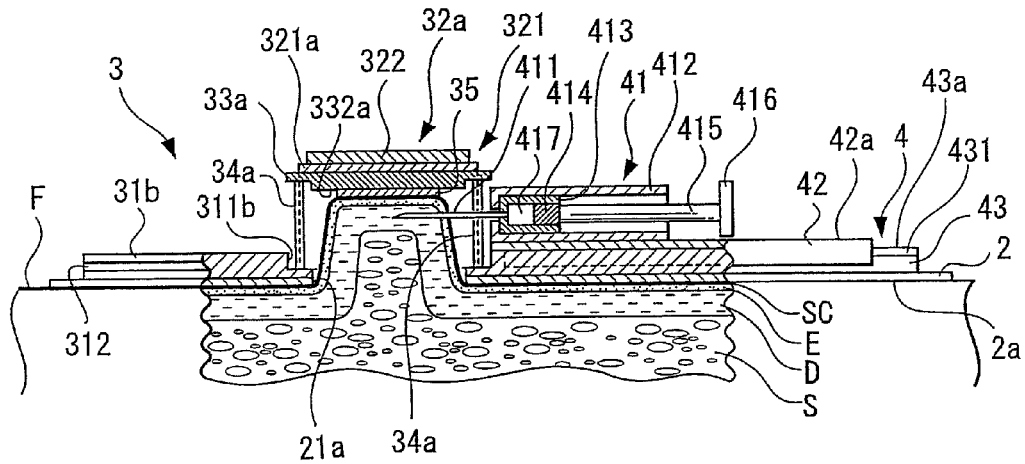
[FIG. 12] Second diagrams (cross-section views) for explaining usage of the puncture device shown in FIG. 9.

Next, the plunger 415 is operated by depressing the flange 416 with a finger or the like and the internal outer cylinder 413 is moved to the tip direction while being slid in the fixed outer cylinder 412. Thereby, the puncture needle 411 firmly fixed on the internal outer cylinder 413 is inserted into a puncture region (step portion) from the puncture needle opening 412a and as shown in FIG. 12A, the needlepoint 411a of the puncture needle 411 is stuck in parallel with respect to the dermis D by bypassing the epidermis E including the stratum corneum SC.

Figure 12B:
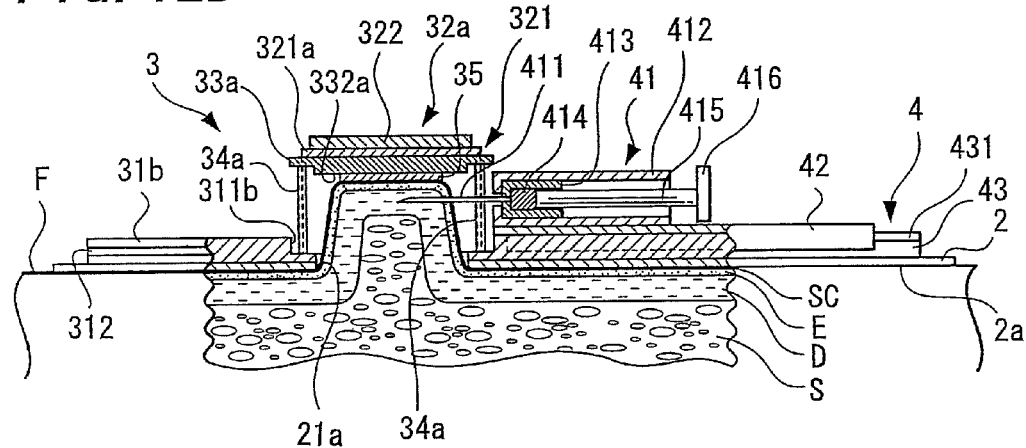

The plunger 415 is operated by further depressing the flange 416 with a finger or the like from that state and the gasket 414 is moved to the tip direction while sliding it in the internal outer cylinder 413. Thereby, as shown in FIG. 12B, the liquid contained in the liquid room 417 is injected from the needlepoint 411a of the puncture needle 411 to the dermis D.

After the liquid is injected into the dermis D and thereafter, the mounting member 42 is moved to the rear end direction and the puncture needle 411 is pulled out from the uplifted skin.

Further, the plunger 415 is moved to the rear end direction and the puncture needle 411 is housed in the fixed outer cylinder 412 through the puncture needle opening 421a.

Figure 12C:
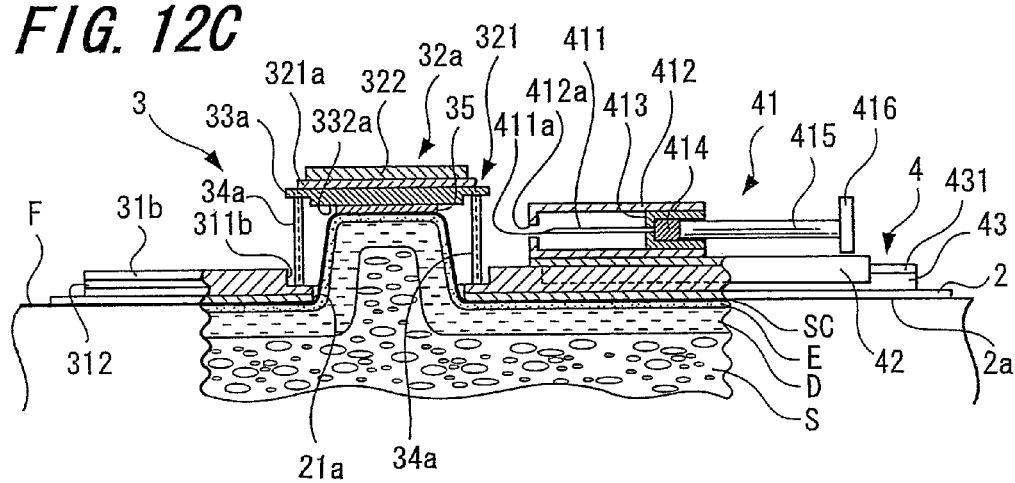

Next, maintaining this state, the mounting member 42 on which the injector 41 is fixedly retained is slid to the rear end side and it is made to be a state of FIG. 12C and thereafter, the magnet member 32a is moved slidably to the tip side and the uplifted skin is made to return to the original state. Then, finally, the adhesion of the adhesive pad 2 and the skin bonding member 33a with respect to the body surface F is released and the puncture device 1 is exfoliated from the body surface F.

In this exemplified embodiment, a constitution is employed wherein a state in which the skin bonding member 33a is pulled and a state without being pulled are changed over by slidably moving the magnet member 32a, but it is not limited by this configuration and it is allowed to employ, for example, a constitution wherein a state in which the skin bonding member 33a is pulled and a state without being pulled are changed over by arranging an electromagnet at a position facing to the skin bonding member 33a and by operating it for the energization thereof.

As explained above, according to the puncture device of this exemplified embodiment, it is possible in case of, for example, puncturing the dermis D, to pull up the dermis D of the skin to an equivalent height as the puncture needle by uplifting the skin by means of the skin deforming means and at the same time, it is possible to make the axis center line of the puncture needle thereof and the direction to which the dermis D layer is extended to be approximately in parallel. As a result thereof, it is possible to insert the puncture needle into the dermis D certainly and deeply, and even in a case in which a impact or the like is added from the outside, it is possible to prevent the puncture needle from dropping out easily from the dermis D during injecting a medical agent.

Further, it is possible to insert the puncture needle into the dermis D deeply, so that it becomes possible to lengthen the distance from the medical agent releasing aperture which exists at the needlepoint of the puncture needle to the epidermis E and the body surface F, so that it is possible to prevent the medical agent injected from the medical agent releasing aperture to the dermis D from flowing back [backward] and permeating the epidermis E or from leaking to the outside of the body surface F. Accordingly, it is possible to inject the medical agent into the dermis D certainly.

Also, the skin deforming means and the puncture needle moving means are constituted integrally by being continuous, so that it is possible when carrying out the assembling operation to omit an operation such as position adjustment or the like of the puncture needle moving means with respect to the skin deforming means and it is possible to improve workability on an occasion of assembling. Further, it is possible to accurately set the position of the puncture needle with respect to the skin to be uplifted and it is possible to stick the puncture needle to the dermis D certainly.

It is also possible for the puncture device of the present invention to be used for implanting a cannula other than an object in which, as being described so far, a medical agent is injected by one-shot. In this case, the cannula is retained with the puncture needle and by leaving the cannula after the puncture and taking out only the puncture needle, the cannula is implanted inside the skin. By implanting a hollow cannula which has an opening at the implanted portion, it is possible to use it for an object of continuous administration of a medical agent or for an object of sampling of the body fluid component. In addition, by implanting a catheter which has a sensor in the implanted portion, it is also possible to carry out measurement of the body component.

Fourth Exemplified Embodiment

Next, it will be explained with respect to a fourth exemplified embodiment of a puncture device of the present invention.

Figure 13:
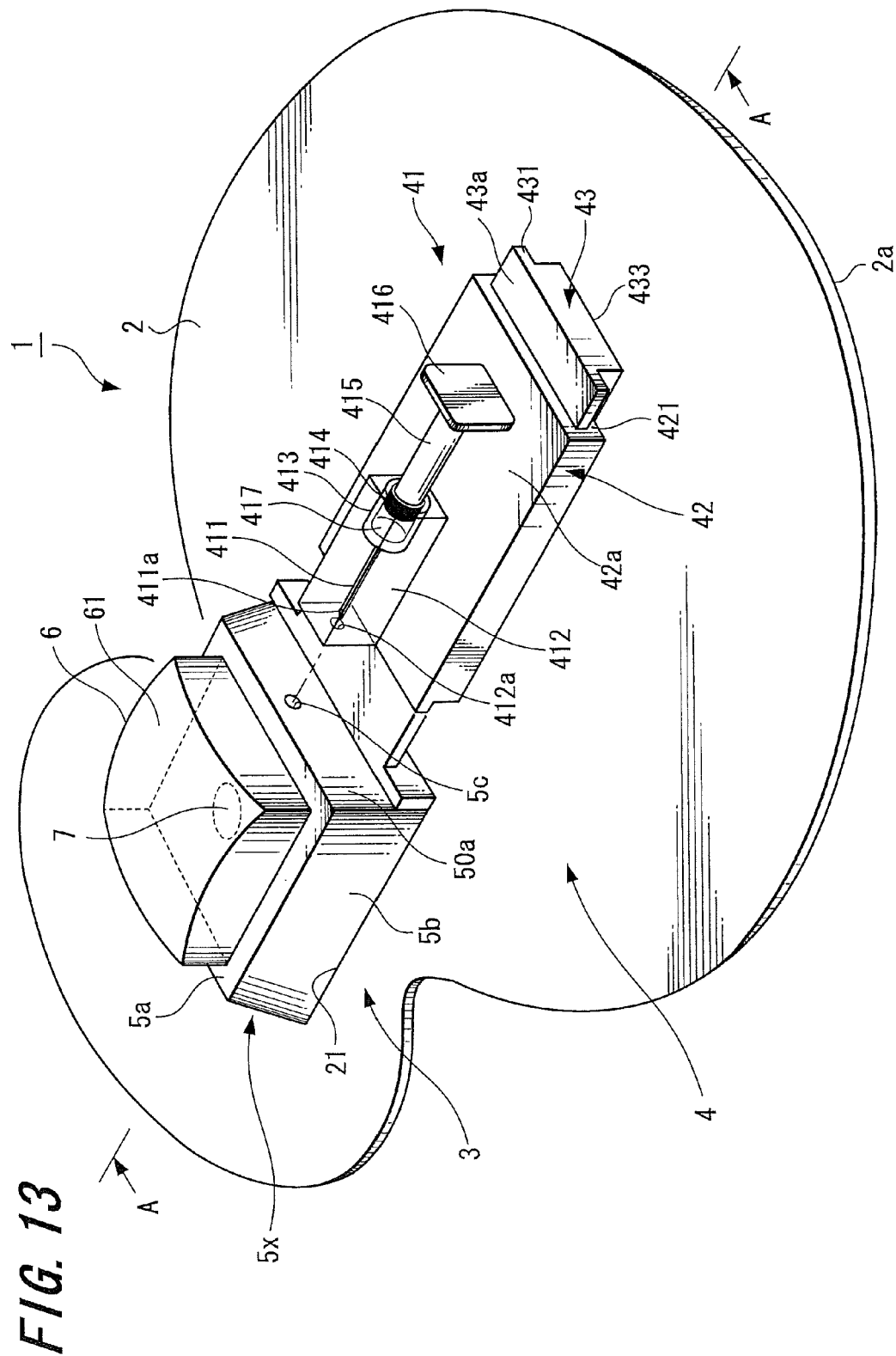
[FIG. 13] A perspective view showing a fourth exemplified embodiment of a puncture device of the present invention.
Figure 14:
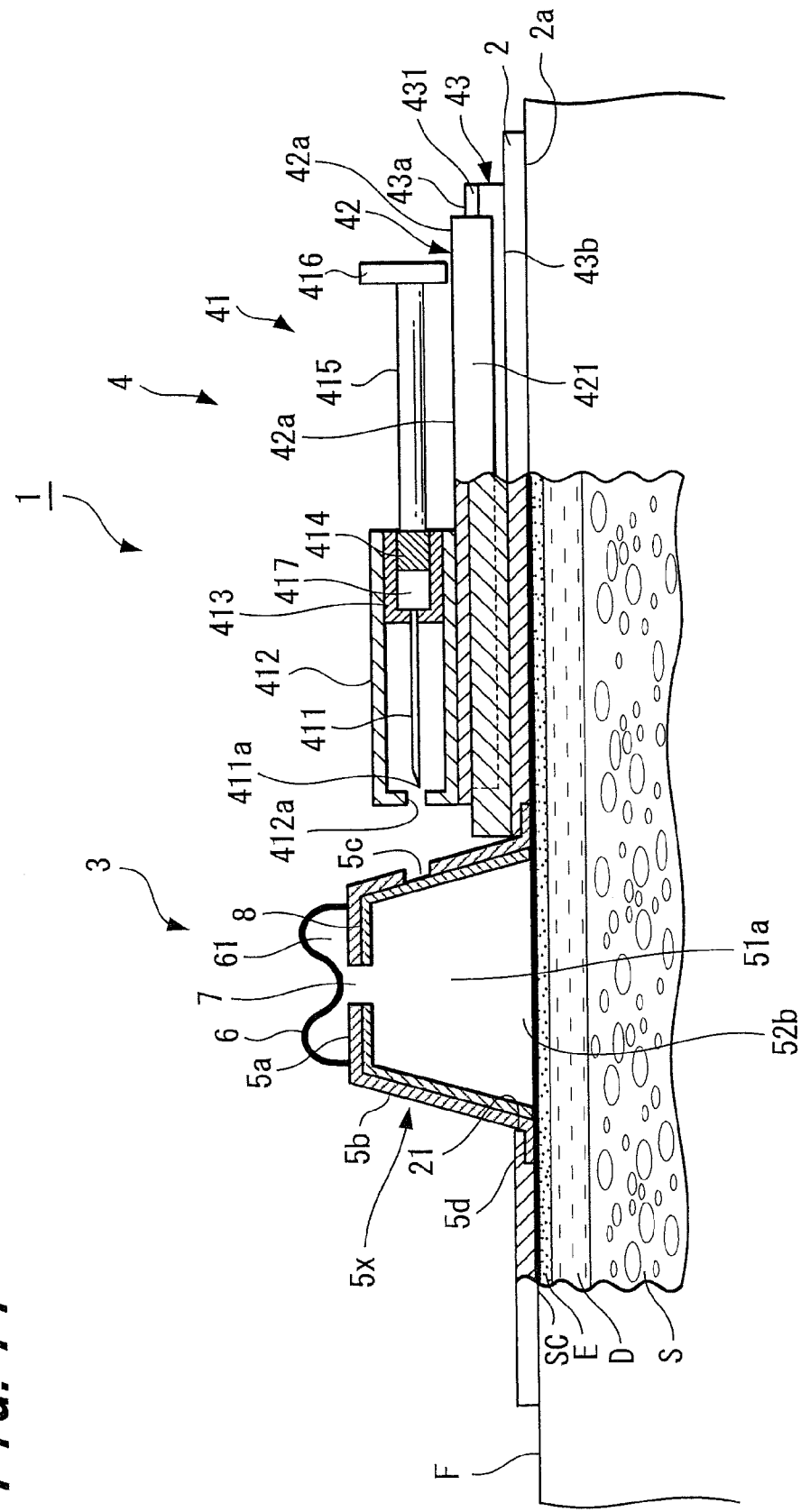
[FIG. 14] A cross-section view by A-A line in FIG. 13.

FIG. 13 is a perspective view showing a fourth exemplified embodiment of a puncture device of the present invention. FIG. 14 is a diagram showing a cross-section view by A-A line in FIG. 13. Also, FIG. 15 and FIG. 16 are diagrams (cross-section views) for explaining usage of the puncture device shown in FIG. 13. It should be noted that it will be explained hereinafter on an assumption that the right side in FIG. 14 to FIG. 16 is made to be "rear end" and the left side thereof is made to be "tip".

A puncture device 1 shown in FIG. 13 is constituted by being provided with an adhesive pad 2 which is a fixing portion, a skin deforming means 3 for deforming and uplifting the skin, a puncture needle moving means 4 for retaining a puncture needle 411 to be movable and the like.

The adhesive pad 2 is almost rounded and is formed so as to have a shape in which facing concave portions are formed at portions of the circumference thereof, so-called, a wing-like shape.

It should be noted that the wing-like shape of the adhesive pad 2 is formed such that the area of the side on which the puncture needle moving means 4 is mounted becomes larger than he area of the side on which the skin deforming means 3 is provided. In this manner, by making the area of the adhesive pad 2 on the side on which the puncture needle moving means 4 is mounted to be larger, it is possible to increase stability with respect to a body surface F and to carry out the movement of the puncture needle 411 by means of the puncture needle moving means 4 in a stable state.

The adhesive pad 2 is formed with a through-hole 21 for mounting a main body portion 5x of a box shape, which is the skin deforming means 3 on the body surface F.

As shown in FIG. 14, there is formed on the body surface F side of the adhesive pad 2 with a plane 2a for fixing the adhesive pad 2 by being appressed to the body surface F. An adhesion means is provided on this plane 2a and as the adhesion means, it is allowed to apply an adhesive agent on the plane 2a in the form of laminae or it is also allowed to glue an adhesive film constituted by a two-sided tape thereon.

The plane 2a of the adhesive pad 2 is fixed on the body surface F by being appressed thereto by means of an adhesive agent. It should be noted that there are arranged, on the lower side of the body surface F, a stratum corneum SC, an epidermis E including the stratum corneum SC, a dermis D and a subcutis S in the form of laminae.

Then, as being described hereinafter, the puncture needle 411 is moved to the tip direction along the plane 2a of the adhesive pad 2 by the puncture needle moving means 4 and the skin uplifted by the skin deforming means 3 is to be punctured.

The adhesive pad 2 is constituted, for example, by soft polymer such as flexible polyurethane or the like.

The skin deforming means 3 is constituted by the main body portion 5x and a suction means 6.

The main body portion 5x is constituted by a tubular member with a bottom, is formed by a bottom face portion 5a having approximately a square shaped plate at the base end and a peripheral wall portion 5b having a plurality of planes juncturally positioned at this bottom face portion 5a and has a box shape (BOX SHAPE).

There is formed on the body surface F side of the bottom face portion 5a with a skin fixing plane 5e for fixing the skin uplifted by the skin deforming means 3.

Also, as shown in FIG. 14, there is formed on the body surface F side of the main body portion 5x with an opening portion 52a in which it is constituted to be opened up toward the body surface F. This main body portion 5x has a constitution in which a space 51a formed in the inside thereof is to be hermetically-closed (sealed to be airtight) by pressing the opening portion 52a to the skin (body surface F).

Also, a flange portion 5d is formed on the circumference surface of the tip of the main body portion 5x. It is possible by providing the flange portion 5d to improve airtightness of the space 51a when pressing the opening portion 52a to the body surface F.

An elastic body 6 having a hollow portion 61 as a suction means is firmly-fixed (fixed) on the outer surface (upper surface) of the bottom face portion 5a.

The elastic body 6 has a cube shape and is constituted by an elastically deformable member. Also, the hollow portion 61 is formed inside the elastic body 6. It should be noted that the shape of the elastic body 6 is limited by the cube shape such as this exemplified embodiment.

Also, a through-hole 7 is formed at the central portion of the bottom face portion 5a of the main body portion 5x. Thereby, the hollow portion 61 of the elastic body 6 and the space 51a of the main body portion 5x are in communication with each other by way of the through-hole 7.

Also, there is provided on the inner surface (lower surface) of the bottom face portion 5a with an adhesive film 8 as a skin adhesion means.

The adhesive film 8 is provided also on the inner surface of the peripheral wall portion 5b. This adhesive film 8 is provided so as to cover an insertion opening 5c formed on the peripheral wall portion 5b, so that it is possible to improve the airtightness of the space 51a.

By pressing the opening portion 52a of the main body portion 5x to the body surface F in a state in which the elastic body 6 is compressed and by releasing the compressed state of the elastic body 6, air in the space 51a is sucked into the hollow portion 61 of the elastic body 6 and it is possible to depressurize the space 51a.

For the constituent material of the elastic body 6, there can be cited various kinds of rubber materials such as natural rubber, isoprene rubber, butadiene rubber, styrene-butadiene rubber, nitrile rubber, chloroprene rubber, butyl rubber, acrylic rubber, ethylene-propylene rubber, hydrin rubber, urethane rubber, silicone rubber, fluoro-rubber and the like or various kinds of thermoplastic elastomers such as styrene series, polyolefin series, polyvinylchloride series, polyurethane series, polyester series, polyamide series, polybutadiene series, fluoro-rubber series and the like.

It should be noted for the suction means that it is allowed to employ such a constitution wherein, for example, a syringe is fixed at an edge portion of a tube which is made to be in communication with the space 51a and the air in the space 51a is to be sucked by the operation of the syringe.

There is formed on the plane 50a facing to the puncture needle moving means 4 among the planes of the peripheral wall portion 5b with the insertion opening 5c as a through-hole. Thereby, through the insertion opening 5c, the puncture needle 411 moved by the puncture needle moving means 4 is inserted into the inside of the main body portion 5x.

The puncture needle moving means 4 is constituted by an injector 41 having the puncture needle 411, a mounting member 42 for mounting and fixing the injector 41 and a support member 43 for supporting the mounting member 42 to be movable.

The injector 41 is provided with the puncture needle 411, a fixed outer cylinder 412, an internal outer cylinder 413 slidable in the fixed outer cylinder 412, a gasket 414 slidable in the internal outer cylinder 413 and a plunger 415 which moving-operates the gasket 414.

The fixed outer cylinder 412 has a cylindrical shape with bottom and is mounted and fixed on the mounting member 42 by means of adhesive agent or the like. Also, there is formed in the vicinity of the central portion of the bottom portion of the fixed outer cylinder 412 with a puncture needle opening 412a for carrying out insertion of the puncture needle 411.

The internal outer cylinder 413 has a cylindrical shape with bottom. Also, the puncture needle 411 is firmly fixed by adhesion in the vicinity of the central portion of bottom portion.

The needlepoint 411a of the puncture needle 411 is provided so as not to project from the puncture needle opening 412a provided at the fixed outer cylinder 412. More specifically, the puncture needle 411 is located with respect to the fixed outer cylinder 412 such that the needlepoint 411a thereof is positioned on the inner side as compared with the bottom face of the fixed outer cylinder 412 on which the puncture needle opening 412a is provided and also in the vicinity of the puncture needle opening 412a.

It is possible by constituting in this manner to protect the needlepoint 411a of the puncture needle 411. Also, it is possible to reduce awful feeling of a user, because the needlepoint 411a becomes hard to be seen.

The outer diameter of the puncture needle 411 is a little bit different depending on the use application or the like of the puncture device 1, but it is preferable to select it as around 0.05 to 2.5 mm and in particular, preferable to select it as around 0.1 to 1.5 mm.

There can be cited, for the constituent material of the puncture needle 411, metal materials such as, for example, stainless steel, aluminum or aluminum alloy, titanium or titanium alloy and the like. Also, the puncture needle 411 is manufactured, for example, by plastic working.

It is possible for the internal outer cylinder 413 to slide in the fixed outer cylinder 412 in a longitudinal direction of the internal outer cylinder 413 by means of the operation of the plunger 415 and when the internal outer cylinder 413 slides, the puncture needle 411 firmly fixed to the internal outer cylinder 413 is taken in and out with respect to the fixed outer cylinder 412 through the puncture needle opening 412a.

For the constituent material of the fixed outer cylinder 412 and the internal outer cylinder 413, there can be cited various kinds of resins such, for example, as polyvinylchloride, polyethylene, polypropylene and the like. It should be noted that the constituent material of the fixed outer cylinder 412 and the internal outer cylinder 413 is desirable to be substantially transparent in order to ensure visibility of the inside.

There is housed, in the internal outer cylinder 413, the gasket 414 constituted by an elastic material.

For the constituent material of the gasket 414, although it is not limited in particular, there can be cited, for example, various kinds of rubber materials such as natural rubber and silicone rubber, various kinds of thermoplastic elastomers of polyurethane series, styrene series and the like or elastic materials of mixtures thereof and the like.

In the space surrounded by the gasket 414 and internal outer cylinder 413, a liquid room 417 is formed and in this liquid room 417, liquid is contained liquid-tightly beforehand.

There can be cited for the liquid, for example, remedy for injection or medicinal solution using a macromolecular substance such as hormone, antibody drug, cytokine, vaccine or the like.

erate the gasket 414 in the internal outer cylinder 413 in a longitudinal direction.

A plate-like flange 416 is formed integrally at the rear end of the plunger 415. The plunger 415 is operated by depressing this flange 416 with a finger or the like.

The mounting member 42 is constituted so as to include an upper surface portion 42a for mounting the injector 41. At the edge portion in a longitudinal direction of the surface portion 42a, there is formed, by being projected toward the adhesive pad 2, a U-shaped engagement portion 421 to be movable and for being engaged with the support member 43.

The support member 43 is constituted by a rectangular plate-like body having an upper surface portion 43a which contacts slidably with a mounting member 421. At the edge portion in a longitudinal direction of the support member 43, there is formed, by being projected to the horizontal direction with respect to the adhesive pad 2, an engagement convex portion 431 which has such a shape to coincide with the U-shaped engagement portion 421 which is formed on the mounting member 42.

On the plane on the opposite side of the upper surface portion 43a of the support member 43, there is formed a lower surface portion 43b for being fixed with the adhesive pad 2 adhesively. As shown in FIG. 14, the lower surface portion 43b of the support member 43 is fixed on the adhesive pad 2 by adhesive agent or the like.

There can be cited for the constituent material of the mounting member 42 and the support member 43 various kinds of resins such as polyethylene, polypropylene or the like and the mounting member 42 and the support member 43 are manufactured by a forming process inpouring these resins into a die which has a predetermined shape or the like.

It should be noted as the puncture needle moving means 4 that it is allowed to employ such a constitution wherein an injector having a constitution in which a puncture needle and a syringe are formed as one body configuration is fixed and retained on the mounting member 42. In this case, the length of the puncture needle 411 is adjusted such that the needle-point 411a of the puncture needle 411 can puncture the skin uplifted by the skin deforming means 3 when the mounting member 42 is moved so as to most approach to the skin deforming means 3.

Next, it will be explained by using FIG. 15 and FIG. 16 with respect to usage (operation) of the puncture device 1 of this exemplified embodiment.

First, the adhesive pad 2 is mounted on a predetermined position of the body surface F. At that time, the plane 2a of the adhesive pad 2 is bonded and fixed on the body surface F by means of an adhesive film provided on the body surface F side of the adhesive pad 2. In this state, the main body portion 5x is inserted into the through-hole 21 formed on the adhesive pad 2 and by contacting and fixing the flange 5d onto the body surface F, the main body portion 5x is mounted on the body surface F.

Figure 15A:
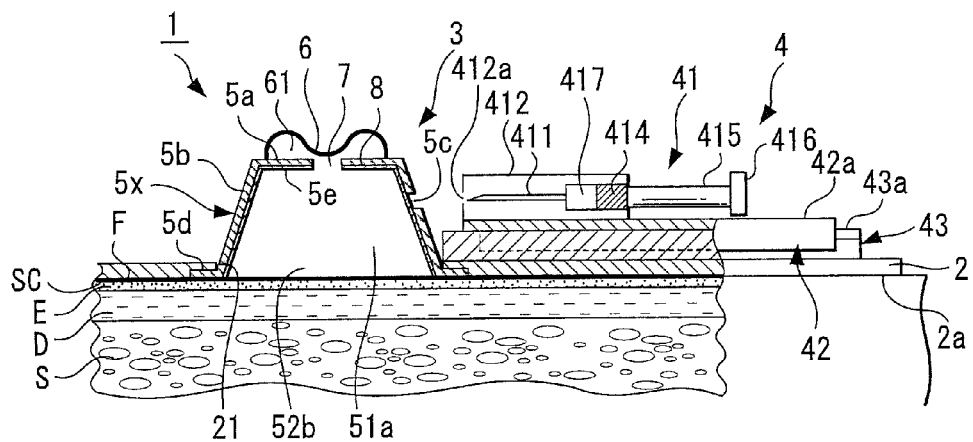
[FIG. 15] Diagrams (cross-section views) for explaining usage of the puncture device shown in FIG. 13.

In this case, as shown in FIG. 15A, the elastic body 6 is deformed by being grasped with a finger or the like and the air in the hollow portion 61 of the elastic body 6 is exhausted.

Figure 15B:
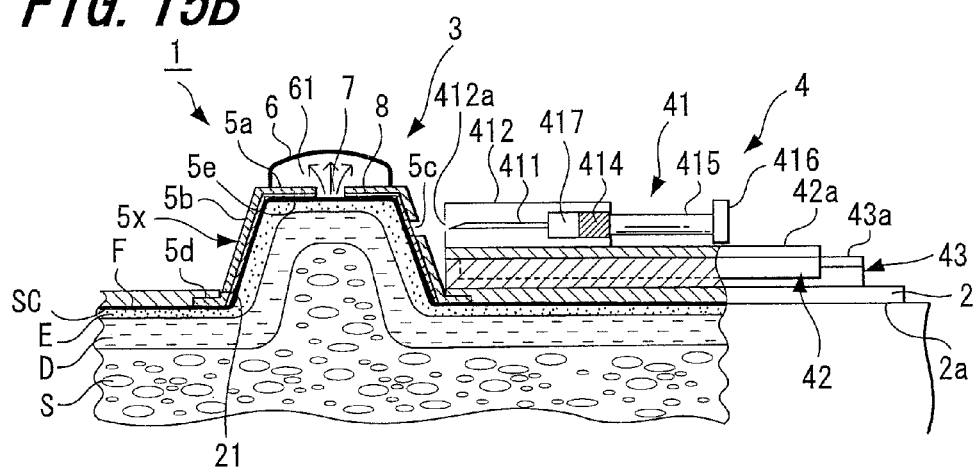

Next, as shown in FIG. 15B, the finger is released from the elastic body 6 and the compressed state of the elastic body 6 is released, and then the air in the space 51a is sucked into the hollow portion 61 through the through-hole 7 as shown by arrows.

Thereby, the space 51a is depressurize and the skin on the inner side of the opening portion 52a is uplifted into the space 51a. More specifically, the epidermis E including the stratum corneum SC, the dermis D and the subcutis S are pulled upward respectively and the skin is uplifted to the vertical direction with respect to the body surface F.

More specifically, the position of the plane 2a of the adhesive pad 2, which is the fixing portion and the position of the skin fixing plane 5e formed in the main body portion 5x become different in the height direction, so that a step portion is formed there-between and the puncture needle 411 is inserted into the step portion thereof and stuck into the uplifted and deformed skin.

Then, the skin uplifted into the space 51a contacts with the adhesive film 8 provided on the bottom face portion 5a and on the peripheral wall portion 5b and is fixed thereon adhesively. At that time, a portion of the body surface F is fixed so as to become in parallel with the bottom face portion 5a, so that also a portion of the dermis D is fixed in the main body portion 5x so as to become in parallel with the bottom face portion 5a.

Next, the mounting member 42 on which the injector 41 is fixedly retained is slid to the tip direction.

Next, the plunger 415 is operated by depressing the flange 416 with a finger or the like and the internal outer cylinder 413 is moved to the tip direction while being slided in the fixed outer cylinder 412. Thereby, the puncture needle 411 firmly fixed on the internal outer cylinder 413 is inserted from the puncture needle opening 412a into the insertion opening 5c provided on the peripheral wall portion 5b.

Figure 15C:
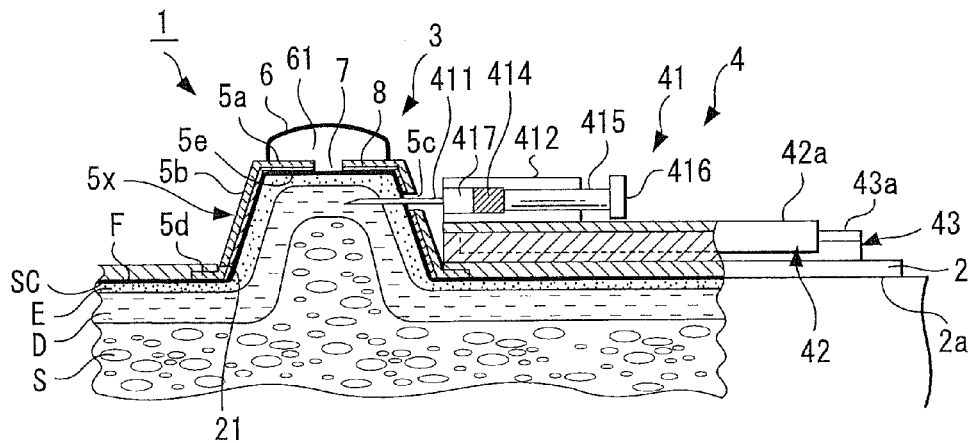

At that time, the puncture needle 411 is punctured in a state in parallel with the skin fixing plane 5e provided on the bottom face portion 5a, so that, as shown in FIG. 15C, the puncture needle 411 is stuck in the skin in a state in parallel with the dermis D.

Figure 16A:
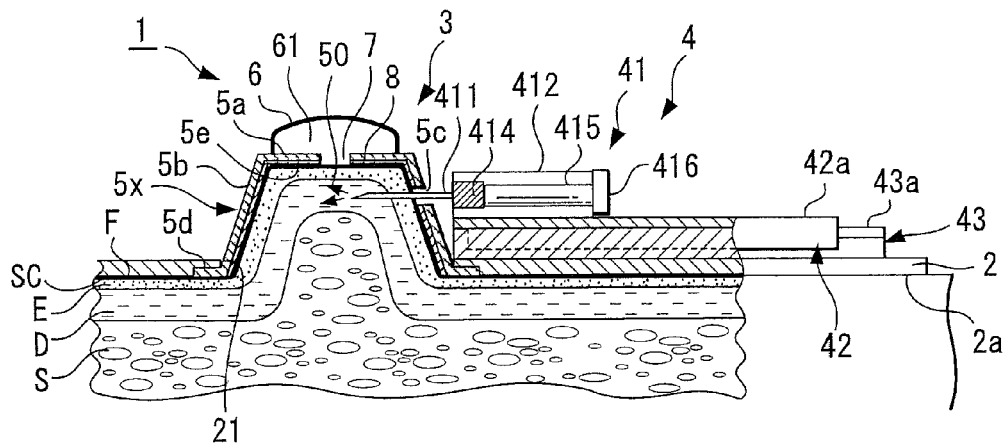
[FIG. 16] Diagrams (cross-section views) for explaining usage of the puncture device shown in FIG. 13.

The plunger 415 is operated by further depressing the flange 416 with a finger or the like from that state and the gasket 414 is moved to the tip direction while sliding it in the internal outer cylinder 413. Thereby, as shown in FIG. 16A, a medical agent 50 contained in the liquid room 417 is injected from the needlepoint 411a of the puncture needle 411 to the dermis D.

After the medical agent is injected into the dermis D, the plunger 415 is operated by pulling the flange 416 with a finger or the like, the gasket 414 is moved to the rear end direction and the puncture needle 411 is pulled out from the dermis D.

Figure 16B:
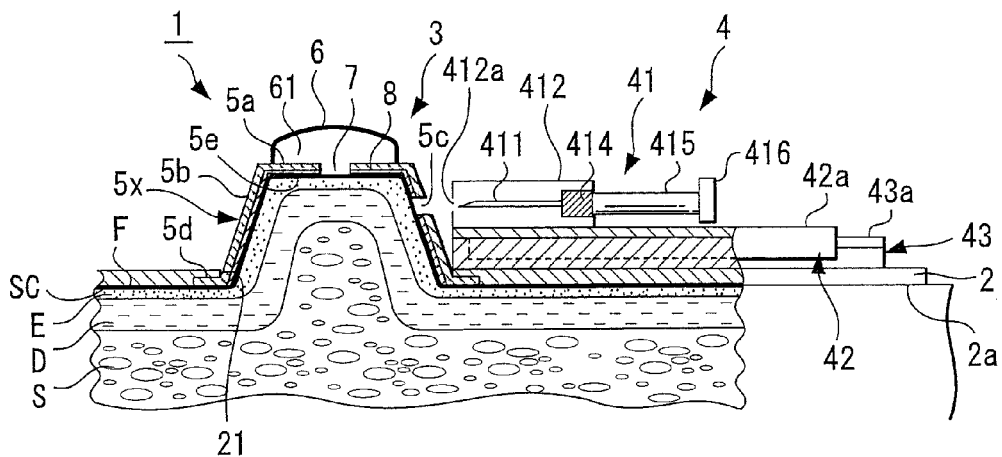

Further, the plunger 415 is moved to the rear end direction and as shown in FIG. 16B, the puncture needle 411 is housed in the fixed outer cylinder 412 through the puncture needle opening 421a.

Figure 16C:
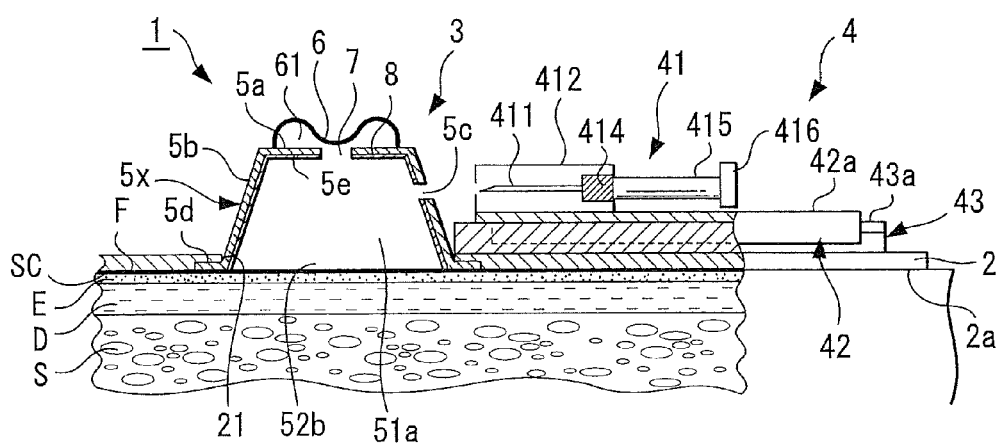

Next, in a state in which the puncture needle 411 is housed in the fixed outer cylinder 412, the mounting member 42 is slided to the rear end direction and it is made to be a state of FIG. 16C.

Concurrently, the elastic body 6 is depressed and deformed by a finger or the like and the air in the hollow portion 61 is sent to the space 51a of the main body portion 5x. Thereby, the space 51a is pressurized and the skin uplifted in the space 51a returns to the original state.

In this manner, according to the puncture device 1 of this exemplified embodiment, in a state in which the opening portion 52b of the main body portion 5x is pressed to the body surface F the air in the space 51a is sucked by the elastic body 6 so as to depressurize the space 51a. Thereby, the skin including the dermis D is uplifted in the space 51a and the skin is fixed by the adhesive film 8 provided on the bottom face 2a and thereafter, it is possible to puncture the dermis D by the puncture needle 411. More specifically, the puncture operation is carried out in a state in which the skin is uplifted, so that it is possible to stick the puncture needle 411 into the skin (dermis D) certainly and also, it is possible to inject a medical agent to the dermis D of the skin certainly.

Also, the puncture needle 411 is stuck into the dermis D in the skin approximately in a parallel state, so that the insertion depth of the puncture needle 411 in the inside of the dermis D becomes long and even in a case in which an impact or the like is added from the outside, the puncture needle 411 during injecting the medical agent can be prevented from dropping out from the dermis D.

Also, the distance from the insertion aperture of the puncture needle 411, which is formed at a boundary portion between the epidermis E and the dermis D to the medical agent releasing aperture which exists at the needlepoint 411a becomes long, so that the medical agent once injected into the dermis D from the medical agent releasing aperture can be prevented from leaking from the insertion aperture to the epidermis E by being flown back [backward].

Fifth Exemplified Embodiment

Next, it will be explained with respect to a fifth exemplified embodiment of a puncture device of the present invention.

Figure 18:
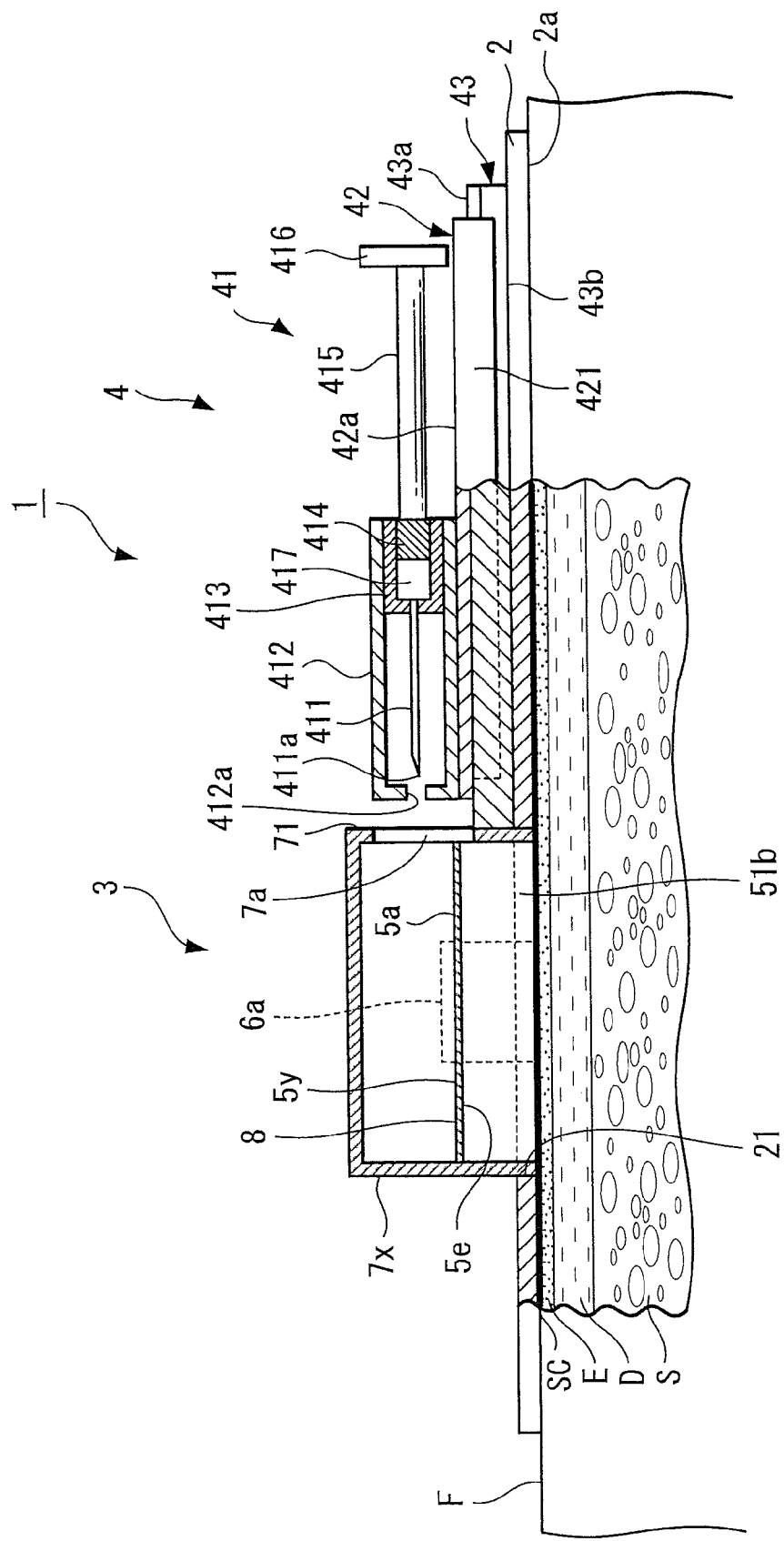
[FIG. 18] A cross-section view by A-A line in FIG. 17.

FIG. 17 is a perspective view showing a fifth exemplified embodiment of a puncture device of the present invention. FIG. 18 is a diagram showing a cross-section view by A-A line in FIG. 17.

Also, FIG. 19 and FIG. 20 are diagrams (cross-section view) for explaining the usage of the puncture device shown in FIG. 17.

It should be noted that it will be explained hereinafter on an assumption that the right side in FIG. 18 to FIG. 20 is made to be "rear end" and the left side thereof is made to be "tip".

A puncture device 1 shown in FIG. 17 is constituted by being provided with an adhesive pad 2 which is a fixing portion, a skin deforming means 3 for deforming and uplifting the skin, a puncture needle moving means 4 for retaining a puncture needle 411 to be movable and the like.

The adhesive pad 2 is almost rounded and is formed so as to have a shape in which facing cocave portions are formed at portions of the circumference thereof, so-called, a wing-like shape.

It should be noted that the wing-like shape of the adhesive pad 2 is formed such that the area of the side on which the puncture needle moving means 4 is mounted becomes larger than he area of the side on which the skin deforming means 3 is provided. In this manner, by making the area of the adhesive pad 2 on the side on which the puncture needle moving means 4 is mounted to be larger, it is possible to increase stability with respect to a body surface F and to carry out the movement of the puncture needle 411 by means of the puncture needle moving means 4 in a stable state.

The adhesive pad 2 is formed with a through-hole 21 for mounting the skin deforming means 3 on the body surface F.

As shown in FIG. 18, there is formed on the body surface F side of the adhesive pad 2 with a plane 2a for fixing the adhesive pad 2 by being appressed to the body surface F. An adhesion means is provided on this plane 2a and as the adhesion means, it is allowed to apply an adhesive agent on the plane 2a in the form of laminae or it is also allowed to glue an adhesive film constituted by a two-sided tape thereon.

The plane 2a of the adhesive pad 2 is fixed on the body surface F by being appressed thereto by means of an adhesive agent. It should be noted that there are arranged, on the lower side of the body surface F, a stratum corneum SC, an epidermis E including the stratum corneum SC, a dermis D and a subcutis S in the form of laminae.

Then, as being described hereinafter, the puncture needle 411 is moved to the tip direction along the plane 2a of the adhesive pad 2 by the puncture needle moving means 4 and the skin uplifted by the skin deforming means 3 is to be punctured.

There can be cited for the constituent material of such an adhesive pad 2, for example, soft polymer such as flexible polyurethane or the like.

The skin deforming means 3 is provided with a tabular member 5y, handles 6a mounted on the tabular member 5y and an outer frame 7x retaining the handles 6a to be movable.

The tabular member 5y has flexibility and is constituted by a bendable flat plate of approximately a square shape. It should be noted that approximately a square shape configuration is employed in this exemplified embodiment, but it is allowed to employ, for example, a rectangle shape configuration.

Also, as shown in FIG. 18, there is formed on the surface of the tabular member 5y on the body surface F side with a skin fixing plane 5e and there is provided on this skin fixing plane 5e with an adhesive film 8 as a skin bonding means.

The adhesive film 8 is provided at least on the side on which the handle 6a of the tabular member 5y is provided and on the center line 5a of the tabular member 5y so as to be along therewith. It should be noted as the skin bonding means that it is allowed to apply an adhesive agent on the tabular member 5 in the form of laminae.

It is enough for the constituent material of such a tabular member 5y if only it is a material which is deformable by a finger or the like and has adequate elasticity and, for example, metal materials and various kinds of resins can be cited.

The handle 6a is constituted by a L-shaped member and is firmly fixed on the side portion of the tabular member 5y by means of an adhesive agent.

The position on which the handle 6a is firmly fixed is in the vicinity of the central portion on the side, among the four sides which the tabular member 5y has, which is in parallel with the moving direction of the puncture needle 411 and two handles 6a are mounted on the tabular member 5y so as to become symmetrical to each other.

The outer frame 7x is constituted by a cube shaped member and has four side surfaces. Also, the outer frame 7x is formed with an opening 51b toward the body surface F side.

Also, there are formed on the body surface F side of the two side surfaces 72 which become parallel with the moving direction of the puncture needle 411 with engagement openings (not shown) for engaging with the handles 6a, respectively.

The two handles 6a are engaged with the engagement openings so as to be movable with respect to the outer frame 7x. More specifically, the outer frame 7x is constituted such that the handles 6a are retained thereon to be movable.

Also, there is formed on a side surface 71, facing to the puncture needle moving means 4, of the outer frame 7x with an insertion opening 7a. The insertion opening 7a is formed so as to have a half round shape and the puncture needle 411 is inserted into the outer frame 7x through this insertion opening 7a by means of the puncture needle moving means 4.

The puncture needle moving means 4 is constituted by an injector 41 having the puncture needle 411, a mounting member 42 for mounting and fixing the injector 41 and a support member 43 for supporting the mounting member 42 to be movable.

The injector 41 is provided with the puncture needle 411, a fixed outer cylinder 412, an internal outer cylinder 413 slidable in the fixed outer cylinder 412, a gasket 414 slidable in the internal outer cylinder 413 and a plunger 415 which moving-operates the gasket 414.

The fixed outer cylinder 412 has a cylindrical shape with bottom and is mounted and fixed on the mounting member 42 by means of adhesive agent or the like. Also, there is formed in the vicinity of the central portion of the bottom portion of the fixed outer cylinder 412 with a puncture needle opening 412a for carrying out insertion of the puncture needle 411.

The internal outer cylinder 413 has a cylindrical shape with bottom. Also, the puncture needle 411 is firmly fixed by adhesion in the vicinity of the central portion of bottom portion.

The needlepoint 411a of the puncture needle 411 is provided so as not to project from the puncture needle opening 412a provided a the fixed outer cylinder 412. More specifically, the puncture needle 411 is located with respect to the fixed outer cylinder 412 such that the needlepoint 411a thereof is positioned on the inner side as compared with the bottom face of the fixed outer cylinder 412 on which the puncture needle opening 412a is provided and also in the vicinity of the puncture needle opening 412a.

It is possible by constituting in this manner to protect the needlepoint 411a of the puncture needle 411. Also, it is possible to reduce awful feeling of a user, because the needlepoint 411a becomes hard to be seen.

The outer diameter of the puncture needle 411 is a little bit different depending on the use application of the puncture device 1 or the like, but it is preferable to select it as around 0.05 to 2.5 mm and in particular, preferable to select it as around 0.1 to 1.5 mm.

There can be cited, for the constituent material of the puncture needle 411, metal materials such as, for example, stainless steel, aluminum or aluminum alloy, titanium or titanium alloy and the like. Also, the puncture needle 411 is manufactured, for example, by plastic working.

It is possible for the internal outer cylinder 413 to slide in the fixed outer cylinder 412 in a longitudinal direction of the internal outer cylinder 413 by means of the operation of the plunger 415 and when the internal outer cylinder 413 slides, the puncture needle 411 firmly fixed to the internal outer cylinder 413 is taken in and out with respect to the fixed outer cylinder 412 through the puncture needle opening 412a.

For the constituent material of the fixed outer cylinder 412 and the internal outer cylinder 413, there can be cited various kinds of resins such, for example, as polyvinylchloride, polyethylene, polypropylene and the like. It should be noted that the constituent material of the fixed outer cylinder 412 and the internal outer cylinder 413 is desirable to be substantially transparent in order to ensure visibility of the inside.

There is housed, in the internal outer cylinder 413, the gasket 414 constituted by an elastic material.

For the constituent material of the gasket 414, although it is not limited in particular, there can be cited, for example, various kinds of rubber materials such as natural rubber and silicone rubber, various kinds of thermoplastic elastomers of polyurethane series, styrene series and the like or elastic materials of mixtures thereof and the like.

In the space surrounded by the gasket 414 and internal outer cylinder 413, a liquid room 417 is formed and in this liquid room 417, liquid is contained liquid-tightly beforehand.

There can be cited for the liquid, for example, remedy for injection or medicinal solution using a macromolecular substance such as hormone, antibody drug, cytokine, vaccine or the like.

There is interlinked to the gasket 414 the plunger 415 which moving-operate the gasket 414 in the internal outer cylinder 413 in a longitudinal direction.

A plate-like flange 416 is formed integrally at the rear end of the plunger 415. The plunger 415 is operated by depressing this flange 416 with a finger or the like.

The mounting member 42 is constituted so as to include a upper surface portion 42a for mounting the injector 41. At the edge portion in a longitudinal direction of the upper surface portion 42a, there is formed, by being projected toward the adhesive pad 2, a U-shaped engagement portion 421 to be movable and for being engaged with the support member 43.

The support member 43 is constituted by a rectangular plate-like body having an upper surface portion 43a which contacts slidably with a mounting member 42. At the edge portion in a longitudinal direction of the support member 43, there is formed, by being projected to the horizontal direction with respect to the adhesive pad 2, an engagement convex portion 431 which has such a shape to coincide with the U-shaped engagement portion 421 which is formed on the mounting member 42.

On the plane on the opposite side of the upper surface portion 43a of the support member 43, there is formed a lower surface portion 43b for being fixed with the adhesive pad 2 adhesively. As shown in FIG. 18, the lower surface portion 43b of the support member 43 is fixed on the adhesive pad 2 by adhesive agent or the like.

There can be cited for the constituent material of the mounting member 42 and the support member 43 various kinds of resins such as polyethylene, polypropylene or the like and the mounting member 42 and the support member 43 are manufacture by a forming process inpouring these resins into a die which has a predetermined shape or the like.

It should be noted as the puncture needle moving means 4 that it is allowed to employ such a constitution wherein an injector having a constitution in which a puncture needle and a syringe are formed as one body configuration is fixed and retained on the mounting member 42. In this case, the length of the puncture needle 411 is adjusted such that the needle-point 411a of the puncture needle 411 can puncture the skin uplifted by the skin deforming means 3 when the mounting member 42 is moved so as to most approach to the skin deforming means 3.

Next, it will be explained by using FIG. 19 and FIG. 20 with respect to usage (operation) of the puncture device 1 of this exemplified embodiment.

First, the adhesive pad 2 is mounted on a predetermined position of the body surface F. At that time, the plane 2a of the adhesive pad 2 is bonded and fixed on the body surface F by means of an adhesive film provided on the body surface F side of the adhesive pad 2.

In addition, also the outer frame 7x which is fitted with the through-hole 21 formed on the adhesive pad 2 and is fixed on the adhesive pad 2 is mounted on the skin. Concurrently, also the tabular member 5y and the handles 6a which are retained by the outer frame 7x are mounted on the skin.

At that time, if the puncture device 1 is held down softly in order to be mounted on the body surface F, the tabular member 5y will be fixed on the body surface F through the intervention of the adhesive film 8 owing to the elasticity of the skin.

Figure 19A:
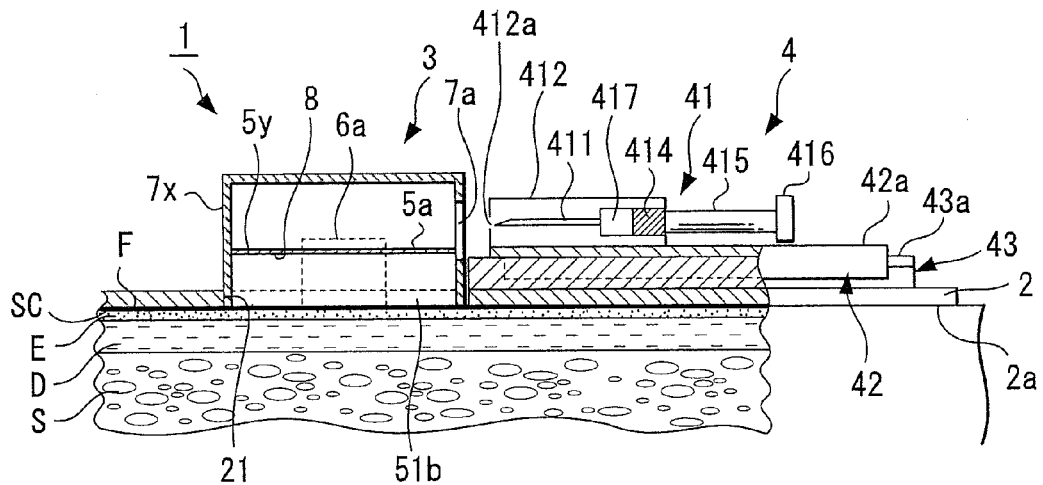
[FIG. 19] Diagrams (cross-section views) for explaining usage of the puncture device shown in FIG. 17.

Also, as shown in FIG. 19A, the tabular member 5y is mounted on the skin in such a state in which it is inflected upward slightly. In this manner, by making the tabular member 5y to be inflected slightly beforehand, it is possible, when the tabular member 5y is inflected by the handles 6a, to inflect the tabular member 5y upward easily.

Also, the skin deforming means 3 and the puncture needle moving means 4 are arranged on the adhesive pad 2 such that the moving direction of the puncture needle 411 and the center line 5a of the tabular member 5y coincide with each other.

Next, the handles 6a projecting on the adhesion pad 2 are grasped by fingers or the like and are moved so as to approach the outer frame 7x, and force is to be added to the tabular member 5y. Thereby, the planate member 5y is inflected so as to be along the center line 5a of the tabular member 5y.

At that time, according to the force added by the both the handles 6a, the body surface F fixed adhesively with the tabular member 5y by means of the adhesive film 8 is added with a force such as being pushed out towards the center line 5a of the tabular member 5y.

Figure 19B:
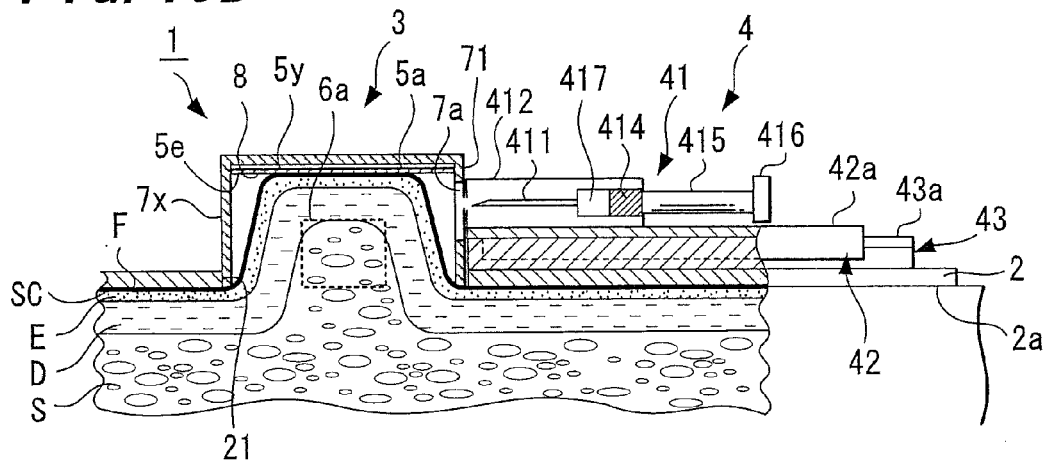

Further, when the handles 6a are made to approach the outer frame 7x, the tabular member 5y is further inflected. Also, concurrently, as shown in FIG. 19B, the body surface F defined by the portion fixed adhesively with the tabular member 5y is pushed out and uplifted upward. Thereby, the uplifted body surface F contacts with the adhesive film 8 provided on the tabular member 5y and bonded and fixed onto the tabular member 5y.

More specifically, the skin is fixed on the tabular member 5y in a state in which the epidermis E including the stratum corneum SC, the dermis D and the subcutis S are pulled upward respectively.

In other words, depending on a fact that the skin is deformed and uplifted, the position of the plane 2a of the adhesive pad 2, which is the fixing portion and the position of the skin fixing plane 5e provided on the tabular member 5y become different in the height direction, a step portion is formed there-between and the puncture needle 411 is stuck into the step portion thereof.

At that time, the uplifted body surface F is fixed so as to become in parallel with the center line 5a of the inflected tabular member 5y, so that also a portion of the dermis D is fixed in a state in which it becomes in parallel with the center line 5a.

Also, the epidermis E, the dermis D and the subcutis S which are uplifted are fixed in such a state as being along the inflection of the tabular member 5y, respectively. It should be noted that, the moving distance of the handle 6a which is engaged with the outer frame 7x to be movable is set such that the height of the uplifted skin becomes constant.

Next, the mounting member 42 on which the injector 41 is fixedly retained is slid to the tip direction.

Next, the plunger 415 is operated by depressing the flange 416 with a finger or the like and the internal outer cylinder 413 is moved to the tip direction while being slid in the fixed outer cylinder 412. Thereby, the puncture needle 411 firmly fixed on the internal outer cylinder 413 is inserted from the puncture needle opening 412a into the insertion opening 7a provided on the side surface 71 of the outer frame 7x.

At that time, the puncture needle 411 of the injector 41 is stuck in a state coinciding with the center line 5a of the planate member 5y.

Figure 19C:
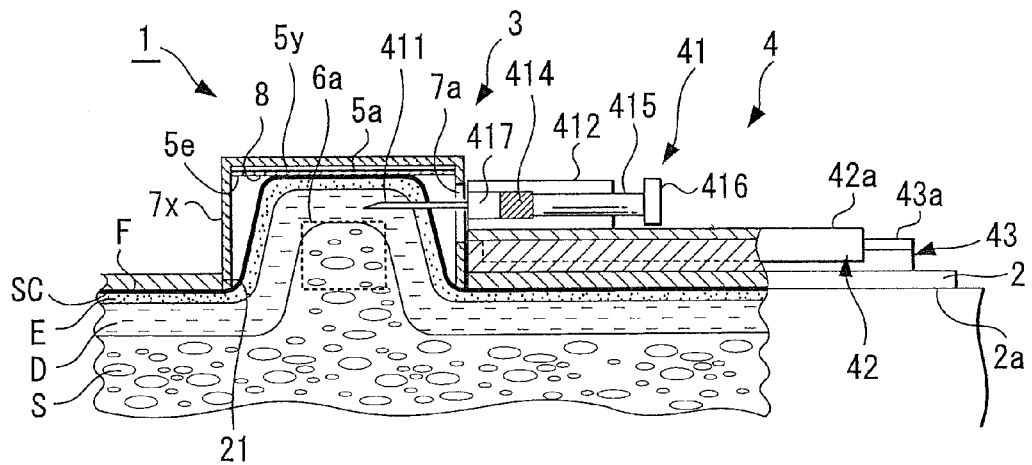

Also, as shown in FIG. 19C, the puncture needle 411 is moved in the skin such that it becomes in parallel with the skin fixing plane 5e and is stuck from the step portion in such a state as becoming in parallel with the uplifted dermis D.

Figure 20A:
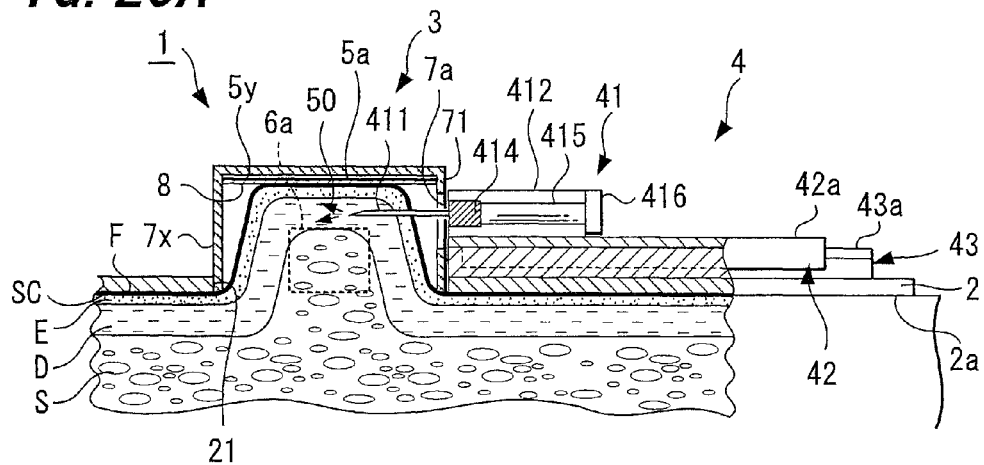
[FIG. 20] Diagrams (cross-section views) for explaining usage of the puncture device shown in FIG. 17.

The plunger 415 is operated by further depressing the flange 416 with a finger or the like from that state and the gasket 414 is moved to the tip direction while sliding it together with the internal outer cylinder 413. Thereby, as shown in FIG. 20A, a medical agent 50 contained in the liquid room 417 is injected from the needlepoint 411a of the puncture needle 411 to the dermis D.

After the medical agent is injected into the dermis D, the plunger 415 is operated by pulling the flange 416 with a finger or the like, the gasket 414 is moved to the rear end direction and the puncture needle 411 is pulled out from the puncture region P.

Figure 20B:
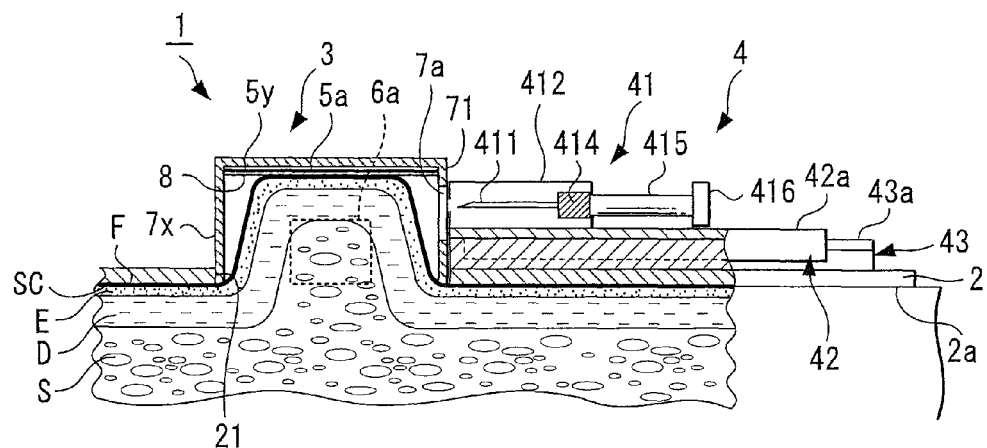

Further, the plunger 415 is moved to the rear end direction and as shown in FIG. 20B, the puncture needle 411 is housed in the fixed outer cylinder 412 from the puncture needle opening 412a.

Figure 20C:
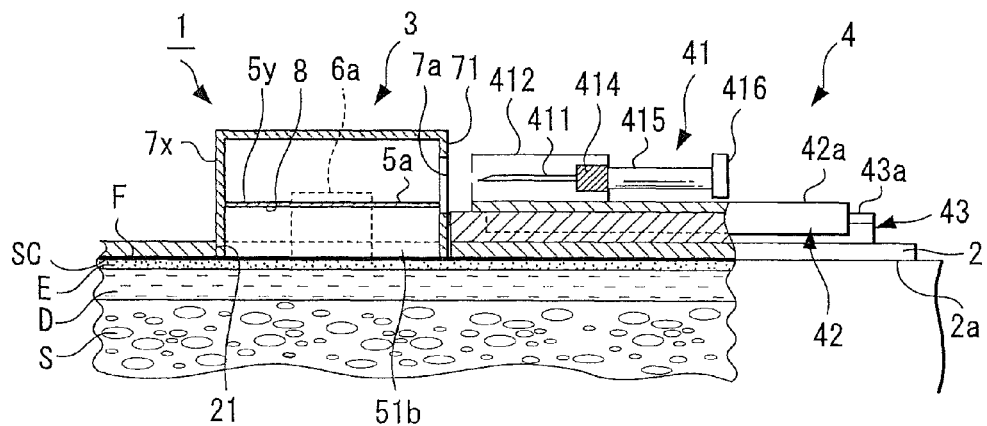

Next, in this state, the mounting member 42 on which the injector 41 is fixedly retained is slid to the rear end direction and it is made to be a state of FIG. 20C.

In this manner, according to the puncture device 1 of this exemplified embodiment, it is possible to carry out the puncture by the puncture needle 411 after the skin including the dermis D is uplifted by the handles 6a and the skin is fixed by the adhesive film 8 provided on the planate member 5y. More specifically, the puncture operation is carried out in a state in which the skin is uplifted, so that it is possible to stick the puncture needle 411 into the skin (dermis D) certainly and also, it is possible to inject a medical agent to the dermis D of the skin certainly.

Also, the puncture needle 411 is stuck so as to become approximately a parallel state with respect to the dermis D in the skin, so that the insertion depth of the puncture needle 411 in the inside of the dermis D becomes long and even in a case in which an impact or the like is added from the outside, the puncture needle 411 during injecting the medical agent can be prevented from dropping out from the dermis D.

Also, the distance from the insertion aperture of the puncture needle 411, which is formed at a boundary portion between the epidermis E and the dermis D to the medical agent releasing aperture which exists at the needlepoint 411a becomes long, so that the medical agent once injected into the dermis D from the medical agent releasing aperture can be prevented from leaking from the insertion aperture to the epidermis E by being flown back [backward].

It should be noted that it was explained by one puncture needle 411 and one puncture needle moving means 4 in the above-described exemplified embodiment, but a plurality of puncture needles and a plurality of puncture needle moving means may be provide instead. In this case, it is preferable to arrange a plurality of puncture needles so as to become in parallel with respect to the inflected tabular member 5y. By constituting in this manner, it is possible to make the insertion positions of the plurality of puncture needles in the skin to be at constant depth in the skin depth direction.

In addition, the above-described exemplified embodiments were explained by using examples in which the puncture needle is always stuck to the dermis D, but it is possible to use the puncture device of the present invention also incase of sticking to an intracutaneous area, a subcutis or further a muscle other than the dermis.

Also, the puncture device of the present invention is not limited by the above-mentioned each exemplified embodiment and besides that, it goes without saying that various modifications or changes can be employed for the materials, the constitutions or the like in the region without departing from the configuration of the present invention. In particular, it is possible to make the shape, the structure and the like of the outer frame 7x to be arbitrary ones which can exert similar functions.

Sixth Exemplified Embodiment

Next, it will be explained with respect to a sixth exemplified embodiment of a puncture device of the present invention.

Figure 21:
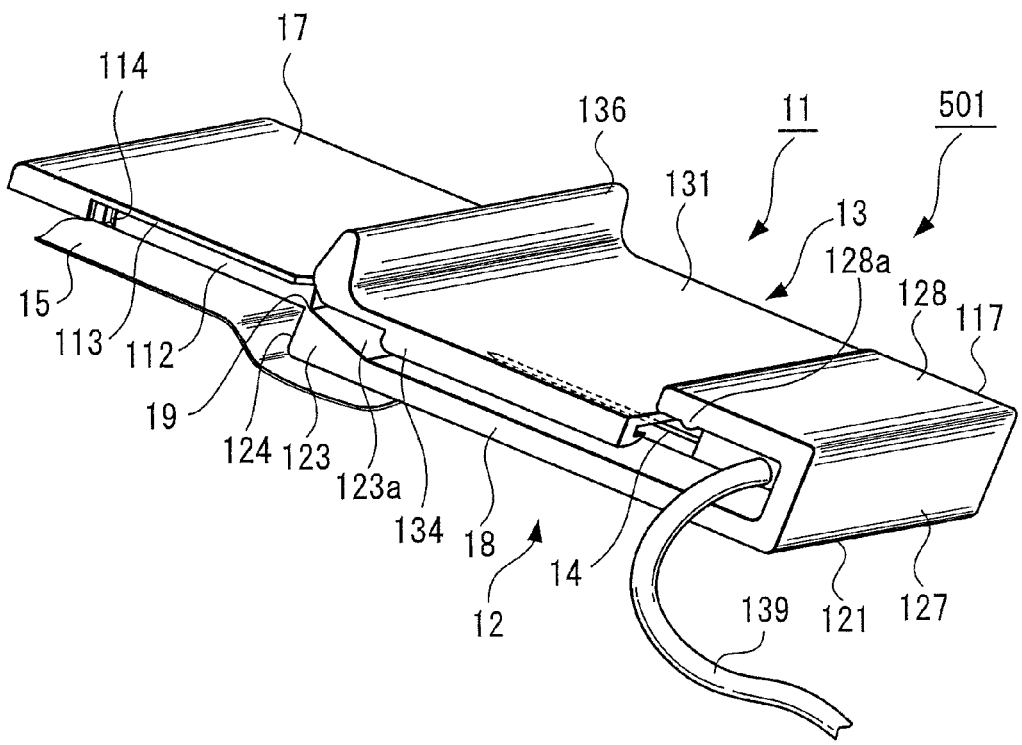
[FIG. 21] A diagram showing a sixth exemplified embodiment of a puncture device of the present invention and an exemplified embodiment of an administration device of the present invention which is a perspective view seen from the front side.
Figure 22:
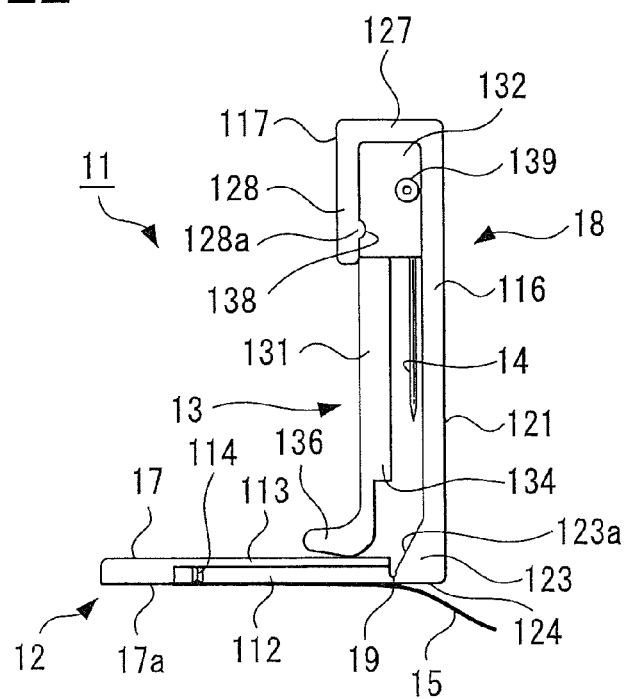
[FIG. 22] A right side elevational view (tip side of the positioning portion is made to be front side) of the puncture device shown in FIG. 21.

FIG. 21 and FIG. 22 are drawings explaining the sixth exemplified embodiment of the present invention. More specifically, FIG. 21 is a perspective view of a puncture device of the present invention, FIG. 22 is a side elevational view, FIG. 23 is an exploded perspective view, FIG. 24 is an enlarged view shown by enlarging the puncture needle, and FIG. 25 to FIG. 28 are explanatory diagrams for explaining the usage of the puncture device shown in FIG. 21.

Figure 23:
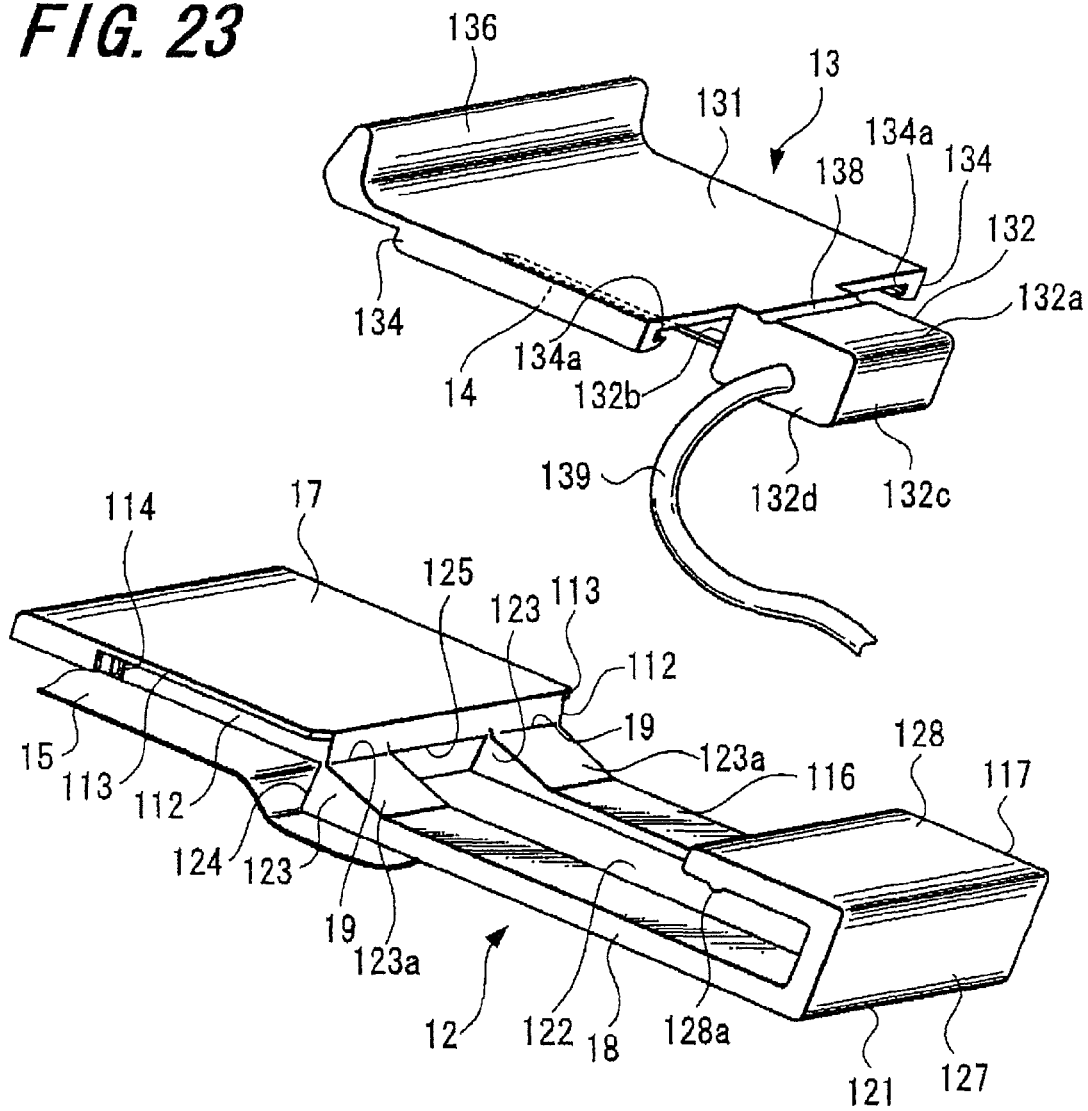
[FIG. 23] An exploded perspective view of the puncture device shown in FIG. 21.
Figure 24:
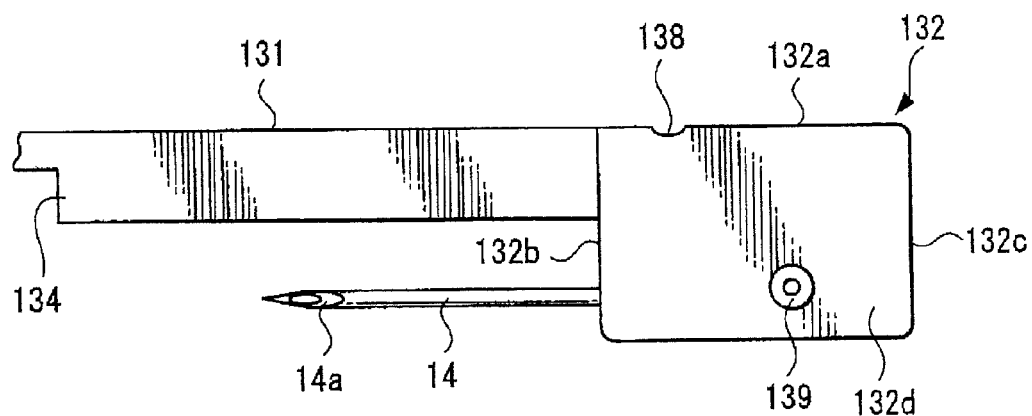
[FIG. 24] An enlarged view showing the puncture needle of the puncture device shown in FIG. 21 by being enlarged.

As shown in FIG. 21 to FIG. 23, a puncture device 11 is constituted by being provided with a base member 12, a slide member 13 supported by the base member 12 to be movable slidably, a puncture needle 14 mounted on the this slide member 13, an adhesive film 15 showing one embodiment of an adhesion member for fixing the base member 12 on the body surface F and the like. It should be noted that there are arranged, on the lower side of the body surface F on which the base member 12 is fixed, a stratum corneum SC, an epidermis E including the stratum corneum SC, a dermis D and a subcutis S in the form of laminae (see FIG. 25, etc.).

The base member 12 of the puncture device 11 is constituted by a positioning portion 17, a fixing portion 18, a pair of hinge portions 19, 19 interlinking the fixing portion 18 to the positioning portion 17 to be revolvable and the like. The positioning portion 17 of the base member 12 is formed by approximately a rectangular plate body and the side surface of one short side is interlinked to the fixing portion 18 through the pair of hinge portions 19, 19. The lower surface of this positioning portion 17 is made to be a skin fixing plane 17a for fixing the positioning portion 17 on the body surface F by being appressed thereto.

Also, there are provided on both the side surfaces of the long sides of the positioning portion 17 with notches 112, 112 from the edge portion of the hinge portion 19 side until an intermediate portion in the longitudinal direction thereof and thereby, guide rails 113, 113 showing one embodiment of first guide means are formed. These guide rails 113, 113 are engaged with engagement grooves 134a, 134a to be described hereinafter of the slide member 13, respectively. Also, there are provided at the edge portions on the opposite side with respect to the hinge portions 19 of the respective notches 112, 112 with stopper protrusion portions 114, 114 for latching the sliding motion of the slide member 13, respectively (only one side is shown in FIG. 21 etc.).

The fixing portion 18 of the base member 12 is formed by approximately a rectangular plate body and is constituted by a main body plate 116 in which the short side thereof is set to have length equivalent to the length on the short side of the positioning portion 17, a latch piece 117 which is continuous with one side of this main body plate 116 and the like. The lower surface of the main body plate 116 of the fixing portion 18 is a plane for fixing the fixing portion 18 on the body surface F by being appressed thereto and is made to be a contact surface 121. The upper surface of the main body plate 116 is formed with a slide guide groove 122 showing one embodiment of second guide means which is extended approximately at the central portion in the width direction along the longitudinal direction. This slide guide groove 122 is engaged with a needle retaining portion 132 to be described hereinafter of the slide member 13 slidably.

The puncture needle moving means retaining the puncture needle 14 to be movable is constituted by the slide member 13 and the fixing portion 18. Also, the skin deforming means for deforming the skin is constituted by the base member 12, the positioning portion 15 and the hinge portion 19.

Further, on one short side of the main body plate 116 it is provided with a pair of interlink portions 123, 123 projecting upward from both the sides of the slide guide groove 122. There are formed on the pair of interlink portions 123, 123 with inclined surfaces 123a, 123a inclined so as to become taller sequentially toward the tip side and the tip portions thereof are interlinked to the lower portion of the side surface of the positioning portion 17 through the pair of hinge portions 19, 19. Thereby, there are formed between the pair of interlink portions 123, 123 of the main body plate 116 with an opening window 125 showing one embodiment of a through-hole to be passed through by the puncture needle 14 mounted on the slide member 13. Then, the side surface on the pair of interlink portions 123, 123 side of the main body plate 116 is made to be a depressing surface 124 for uplifting the skin.

The latch piece 117 of the fixing portion 18 is composed of a rising portion 127 projecting approximately perpendicularly by being continuous with the main body plate 116 and a flange portion 128 which is developed approximately perpendicularly from this rising portion 127 and faces to the main body plate 116. The rising portion 127 of this latch piece 117 is contacted with the needle retaining portion 132 of the slide member 13. Also, there is provided on the surface of the flange portion 128 facing to the upper surface of the main body plate 116 with a latch protrusion portion 128a and this latch protrusion portion 128a is engaged with a latch concave portion 138 to be described hereinafter of the needle retaining portion 132.

Also, the hinge portions 19, 19 of the base member 12 is set to have lower stiffness as compared with the positioning portion 17 or the fixing portion 18. Depending on this configuration, the fixing portion 18 is made to be revolvable in the angular range of approximately 90 degree from approximately a perpendicular state with respect to the positioning portion 17 (state shown in FIG. 22 etc.) until approximately a parallel state with respect to the positioning portion 17 (state shown in FIG. 23 etc.).

It is possible for the material of such a base member 12 to cite, for example, an ABS (acrylonitrile-butadiene-styrene resin). However, the material of the base member 12 is not limited by the ABS and it is needless to say that synthetic resins of engineering plastic or others can be applied thereto and it is also possible to use metals such as aluminum alloy or the like other than the synthetic resins.

As shown in FIG. 22, FIG. 23 and the like, the adhesive film 15 for bonding and fixing the base member 12 on the body surface F is glued on the lower surface of the positioning portion 17 of the base member 12. The length in the width direction of this adhesive film 15 is set to be longer than the length in the width direction of the base member 12, and the length in the longitudinal direction thereof is set to be a length corresponding to the length from the midway portion of the positioning portion 17 until the midway portion of the contact surface 121 constituted by a plane which is formed at the fixing portion 18 by way of the hinge portions 19, 19. Then, the portion which does not correspond to the positioning portion 17 spreads in a skirt shape.

It should be noted for the adhesive film 15 relating to the present invention that it is not limited by the shape as mentioned above and it may be constituted such that the length in the width direction is set equivalently with the length in the width direction of the base member 12 and as shown in FIG. 22, the whole surface which reaches from the midway portion of the contact surface 121 of the fixing portion 18 to the midway portion of the positioning portion 17 through the hinge portions 19, 19 is to be glued on the base member 12 beforehand.

It is possible for the material of the adhesive film to cite polyethylene terephthalate (PET) and polyethylene which do not expand or contract and the like, but it is not limited by this and it is possible to use various kinds of materials such as polyurethane and others which are used as this kind of adhesive film. Also, it is preferable for the thickness of the adhesive film 15 to be around 1 micron to 30 microns, but it should be noted that even an adhesive film having thickness of more than 30 microns can be applied thereto.

The slide member 13 showing one embodiment of retaining means for retaining the puncture needle 14 is constituted, as shown in FIG. 23 etc., by being provided with a slide plate 131 forming approximately a rectangular plate body, a needle retaining portion 132 which is continuous with one side of this slide plate 131 and the like. The slide plate 131 of the slide member 13 is provided with a pair of side surface pieces 134, 134 which are continuous with the long sides respectively and project to the lower side and engagement grooves 134a, 134a are formed on the mutually facing surfaces of these side surface pieces 134, 134.

Each of the engagement grooves 134a, 134a of the pair of side surface pieces 134, 134 are slidably engaged with each of the guide rails 113, 113 of the base member 12. Also, the pair of side surface pieces 134, 134 are provided with stopper concave portions which are not shown respectively at the positions corresponding to the respective stopper protrusion portions 114, 114 of the base member 12 and the sliding motion of the slide member 13 is latched by engaging the respective stopper protrusion portions 114, 114 with these stopper concave portions.

Further, the slide plate 131 of the slide member 13 is provided with an operation protrusion portion 136 which is continuous with the one short side and projects upward. This operation protrusion portion 136 is provided for making it easy to be operated by hooking a finger thereon when slide-operating the slide member 13. Then, the needle retaining portion 132 is arranged on the opposite side with respect to the operation protrusion portion 136 of the of the slide plate 131.

The needle retaining portion 132 of the slide member 13 is made to be approximately a quadrangular hollow housing and is constituted by an upper surface 132a forming the same surface as the upper surface of the slide plate 131, a front face 132b on which the puncture needle 14 is mounted, a back face 132c on the opposite side of the front face 132b, a right side surface 132d forming a side surface on the right side by seeing the front face 132b from the tip side of the slide plate 131, and a left side surface and a bottom face which do not appear in the figure. Then, by engaging the bottom face side of the needle retaining portion 132 with the slide guide groove 122 of the base member 12 slidably, the slide member 13 is supported on the base member 12 to be slide-movable.

There is provided on the upper surface 132a of the needle retaining portion 132 with a latch concave portion 138 extended in the direction parallel with the width direction of the slide plate 131. The slide moving of the slide member 13 is latched by engaging the latch protrusion portion 128a of the base member 12 with this latch concave portion 138. More specifically, the locking means for locking the movement of the slide member 13 which is the retaining means is constituted by the latch concave portion 138 provided on the upper surface 132a of the needle retaining portion 132, the latch protrusion portion 128a of the fixing portion 18, the stopper protrusion portions 114, 114 of the positioning portion 17 and respective stopper concave portions which are provided, although not shown, on the side surface piece 134 of the slide plate 131.

The puncture needle 14 mounted on the front face 132b of the needle retaining portion 132 forms, as shown in FIG. 24, a hollow needle and it is arranged such that the axis center thereof coincides with the direction to which the slide plate 131 is slided along the side surface pieces 134, 134. With respect to the diameter and the length of this puncture needle 14, although not being limited in particular, it is preferable for the diameter thereof to be around 0.1 mm to 3 mm and it is preferable for the length thereof to be around 2 mm to 20 mm. Also, it is possible for the material of the puncture needle 14 to cite, for example, stainless steel, but it is not limited by this and it is possible to use aluminum, aluminum alloy, titanium, titanium alloy or other metals. A blade surface 14a, as shown in FIG. 24, is formed at the tip of the puncture needle 14. The blade surface 14a is faced to a direction horizontally perpendicular to the moving direction of the slide member (retaining means) 13. According to the configuration that the blade surface 14a is directed to the aforesaid direction, when the puncture needle 14 is made to go into the skin, the blade edge of the puncture needle 14 is prevented from being bended to the depth direction of the skin and it is possible to place it at an accurate position.

Further, a tube 139 is mounted on the right side surface 132d of the needle retaining portion 132. One terminal of the tube 139 is inserted into the inside thereof from a through-hole provided on the right side surface 132d of the needle retaining portion 132 and is communicated with the puncture needle 14 mounted on the front face 132b in the inside thereof. Also, the other terminal of the tube 139 is, although not shown, made to communicate with an injection device such as an injector, a liquid transmission pump or the like.

It is possible for the material of the slide member 13 to cite, for example, an ABS (acrylonitrile-butadiene-styrene resin). However, the material of the slide member 13 is not limited by the ABS and synthetic resins of engineering plastic or others can be applied thereto.

According to the puncture device 11 having such a constitution, it is possible, for example, in a way described as follows to stick the puncture needle 14 into the dermis D which constitutes a portion of the skin and to inject liquid of medicinal solution or the like thereto.

The state before the skin is punctured, more specifically, the state of the puncture device 11 before being used is, as shown in FIG. 22, made to be a state in which the fixing portion 18 is approximately perpendicular with respect to the positioning portion 17. In this state, the needle retaining portion 132 of the slide member 13 is engaged with the engagement piece 117 of the fixing portion 18. At that time, the back face 132c of the needle retaining portion 132 is contacted to the rising portion 127 of the engagement piece 117 and at the same time, the latch concave portion 138 of the needle retaining portion 132 is engaged with the latch protrusion portion 128a of the engagement piece 117, so that the slide-movement of the slide member 13 is latched.

The fixing portion 18 of such a puncture device 11 is grasped by fingers, the positioning portion 17 and the depressing surface 124 of the fixing portion 18 are pressure-attached onto the body surface F which is the most outer framework of the skin and are adhesively fixed thereon by the adhesive film 15. At that time, the puncture needle 14 mounted on the slide member 13 is positioned between the slide plate 131 and the main body plate 116 of the fixing portion 18, so that it is possible to prevent the finger grasping the puncture device 11 from touching the puncture needle 14 or to prevent the puncture needle 14 from puncturing the finger accidentally and it is possible to maintain the puncture needle 14 in a clean state.

Figure 26:
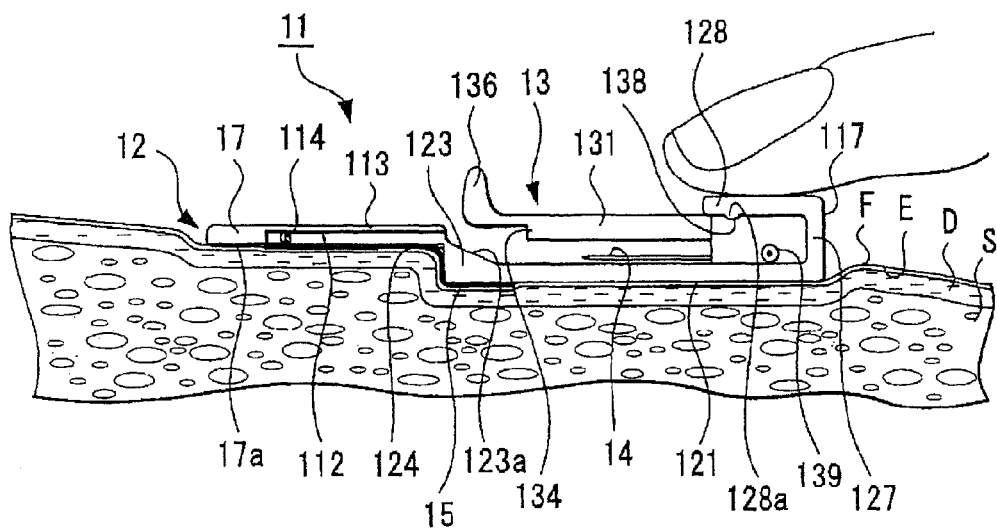
[FIG. 26] An explanatory diagram indicating a state in which a fixing portion of the puncture device shown in FIG. 21 is turned to the body surface side and the contact surface thereof is bonded to the body surface.

Next, as shown in FIG. 26, the fixing portion 18 is turned by approximately 90 degree and the skin bond to the positioning portion 17 is uplifted. More specifically, the fixing portion 18 is turned by approximately 90 degree and by obtaining a state in which the depressing surface 124 is made to be orthogonal with respect to the positioning portion 17, the skin bonded to the depressing surface 124 is depressed and the skin bonded to the positioning portion 17 is uplifted. Thereby, the epidermis E including the stratum corneum SC, the dermis D and the subcutis S are pulled upward respectively and the skin is uplifted to the vertical direction with respect to the body surface F.

Concurrently with this, the contact surface 121 of the fixing portion 18 is bonded and fixed on the body surface F by means of the adhesive film 15. Thereby, depending on a fact that the skin is deformed and uplifted, the position of the contact surface 121 provided on the fixing portion 18 and the position of the skin fixing plane 17a formed on the positioning portion 17 become different in the height direction and a step is formed between the skin bonded to the positioning portion 17 and the skin bonded or appressed to the contact surface 121 of the fixing portion 18. Then, by relatively setting the height of the depressing surface 124 and the mounting position of the puncture needle 14 or the like, the height of the dermis D of the skin bonded to the positioning portion 17 and the height of the puncture needle 14 are made to coincide with each other.

Figure 27:
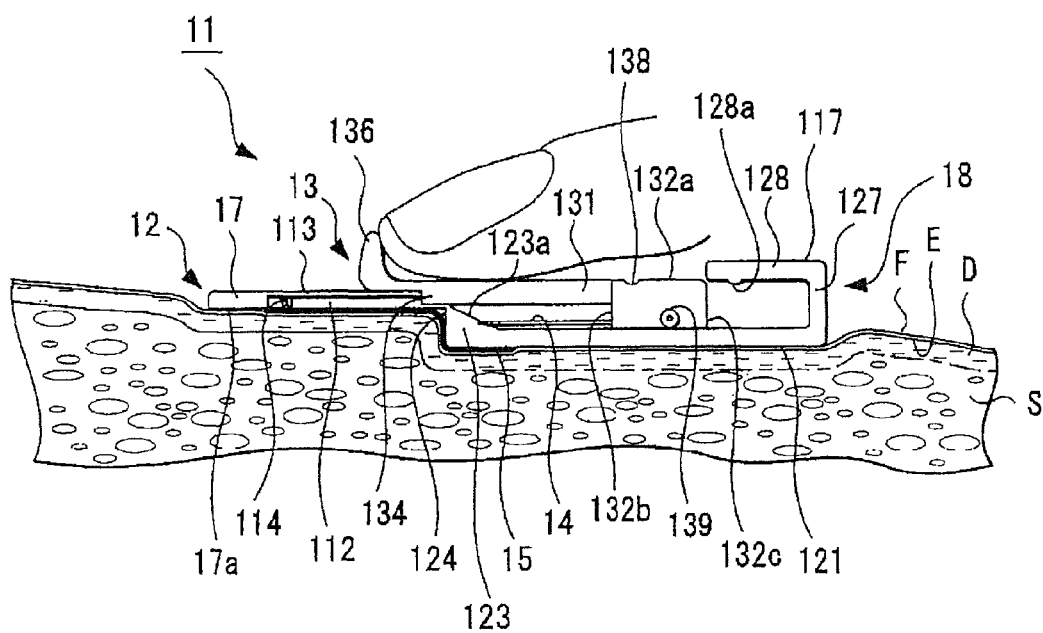
[FIG. 27] An explanatory diagram indicating a state in which a slide member of the puncture device shown in FIG. 21 is slided to the positioning portion side.

Subsequently, as shown in FIG. 27, a finger is hooked on the operation protrusion portion 136 and the slide member 13 is depressed to the positioning portion 17 side. Thereby, the latch concave portion 138 of the needle retaining portion 132 is unfastened from the latch protrusion portion 128a of the engagement piece 117 and it is possible to slide the slide member 13 to the positioning portion 17 side. When the slide member 13 is slided, first, the respective engagement grooves 134a, 134a provided on the pair of side surface pieces 134, 134 of the slide member 13 are engaged with the pair of guide rails 113, 113 of the positioning portion 17.

At that time, the slide member 13 is slided along the slide guide groove 122 of the fixing portion 18 by means of the needle retaining portion 132, so that it is possible to easily engage respective engagement grooves 134a, 134a of the slide member 13 with the pair of guide rails 113, 113 of the positioning portion 17. In this manner, the slide member 13 is guided by the slide guide groove 122 of the fixing portion 18 and the pair of guide rails 113, 113 of the positioning portion 17 and is slided to the positioning portion 17 side.

Figure 28:
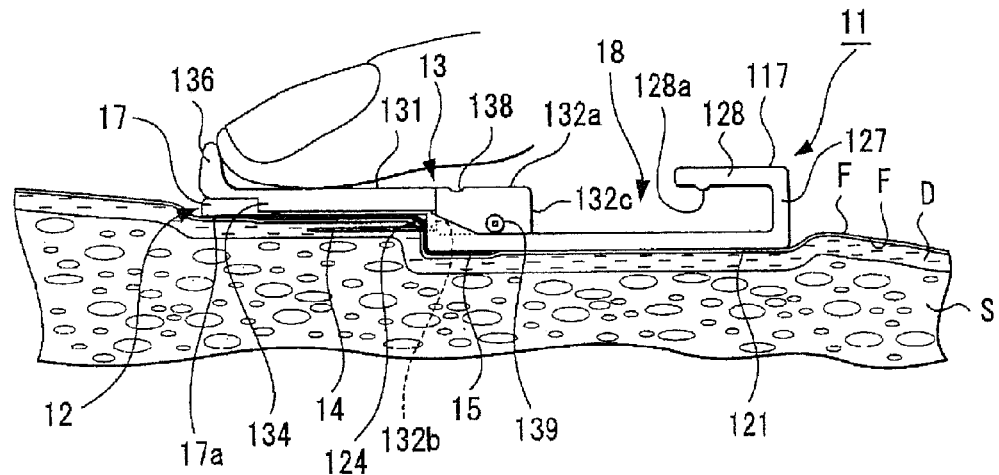
[FIG. 28] An explanatory diagram indicating a state in which the slide member is further slided from the state shown in FIG. 27 and the puncture needle is stuck to the dermis of the skin.

Thereafter, the slide member 13 is further slided and, as shown in FIG. 28, the front face 132b of the needle retaining portion 132 is contacted to the positioning portion 17. Thereby, the puncture needle 14 is moved approximately in parallel with the contact surface 121, passes through the opening window 125 (see FIG. 23) of the fixing portion 18, which is provided at the step portion and is stuck concurrently from the body surface F facing to the opening window 125 thereof to the dermis D, and the puncture operation by means of the puncture device 11 is terminated.

At that time, the puncture needle 14 is stuck approximately perpendicularly with respect to the body surface F facing to the opening window 125, so that the intrusion direction of the blade edge is never deviated to the depth direction of the skin and it is possible to carry out the puncture to the dermis D certainly. Further, the adhesive film 15 is glued also on the body surface F facing to the opening window 125 of the fixing portion 18, so that it is possible when sticking the puncture needle 14 to prevent or repress the whole skin from being sunk elastically and it is possible to stick the puncture needle 14 into the skin easily.

Also, when the front face 132b of the needle retaining portion 132 is contacted to the positioning portion 17, the respective stopper concave portions which are provided on the pair of side surface piece 134, 134 of the slide member 13 although not shown are engaged with the stopper protrusion portions 114, 114 of the positioning portion 17. For that reason, it is possible to latch the slide-movement to the fixing portion 18 side of the slide member 13. Further, the front face 132b of the needle retaining portion 132 is contacted with the positioning portion 17, so that it is possible to prevent the fixing portion 18 from jumping up. Thereby, even if the finger is released, it is possible for the puncture device 11 to be retained in a state in which the puncture needle 14 is stuck in the dermis D of the uplifted skin (state shown in FIG. 28) and it is possible to prevent the puncture needle 14 from dropping out abruptly.

When the puncture operation by means of the puncture device 11 is terminated, liquid such as medicinal solution or the like is sent to the tube 139 from the injection device such as an injector, a liquid transmission pump or the like which is not shown and is injected into the dermis D through the puncture needle 14. Thereafter, when it is desired to detach the puncture device 11, first, fingers are hooked on the operation protrusion portion 136 and the slide member 13 is to be depressed to the fixing portion 18 side. Thereby, the respective stopper concave portions of the slide member 13 are unfastened from the stopper protrusion portions 114, 114 of the positioning portion 17 and the slide member 13 becomes slide-movable to the fixing portion 18 side.

Next, the slide member 13 is slided and the back face 132c of the needle retaining portion 132 is contacted with the rising portion 127 of the latch piece 117. Thereby, the puncture needle 14 pulled out from the skin. At that time, the latch concave portion 138 of the needle retaining portion 132 is engaged with the latch protrusion portion 128a of the engagement piece 117, so that the slide-movement of the slide member 13 is latched.

Thereafter, the base member 12 is exfoliated from the body surface F and the detaching of the puncture device 11 is completed. At that time, it is possible to exfoliate it easily if a portion on which the adhesive film 15 of the positioning portion 17 is not mounted is pinched and lifted. Also, the slide member 13 retaining the puncture needle 14 is latched for the slide-movement, so that it is possible to prevent an accidental needlestick, an infection caused by that accidental needlestick or the like.

As explained above, according to the puncture device of this exemplified embodiment, in case of, for example, puncturing the dermis D, it is possible to lift the dermis D of the skin to an equivalent height as that of the puncture needle by turning the fixing portion in a state in which the positioning portion is adhesively fixed onto the body surface F and by uplifting the skin and it is possible to make the direction to which the axis center of the puncture needle thereof is extended and the direction to which the dermis D layer is extended to be approximately in parallel with each other.

As a result thereof, it becomes possible to lengthen the distance from the medical agent releasing aperture which exists at the needlepoint of the puncture needle until the epidermis E and the body surface F, so that it is possible to prevent the medical agent injected from the medical agent releasing aperture to the dermis D from flowing back [backward] and permeating the epidermis E or from leaking to the outside of the body surface F. Accordingly, it is possible to inject the medical agent into the dermis D certainly.

It should be noted that the above-described exemplified embodiments were explained by using examples in which the puncture needle is always stuck to the dermis D, but it is possible to use the puncture device of the present invention also in case of sticking to an intracutaneous area, a subcutis or further a muscle other than the dermis.

It should be noted for the skin deforming means of the present invention that it is not limited by the aforesaid exemplified embodiments and it is possible to cite configurations in which a predetermined portion of the skin is gathered and lifted by pushing the both sides thereof, the predetermined portion of the skin is hooked and lifted and the like.

Also, the puncture device of the present invention is not limited by the above-mentioned each exemplified embodiment and besides that, it is needless to say that various modifications or changes can be employed for the materials, the constitutions or the like in the region without departing from the configuration of the present invention.

Hereinafter, it will be explained with respect to modes for practicing an administration device of the present invention with reference to drawings, but the present invention is not limited by the following modes.

Figure 29:
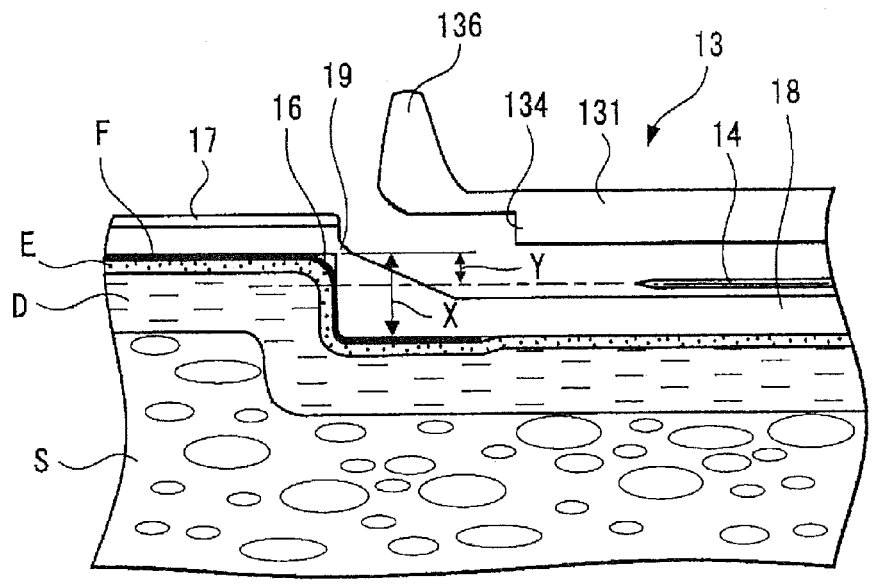
[FIG. 29] An explanatory diagram indicating a relation of depressing surface height of the puncture device shown in FIG. 21 and mounting position of the puncture needle.
Figure 30:
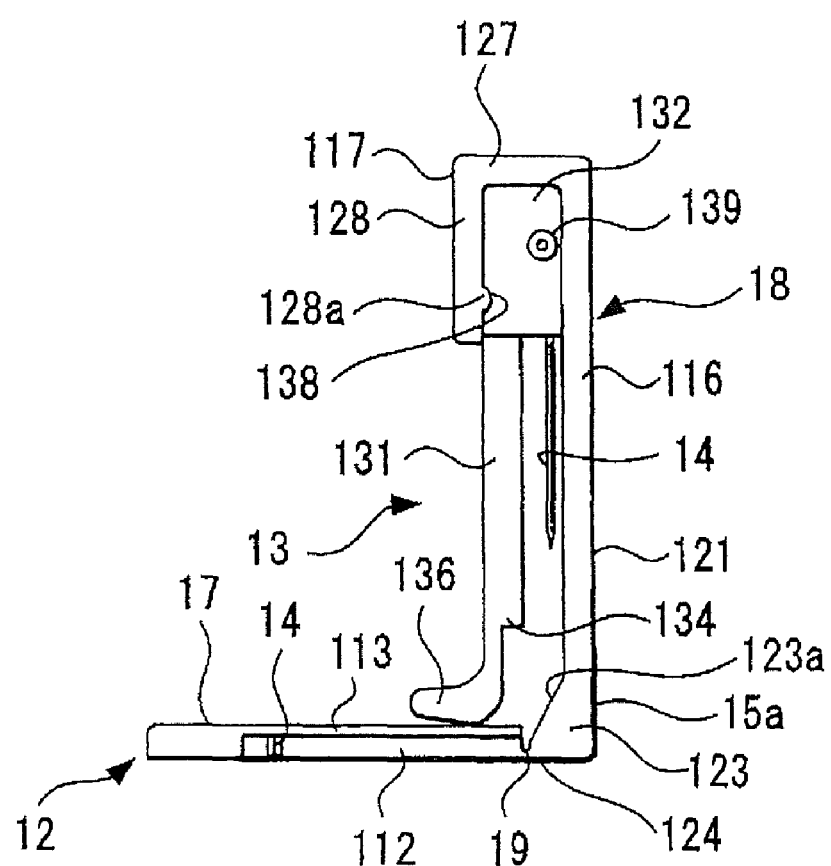
[FIG. 30] An explanatory diagram showing another embodiment of a mounting position of an adhesion member relating to the puncture device shown in FIG. 21.
Figure 31:
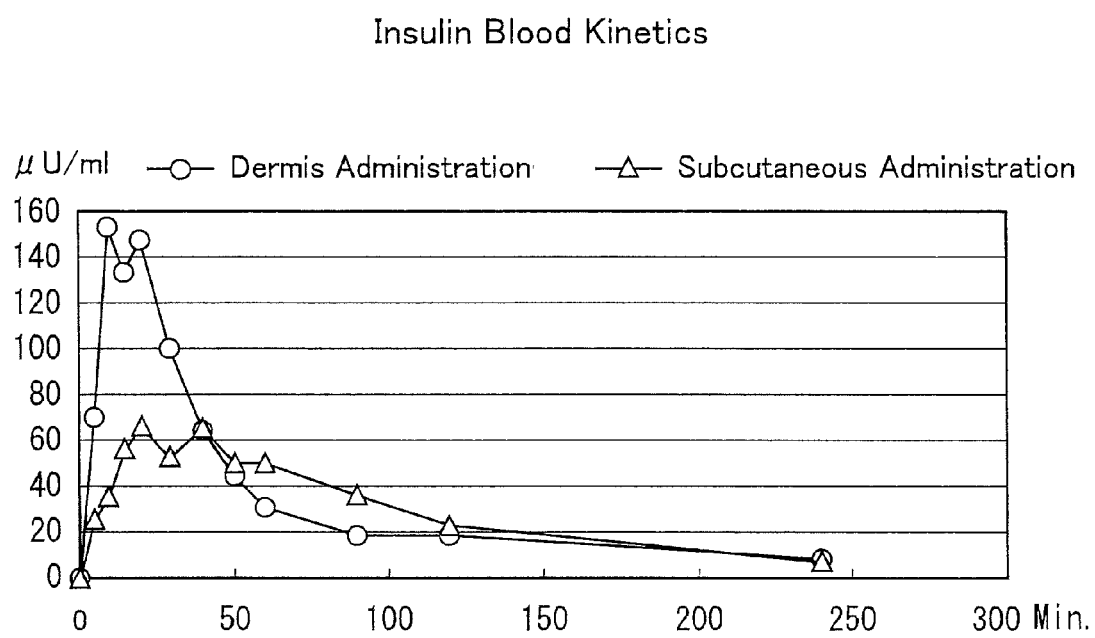
[FIG. 31] A diagram indicating a measured result of blood concentrations of a case in which insulin is administered to the dermis by using the administration device of the present invention and of a case in which insulin is administered into the subcutaneous by using a conventional device, which is a diagram showing a time curve of blood concentration.
Figure 32:
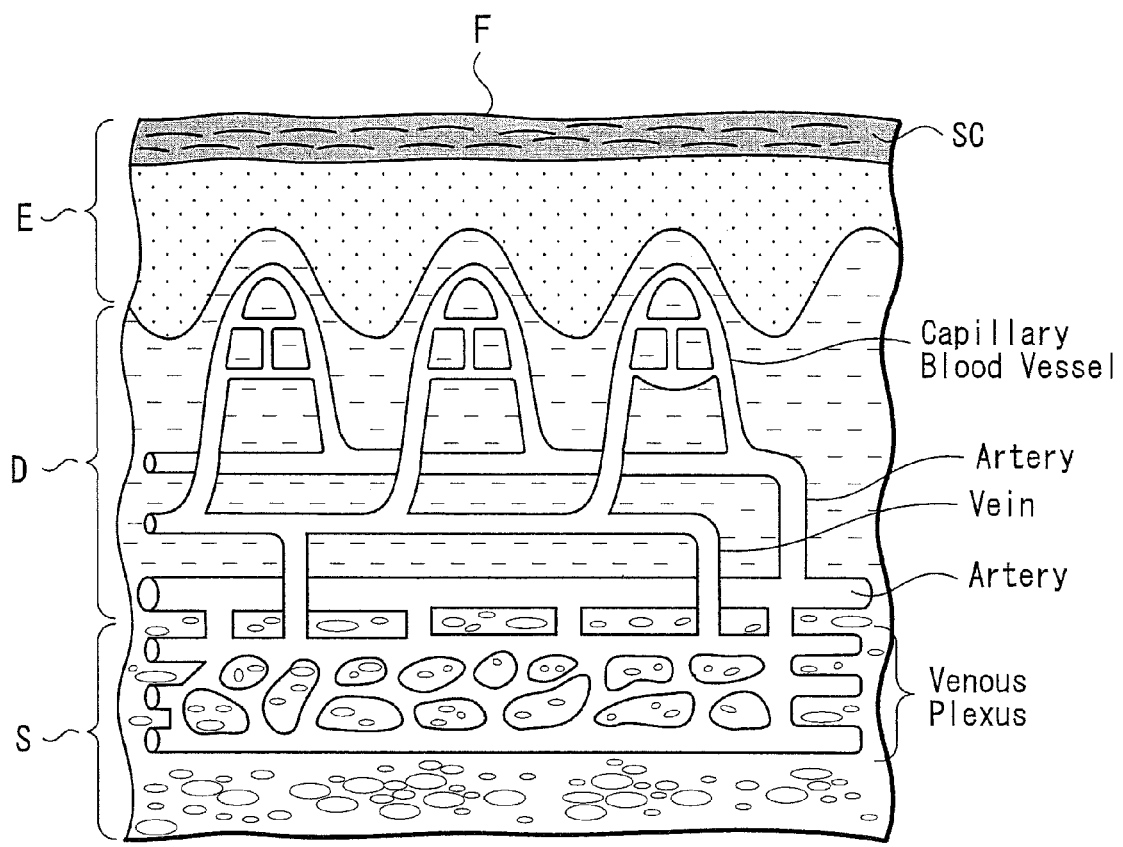
[FIG. 32] A cross-section view showing a general skin structure.

FIG. 21 is an explanatory diagram for explaining a first exemplified embodiment of an administration device of the present invention. FIG. 22 is a side elevational view of a puncture device constituting a portion of the administration device shown in FIG. 21. FIG. 23 is an exploded perspective view of the puncture device. FIG. 24 is an enlarged view showing the puncture needle of the puncture device by being enlarged. FIGS. 25 to 28 are explanatory diagrams for explaining the usage of the puncture device. FIG. 29 is an explanatory diagram in which a main portion of the puncture device shown in FIG. 21 is enlarged. FIG. 30 is an explanatory diagram showing another example of a mounting position of an adhesion member relating to the puncture device. FIG. 31 indicates a measured result of blood concentrations of a case in which insulin is administered to the dermis by using the administration device of the present invention and is a diagram showing a time curve of blood concentration.

As shown in FIG. 21 and the like, an administration device 501 showing a first exemplified embodiment of an administration device of the present invention is constituted by being provided with a puncture device 11 and an injection device (not shown) in communication with one puncture needle 14 of this puncture device 11.

As shown in FIG. 21 to FIG. 23, the puncture device 11 is constituted by being provided with a base member 12, a slide member 13 supported by the base member 12 slidably, an adhesive film 15 showing one embodiment of an adhesion member for fixing the base member 12 on the body surface F and the like. It should be noted that there are arranged, on the lower side of the body surface F on which the base member 12 is fixed, a stratum corneum SC, an epidermis E including the stratum corneum SC, a dermis D and a subcutis S in the form of laminae (see FIG. 25, etc.).

The base member 12 of the puncture device 11 is constituted by a positioning portion 17, a fixing portion 18, a pair of hinge portions 19, 19 interlinking the fixing portion 18 to the positioning portion 17 to be revolvable and the like. The positioning portion 17 of the base member 12 forms approximately a rectangular plate body in which one side surface of the short sides thereof is interlinked to the fixing portion 18 through the pair of hinge portion 19, 19. The lower surface of this positioning portion 17 is made to be a plane for firmly attaching and fixing the positioning portion 17 on to the body surface F.

Also, there are provided on both the side surfaces of the long sides of the positioning portion 17 with notches 112, 112 from the edge portion of the hinge portion 19 side until an intermediate portion in the longitudinal direction thereof and thereby, guide rails 113, 113 showing one embodiment of first guide means are formed. These guide rails 113, 113 are engaged with engagement grooves 134a, 134a to be described hereinafter of the slide member 13, respectively. Also, there are provided at the edge portions on the opposite side with respect to the hinge portions 19 of the respective notches 112, 112 with stopper protrusion portions 114, 114 for latching the sliding motion of the slide member 13, respectively (only one side is shown in FIG. 21 etc.).

As shown in FIG. 23, the fixing portion 18 of the base member 12 is formed by approximately a rectangular plate body and is constituted by a main body plate 116 in which the short side thereof is set to have length equivalent to the length on the short side of the positioning portion 17, a latch piece 117 which is continuous with one side of this main body plate 116 and the like. The lower surface of the main body plate 116 is a plane for fixing the fixing portion 18 on the body surface F by being appressed thereto and is made to be a contact surface 121. The upper surface of the main body plate 116 is formed with a slide guide groove 122 showing one embodiment of second guide means which is extended approximately at the central portion in the width direction along the longitudinal direction. This slide guide groove 122 is engaged with a needle retaining portion 132 to be described hereinafter of the slide member 13 slidably.

Further, on one short side of the main body plate 116 it is provided with a pair of interlink portions 123, 123 projecting upward from both the sides of the slide guide groove 122.

There are formed on the pair of interlink portions 123, 123 with inclined surfaces 123a, 123a inclined so as to become taller sequentially toward the tip side and those tip portions are interlinked to the lower portion of the side surface of the positioning portion 17 through the pair of hinge portions 19, 19. Thereby, there are formed between the pair of interlink portions 123, 123 of the main body plate 116 with an opening window 125 showing one embodiment of a through-hole to be passed through by the puncture needle 14 mounted on the slide member 13. Then, the side surface on the pair of interlink portions 123, 123 side of the main body plate 116 is made to be a depressing surface 124 for uplifting the skin.

The latch piece 117 of the fixing portion 18 is composed of a rising portion 127 projecting approximately perpendicularly by being continuous with the main body plate 116 and a flange portion 128 which is developed approximately perpendicularly from this rising portion 127 and faces to the main body plate 116. The rising portion 127 of this latch piece 117 is contacted with the needle retaining portion 132 of the slide member 13. Also, there is provided on the surface of the flange portion 128 facing to the upper surface of the main body plate 116 with a latch protrusion portion 128a and this latch protrusion portion 128a is engaged with a latch cocave portion 138 to be described hereinafter of the needle retaining portion 132.

The hinge portions 19, 19 of the base member 12 is set to have lower stiffness as compared with the positioning portion 17 or the fixing portion 18. Depending on this configuration, the fixing portion 18 is made to be revolvable in the angular range of approximately 90 degree from approximately a perpendicular state with respect to the positioning portion 17 (state shown in FIG. 22 etc.) until approximately a parallel state with respect to the positioning portion 17 (state shown in FIG. 23 etc.).

It is possible for the material of such a base member 12 to cite, for example, an ABS (acrylonitrile-butadiene-styrene resin). However, the material of the base member 12 is not limited by the ABS and it is needless to say that synthetic resins of engineering plastic or others can be applied thereto and it is also possible to use metals such as aluminum alloy or the like other than the synthetic resins.

As shown in FIG. 22, FIG. 23 and the like, the adhesive film 15 for bonding and fixing the base member 12 on the body surface F is glued on the lower surface of the positioning portion 17 of the base member 12. The length in the width direction of this adhesive film 15 is set to be longer than the length in the width direction of the base member 12, and the length in the longitudinal direction thereof is set to be a length corresponding to the length from the midway portion of the positioning portion 17 until the midway portion of the contact surface 121 of the fixing portion 18 by way of the hinge portions 19, 19. Then, the portion which does not correspond to the positioning portion 17 spreads in a skirt shape.

It should be noted for the adhesive film relating to the present invention that it is not limited by the shape of the above-mentioned adhesive film 15. For example, as shown in FIG. 30, it is also possible to use an adhesive film 15a in which the length of the width direction is set to be equivalent with the length of the width direction of the base member 12. Then, it is allowed for such an adhesive film 15a to glue the whole surface thereof on the base member 12 beforehand. At that time, the adhesive film 15a is glued so as to reach the midway portion of the contact surface 121 of the fixing portion 18 from the midway portion of the positioning portion 17 by way of the hinge portions 19, 19.

It is possible for the material of the adhesive film to cite polyethylene terephthalate (PET) and polyethylene which do not expand or contract and the like, but it is not limited by this and it is possible to use various kinds of materials such as polyurethane and others which are used as this kind of adhesive film. Also, it is preferable for the thickness of the adhesive film 15 to be around 1 micron to 30 microns, but it should be noted that even an adhesive film having thickness of more than 30 microns can be applied thereto.

The slide member 13 showing one embodiment of retaining means for retaining the puncture needle 14 is constituted, as shown in FIG. 23 and the like, by being provided with a slide plate 131 forming approximately a rectangular plate body, a needle retaining portion 132 which is continuous with one side of this slide plate 131 and the like. The slide plate 131 of the slide member 13 is provided with a pair of side surface pieces 134, 134 which are continuous with the long sides respectively and project to the lower side and engagement grooves 134a, 134a are formed respectively on the mutually facing surfaces of these side surface pieces 134, 134.

Each of the engagement grooves 134a, 134a of the pair of side surface pieces 134, 134 are slidably engaged with each of the guide rails 113, 113 of the base member 12. Also, the pair of side surface pieces 134, 134 are provided with stopper concave portions which are not shown respectively at the positions corresponding to the respective stopper protrusion portions 114, 114 of the base member 12. More specifically, the sliding motion of the slide member 13 is latched by engaging the respective stopper concave portions which are not shown with the respective stopper protrusion portions 114, 114 of the base member 12.

Further, the slide plate 131 of the slide member 13 is provided with an operation protrusion portion 136 which is continuous with the one short side and projects upward. This operation protrusion portion 136 is provided for making it easy to be operated by hooking a finger thereon when slide-operating the slide member 13. Then, the needle retaining portion 132 is arranged on the opposite side with respect to the operation protrusion portion 136 of the of the slide plate 131.

The needle retaining portion 132 of the slide member 13 is made to be approximately a quadrangular hollow housing and is constituted by an upper surface 132a forming the same surface as the upper surface of the slide plate 131, a front face 132b on which the puncture needle 14 is mounted, a back face 132c on the opposite side of the front face 132b, a right side surface 132d forming a side surface on the right side by seeing the front face 132b from the tip side of the slide plate 131, and a left side surface and a bottom face which do not appear in the figure. Then, by engaging the bottom face side of the needle retaining portion 132 with the slide guide groove 122 of the base member 12 slidably, the slide member 13 is supported on the base member 12 to be slidable.

There is provided on the upper surface 132a of the needle retaining portion 132 with a latch concave portion 138 extended in the direction parallel with the width direction of the slide plate 131. It is constituted such that the sliding of the slide member 13 is latched by engaging this latch concave portion 138 with the latch protrusion portion 128a of the base member 12. More specifically, the locking means for locking the movement of the slide member 13 is constituted by the latch concave portion 138 of the needle retaining portion 132, the latch protrusion portion 128a of the fixing portion 18, the stopper protrusion portions 114, 114 of the positioning portion 17 and respective stopper concave portions, which are not shown, of the slide plate 131.

The puncture needle 14 mounted on the front face 132b of the needle retaining portion 132 forms, as shown in FIG. 24, a hollow needle. This puncture needle 14 is arranged such that the axis center thereof coincides with the direction to which the needle retaining portion 132 moves. With respect to the diameter and the length of the puncture needle 14, although not being limited in particular, it is preferable for the diameter thereof to be around 0.1 mm to 3 mm and it is preferable for the length thereof to be around 2 mm to 20 mm. Also, it is possible for the material of the puncture needle 14 to cite, for example, stainless steel, but it is not limited by this and it is possible to use aluminum, aluminum alloy, titanium, titanium alloy or other metals.

A blade surface 14a, as shown in FIG. 24, is formed at the tip of the puncture needle 14. The blade surface 14a is faced to a direction horizontally perpendicular to the moving direction of the slide member 13. In this manner, by directing the blade surface 14a of the puncture needle 14 to the aforesaid direction, when the puncture needle 14 is made to go into the skin, the blade edge of the puncture needle 14 is prevented from being bended to the depth direction of the skin and it is possible to place it at an accurate position.

Further, a tube 139 is mounted on the right side surface 132d of the needle retaining portion 132. One terminal of the tube 139 is inserted into the inside thereof from a through-hole provided on the right side surface 132d of the needle retaining portion 132 and is communicated with the puncture needle 14 mounted on the front face 132b in the inside thereof. Also, the other terminal of the tube 139 is made to communicate with an injection device which is not shown, such as an injector (syringe), a liquid transmission pump or the like.

It is possible for the material of the slide member 13 to cite, for example, an ABS (acrylonitrile-butadiene-styrene resin). However, the material of the slide member 13 is not limited by the ABS and synthetic resins of engineering plastic or others can be applied thereto.

According to the administration device 501 having such a constitution, it is possible, for example, in a way described as follows to stick the puncture needle 14 into the dermis D which constitutes a portion of the skin and to administer a substance of a medicinal solution, an immune cell or the like thereto.

As shown in FIG. 22, the puncture device 11 before the use of administration device 501 (before the skin is punctured) is made to be in a state in which the fixing portion 18 is approximately perpendicular with respect to the positioning portion 17. In this state, the latch concave portion 138 provided on the needle retaining portion 132 of the slide member 13 is engaged with the latch protrusion portion 128a of the latch piece 117, so that the slide-movement of the slide member 13 is latched.

Figure 25:
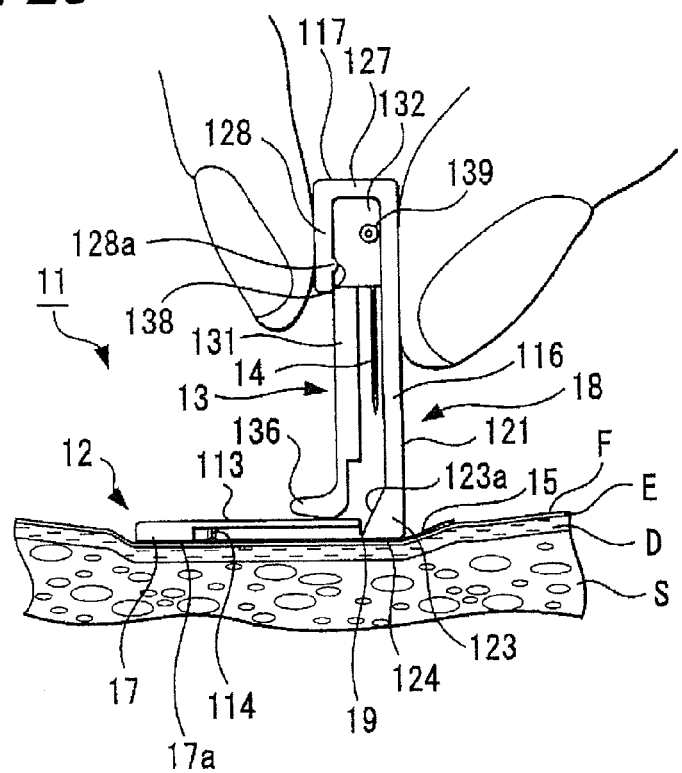
[FIG. 25] An explanatory diagram indicating a state in which a positioning portion and a depressing surface of the puncture device shown in FIG. 21 are bonded to the body surface.

In order to stick the puncture needle 14 into the dermis D, first, as shown in FIG. 25, the fixing portion 18 of the puncture device 11 is grasped by fingers, the depressing surface 124 of the fixing portion 18 and the positioning portion 17 are pressure-attached onto the body surface F which is the most outer framework of the skin. Thereby, the depressing surface 124 of the fixing portion 18 and the positioning portion 17 are bonded and fixed on the body surface F by means of the adhesive film 15. At that time, the puncture needle 14 mounted on the slide member 13 is positioned between the slide plate 131 and the main body plate 116 of the fixing portion 18. Therefore, it is possible to prevent the finger grasping the puncture device 11 from touching the puncture needle 14 or to prevent the puncture needle 14 from puncturing the finger accidentally and it is possible to maintain the puncture needle 14 in a clean state.

Next, as shown in FIG. 26, the fixing portion 18 is turned by approximately 90 degree and the skin bonded to the positioning portion 17 is uplifted. More specifically, the fixing portion 18 is turned by approximately 90 degree and by obtaining a state in which the depressing surface 124 is made to be orthogonal with respect to the positioning portion 17, the skin bonded to the depressing surface 124 is depressed and the skin bonded to the positioning portion 17 is uplifted. Thereby, the epidermis E including the stratum corneum SC, the dermis D and the subcutis S are pulled upward respectively and the skin is uplifted to the vertical direction with respect to the body surface F.

Concurrently with this, the contact surface 121 of the fixing portion 18 is bonded and fixed on the body surface F by means of the adhesive film 15. Thereby, a step is formed between the skin bonded to the positioning portion 17 and the skin bonded or appressed to the contact surface 121 of the fixing portion 18. At that time, the height of the depressing surface 124 and the mounting position of the puncture needle 14 are set relatively, so that it is constituted such that the height of the dermis D of the skin bonded to the positioning portion 17 and the height of the puncture needle 14 are to coincide with each other.

In this exemplified embodiment, as shown in FIG. 29, the height X of the depressing surface 124 is set to be approximately 3 mm and at the same time, the distance Y of the height direction from the tip of the depressing surface 124 until the axis center of the puncture needle 14 is set to be approximately 1 mm. Thereby, it is possible to make the height of the puncture needle 14 to coincide with the dermis D having width of around 1 mm to 2 mm which is positioned under the epidermis having width of around 0.06 mm to 0.1 mm from the body surface F bonded to the positioning portion 17. However, the height X of the depressing surface 124 and the distance Y from the tip portion of the depressing surface 124 until the puncture needle 14 relating to the present invention are not limited by the above-mentioned values and it is possible to make a relative setting such that the height of the dermis D when the skin is uplifted and the height of the puncture needle 14 are to coincide with each other.

Subsequently, as shown in FIG. 27, a finger is hooked on the operation protrusion portion 136 and the slide member 13 is depressed to the positioning portion 17 side. Thereby, the latch concave portion 138 of the needle retaining portion 132 is unfastened from the latch protrusion portion 128a of the engagement piece 117 and it is possible to slide the slide member 13 to the positioning portion 17 side. When the slide member 13 is slided, first, the respective engagement grooves 134a, 134a provided on the pair of side surface pieces 134, 134 of the slide member 13 are engaged with the pair of guide rails 113, 113 of the positioning portion 17.

At that time, the slide member 13 is slided along the slide guide groove 122 of the fixing portion 18 by means of the needle retaining portion 132, so that it is possible to easily engage respective engagement grooves 134a, 134a of the slide member 13 with the pair of guide rails 113, 113 of the positioning portion 17. In this manner, the slide member 13 is guided by the slide guide groove 122 of the fixing portion 18 and the pair of guide rails 113, 113 of the positioning portion 17 and is slided to the positioning portion 17 side.

Thereafter, the slide member 13 is further slided and, as shown in FIG. 28, the front face 132b of the needle retaining portion 132 is contacted to the positioning portion 17. The puncture needle 14 moves a distance of 1 to 15 mm, preferably, 3 to 10 mm by being slided the slide member 13. In this case, the puncture needle 14 passes through the opening window 125 (see FIG. 23) of the fixing portion 18 and is stuck from the body surface F facing to the opening window 125 thereof to the dermis D. More specifically, the puncture needle 14 has a portion to go into in parallel with the dermis layer. Thereby, the puncture operation by the puncture device 11 is finalized.

At that time, the puncture needle 14 is stuck approximately perpendicularly with respect to the body surface F facing to the opening window 125, so that the intrusion direction of the blade edge is never deviated to the depth direction of the skin and it is possible to carry out the puncture to the dermis D certainly. Further, the adhesive film 15 is glued also on the body surface F facing to the opening window 125 of the fixing portion 18, so that it is possible when sticking the puncture needle 14 to prevent or repress the whole skin from being sunk elastically and it is possible to stick the puncture needle 14 into the skin easily.

Also, when the front face 132b of the needle retaining portion 132 is contacted to the positioning portion 17, the respective stopper concave portions which are provided on the pair of side surface piece 134, 134 of the slide member 13 although not shown are engaged with the stopper protrusion portions 114, 114 of the positioning portion 17. Thereby, it is possible to latch the sliding to the fixing portion 18 side of the slide member 13. Further, the front face 132b of the needle retaining portion 132 is contacted with the positioning portion 17, so that it is possible to prevent the fixing portion 18 from jumping up. Thereby, even if the finger is released, it is possible for the puncture device 11 to be retained in a state in which the puncture needle 14 is stuck in the dermis D of the uplifted skin (state shown in FIG. 28) and it is possible to prevent the puncture needle 14 from dropping out abruptly.

When the puncture operation by means of the puncture device 11 is terminated, next, a substance such as a medicinal solution, an immune cell or the like is sent from an injection device such as an injector (syringe), a liquid transmission pump or the like which is not shown. Thereby, a substance such as a medicinal solution, an immune cell or the like is injected into the dermis D through the tube 139 and the puncture needle 14. Thereafter, when it is desired to detach the puncture device 11, first, fingers are hooked on the operation protrusion portion 136 and the slide member 13 is to be depressed to the fixing portion 18 side. Thereby, the respective stopper concave portions of the slide member 13 are unfastened from the stopper protrusion portions 114, 114 of the positioning portion 17 and the slide member 13 becomes slidable to the fixing portion 18 side.

Next, the slide member 13 is slided and the back face 132c of the needle retaining portion 132 is contacted with the rising portion 127 of the latch piece 117. Thereby, the puncture needle 14 pulled out from the skin. At that time, the latch concave portion 138 of the needle retaining portion 132 is engaged with the latch protrusion portion 128a of the engagement piece 117, so that the sliding of the slide member 13 is latched.

Thereafter, the base member 12 is exfoliated from the body surface F and the detaching of the puncture device 11 is completed. At that time, it is possible to exfoliate it easily if a portion on which the adhesive film 15 of the positioning portion 17 is not mounted is pinched and lifted. Also, the slide member 13 retaining the puncture needle 14 is latched for the sliding, so that it is possible to prevent an accidental needlestick, an infection caused by that accidental needlestick or the like.

An experiment (experiment 1) was carried out in which blood kinetics when administering ultra rapid acting type insulin into the dermis by means of the administration device 501 having a constitution as mentioned above and blood kinetics when administering it into the subcutaneous by means of a device used conventionally (hereinafter, referred to as "conventional devices") are compared.

Here, it will be explained with respect to the experiment 1. In the experiment 1, a plurality of pigs (approximately 10 Kg) fasted from one day before were made to be administration objects. Anesthesia was applied to these pigs and shearing hair was carried out at the administration regions for the medicinal solution and thereafter, for one group of the pigs, ultra rapid acting type insulin was administered into the dermis by means of the administration device 501 and for the other group of the pigs, it was administered into the subcutaneous by means of the conventional device, respectively. For the ultra rapid acting type insulin, Humalog 100 U/ml (produced by Eli Lilly & Co.) was used by making a dilution thereof in saline such that the applied dose becomes 0.5 U/kg and the administration volume becomes approximately 100 μl.

Also, for the puncture needle 14 of the administration device 501, a 33G needle (outer diameter is 0.2 mm manufactured by Terumo Corp.) was used and was set so as to be stuck as far as the 0.5 mm depth. Then, ultra rapid acting type insulin was filled in a 1 ml syringe showing one embodiment of the injection device jointed to the tube 139 and administration was carried out manually for 30 seconds. For the puncture needle of the conventional device, a 33G injector needle for injecting insulin to subcutaneous (needle length is 5 mm, manufactured by Terumo Corp.) was used. Then, the puncture needle of the conventional device was stuck perpendicularly with respect to the skin and similarly as the administration device 501, the ultra rapid acting type insulin was administered for 30 seconds.

In the administration of ultra rapid acting type insulin to the dermis and the subcutaneous as mentioned above, blood from the vein was collected before the administration and after the administration by 5 minutes, 10 minutes, 15 minutes, 20 minutes, 30 minutes, 40 minutes, 50 minutes, 60 minutes, 90 minutes, 120 minutes and 240 minutes respectively. Then, amounts of insulin in the circulating blood about the collected respective blood are measured by chemiluminescence assay (manufactured by Bayer Medical Ltd.). The measured result thereof is shown in FIG. 31 and table 1.

TABLE 1

| | Tmax (min) | Cmax (μU/ml) | AUC (0-4 h) | BA* |
|---|---|---|---|---|
| dermis (0.5 mm) | 10 | 151.8 | 132 | 12% |
| subcutaneous (5 mm) | 20 | 65.7 | 117.9 | — |

*with respect to subcutaneous administration

As shown in FIG. 31 and table 1, in case of administering insulin to the subcutaneous, the time to maximum blood concentration (Tmax) was 20 minutes and the maximum blood concentration (Cmax) was 65.7 μU/ml. Compared with that, the time to maximum blood concentration (Tmax) was 10 minutes and the maximum blood concentration (Cmax) was 151.8 μU/ml in a case where insulin was administered to the dermis. Owing to this fact, it is comprehended with respect to the administration of insulin to the dermis that the time to maximum blood concentration (Tmax) becomes shorter and the maximum blood concentration (Cmax) becomes higher as compared with the administration to the subcutaneous which was practiced conventionally.

the blood concentration time curve

Also, while the area under the blood concentration—time curve (AUC) with respect to the administration to the subcutaneous was 117.9 μU·h/ml, it was 132 μU·h/ml in case of the administration to the dermis. More specifically, the administration of insulin to the dermis makes the total amount of drug absorption in the body to become larger as compared with the administration to the subcutaneous, and relative bioavailability (BA) of the dermis administration to the subcutaneous administration is improved by 12%. From the fact mentioned above, it is comprehended that insulin is absorbed more efficiently and more rapidly and is distributed in the circulating blood when it is administered to the dermis than when it is administered to the subcutaneous.

Next, an experiment (experiment 2) was carried out in which it was measured the pressure under which the administration can be continued without leakage when administration liquid is administered to the dermis.

Here, it will be explained with respect to the experiment 2. In the experiment 2, similarly as in the experiment 1, a pig (approximately 10 Kg) fasted from one day before was made to be an administration object. Anesthesia was applied to this pig and shearing hair was carried out at the administration region for the medicinal solution and thereafter, one puncture needle was stuck by 0.5 mm depth of the skin by using the administration device 501 and pressure of the administered liquid was measured. There were prepared for the puncture needle located in the administration device 501 with two kinds of needles of a 33G needle having different diameters (smallest outer diameter is 0.2 mm, manufactured by Terumo Corp.) and a 30G needle for dental use (outer diameter is 0.3 mm, manufactured by Terumo Corp.), respective needles were located and the measuring was carry out. Also, physiological saline was used for the administration liquid.

Each of the 33G needle having different diameters and the 30G needle for dental use located in the administration device 501 was connected through a tube to an HPLC pump (LC-7A, manufactured by Hitachi High Technologies Co., Ltd.) and a pressure sensor (PA-860, manufactured by Nidec Copal Electronics Corp.) in which three-way joint was carried out. Then, the pressure was analyzed by monitoring the voltage outputted from the pressure sensor by using a PC data collection system (NR-500•NR-TH08, manufactured by Keyence Corporation). The administration condition is shown in table 2.

TABLE 2

| administration condition | | | | |
|---|---|---|---|---|
| skin depth mm | needle | Num. of needles | flow rate µl/min | administration region |
| 0.5 | 33G needle having diff. dia. | 1 | 100 | dorsal neck |
| 0.5 | 30G | 1 | 100 | dorsal neck |
| 0.5 | 33G needle having diff. dia. | 1 | 1000 | buttock |
| 0.5 | 30G | 1 | 1000 | buttock |
| 0.5 | 33G needle having diff. dia. | 1 | 2000 | buttock |
| 0.5 | 30G | 1 | 2000 | buttock |

As shown in the table 2, applied dose per unit time was made to be three kinds of 100 µl, 1000 µl and 2000 µl per one minute and the measurement was carried out twice for each. Also, the administration portions of the medicinal solution were set to be a dorsal neck portion and a buttock portion, and physiological saline was administered by 100 µl per one minute at the dorsal neck portion and was administered by 1000 µl and 2000 µl per one minute with respect to the buttock portion which has higher density of tissues than that of the dorsal neck portion and in which the administration condition is severe. The leakage of the physiological saline which was the administration liquid was judged by the naked eye and the each measurement was finished at the time when the leakage occurred. The measured result thereof is shown in table 3 to table 5.

TABLE 3

| Administration Speed and Pressure | | | | |
|---|---|---|---|---|
| | flow rate | aver- | psi (kg/cm$^2$) | |
| needle | µl/min | age | Max | Min |
| 33G needle having diff. dia. | 100 | 14 | 18 (1.2) | 10 (0.7) |
| 30G | 100 | 14 | 18 (1.3) | 9 (0.6) |
| 33G needle having diff. dia. | 1000 | 210 | 331 (23.3) | 88 (6.2) |
| 30G | 1000 | 308 | 400 (28.1) | 216 (15.2) |
| 33G needle having diff. dia. | 2000 | 396 | 432 (30.4) | 360 (25.3) |
| 30G | 2000 | 408 | 455 (32) | 360 (25.3) |

1 psi = 6895 Pa

TABLE 4

| Administration Speed and Leakage | | | | | |
|---|---|---|---|---|---|
| | flow | from | (%) | | |
| needle | rate µl/min | administration device | from skin | from both | time until leakage |
| 33G needle having diff. dia. | 100 | 0 | 0 | 0 | not leak for 20 min. |
| 30G | 100 | 0 | 0 | 0 | not leak for 20 min. |
| 33G needle having diff. dia. | 1000 | 50 | 100 | 50 | 2 min. & 10 sec. |
| 30G | 1000 | 0 | 50 | 0 | 2 min. & 18 sec. |
| 33G needle having diff. dia. | 2000 | 100 | 100 | 100 | 1 min. & 34 sec. |
| 30G | 2000 | 50 | 100 | 50 | 1 min. & 45 sec. |

TABLE 5

Administration Speed and Administration Amount

| needle | flow rate μl/min | administration volume | time until leakage |
|---|---|---|---|
| 33G needle having diff. dia. | 100 | 2 ml | not leak for 20 min. |
| 30G | 100 | 2 ml | not leak for 20 min. |
| 33G needle having diff. dia. | 1000 | 2.16 ml* | 2 min. & 10 sec. |
| 30G | 1000 | 2.3 ml* | 2 min. & 18 sec. |
| 33G needle having diff. dia. | 2000 | 3.13 ml* | 1 min. & 34 sec. |
| 30G | 2000 | 3.5 ml* | 1 min. & 45 sec. |

*means that leakage of administration device is included

As shown in the table 3, the maximum pressure became 18 psi in the case of locating the 30G needle for dental use in the administration device 501 and administering the physiological saline by 100 μl/min of flow velocity. Similarly, when the flow velocity was made to be 1000 μl/min, the maximum pressure became 400 psi and when the flow velocity was made to be 2000 μl/min, the maximum pressure became 455 psi.

Also, as shown in the table 4, in the case of administering physiological saline by 100 μl/min of flow velocity by using the 30G needle for dental use, it was possible to administer physiological saline at least for 20 minutes without leakage. Similarly, in the case of administering physiological saline by 1000 μl/min of flow velocity, it was possible to administer physiological saline for 2 minutes and 10 seconds without leakage. Then, when the flow velocity was made to be 1000 μl/min, probability in which the physiological saline leaked from the administration device 501 (from joint place of tube and HPLC pump) was 0% and probability of leakage from the skin was 50%.

Further, in the case of carrying out the administration by 2000 μl/min of flow velocity, it was possible to administer the physiological saline for 1 minute and 45 seconds without leakage. Then, when the flow velocity was made to be 2000 μl/min, probability in which the physiological saline leaked from the administration device 501 (from joint place of tube and HPLC pump) was 50% and probability of leakage from the skin was 100%.

Also, as shown in the table 5, the applied dose became 2 ml in the case of administering the physiological saline by 100 μl/min of flow velocity by using the 30G needle for dental use. Similarly, when the flow velocity was made to be 1000 μl/min, the applied dose of the physiological saline became 2.3 ml and when the flow velocity was made to be 2000 μl/min, it became 3.5 ml. On the other hand, also with respect to the 33G needle having different diameters, as shown in the table 3 to the table 5, it was possible to obtain an experimental result which shows similar tendency as in the case of the 30G needle for dental use.

As explained above, according to the administration device of the present invention, it is possible to administer (inject) substances such as medicinal solution, immune cells and the like percutaneously to the dermis 100% without leakage and thereby, it is possible to obtain desired drug efficacy or effects. Furthermore, by making the puncture needle to go into in parallel with the dermis layer, it becomes possible to lengthen the distance from the releasing aperture which exists at the needlepoint of the puncture needle until the epidermis E and the body surface F, so that it is possible to make it hard for the substances to be administered to be leaked to the outside of the epidermis E or the body surface F. As a result thereof, it is possible to administer substances such as medicinal solution, immune cells or the like to the dermis certainly and relatively in a short time.

It should be noted that the above-described exemplified embodiments were explained by using examples in which substances such as medicinal solution, immune cells or the like are administered always to the dermis, but it is possible to use the administration device of the present invention also in a case in which substances are administered to an intracutaneous area, a subcutis or further a muscle other than the dermis.

Also, the administration device of the present invention is not limited by the above-mentioned each exemplified embodiment and besides that, it is needless to say that various modifications or changes can be employed for the materials, the constitutions or the like in the region without departing from the configuration of the present invention.

What we claim is:

1. A puncture device for puncturing skin with a puncture needle, the puncture device comprising:
   retaining means for holding the puncture needle;
   a fixing portion movably supporting the retaining means and possessing a flat contact surface to be fixed to a body surface;
   a positioning portion to which the fixing portion is rotatably connected and which possesses a flat surface to be fixed to the body surface;
   wherein in a state in which the positioning portion is fixed to the body surface, the fixing portion is configured to be rotated from a position where the flat contact surface of the fixing portion is approximately orthogonal to the flat surface of the positioning portion toward a body surface side to raise the skin of the body surface where the flat surface of the positioning portion is fixed; and
   the retaining means being configured to be moved to puncture the raised skin with the puncture needle passing through an opening window provided at an end of a positioning portion side part of the fixing portion.

2. The puncture device according to claim 1, wherein the fixing portion comprises a depressing surface adapted to be fixed to the body surface together with the positioning portion when the flat contact surface of the fixing portion is approximately orthogonal to the flat surface of the positioning portion, the depressing surface depressing the body surface where the depressing surface is fixed when the fixing portion is rotated toward the body surface side to raise the skin of the body surface where the flat surface of the positioning portion is fixed, and wherein the flat contact surface of the fixing portion is continuous with the depressing surface of the fixing portion and is fixed to the body surface by rotating the fixing portion toward the body surface side from the position where the flat contact surface of the fixing portion is approximately orthogonal to the flat surface of the positioning portion.

3. The puncture device according to claim 2, wherein the fixing portion and the positioning portion are each formed by approximately a rectangular plate body, and further comprising an interlink portion provided at one short side of the fixing portion and connected to a lower portion of a side surface of the positioning portion through a hinge portion, a side surface of the interlink portion of the fixing portion constituting the depressing surface.

4. The puncture device according to claim 2, wherein the flat contact surface of the fixing portion is approximately orthogonal to the depressing surface of the fixing portion.

5. The puncture device according to claim 2, wherein the opening window opens through the depressing surface.

6. The puncture device according to claim 1, wherein the flat contact surface of the fixing portion and the flat surface of the positioning portion which are to be fixed on the body surface each include an adhesion member for fixing the flat contact surface of the fixing portion and the flat surface of the positioning portion on the body surface.

* * * * *